United States Patent
Blatt et al.

(10) Patent No.: US 6,821,735 B1
(45) Date of Patent: Nov. 23, 2004

(54) PROTEIN INVOLVED IN ABSCISIC ACID SIGNALLING

(75) Inventors: Michael Blatt, Wye (GB); Barbara Leyman, Ghent (BE)

(73) Assignee: Plant BioScience Limited, Norfolk (GB)

( * ) Notice: Subject to any disclaimer, the term of this patent is extended or adjusted under 35 U.S.C. 154(b) by 0 days.

(21) Appl. No.: 09/509,738
(22) PCT Filed: Sep. 30, 1998
(86) PCT No.: PCT/GB98/02937

§ 371 (c)(1),
(2), (4) Date: May 24, 2000

(87) PCT Pub. No.: WO99/16880

PCT Pub. Date: Apr. 8, 1999

(30) Foreign Application Priority Data

Sep. 30, 1997 (GB) .............................. 9720784

(51) Int. Cl.⁷ .............................................. G01N 33/53
(52) U.S. Cl. ........................ 435/7.1; 530/350; 530/300; 530/324; 530/325; 530/326; 530/327; 530/328; 530/329; 530/330
(58) Field of Search ........................ 530/300, 324–330, 530/350; 435/7.1

(56) References Cited

PUBLICATIONS

Leung et al. 1994; Science 264:1448–1452.*
Silhavy et al. 1995; Plant Molecular Biology 27:587–595.*

* cited by examiner

*Primary Examiner*—Karen Cochrane Carlson
(74) *Attorney, Agent, or Firm*—Sheridan Ross PC

(57) ABSTRACT

An isolated protein capable of affecting an ABA response and comprising one or more of the following: (i) a hydrophobic C-terminus; (ii) an epimorphin pattern; (iii) a hydrophilic N-terminus; and (iv) a nucleotide binding site; or a variant thereof.

30 Claims, 43 Drawing Sheets

A.

B.

| Sucrose gradient fractionation | Active mRNA fraction |
| cDNA library construction | |
| Pool and subdivide | |
| Transcribe pools seperatly with T7 polymerase | |
| Assay and select positives | Assay ABA-evoked Cl current → Select positives → ABA Signalling Component cDNA (combination) |

A.

```
  1   S N P E E K E F L D W S K R V I I I E G T G K G L T L H R D    REK-Nt(5' end)
620   N K - Q R S S L L N W Q T R F N I I C G I A R G L L Y L H Q D  IRK1-It
621   - - - - - - - - L N W K D R F A I T N G V A R G L L Y L H Q D  SRK9-Bc
616   K K - - R S S N L N W K D R F A I I N G V A R G L L Y L H Q D  SRK4-Bo 32   S R L R I I H R D L K A S N I L L D E Q L N P K I S D F G M A  REK-Nt(5' end)
650   S R F R I I H R D L K A S N I L L D K E M N P K I S D F G M A  IRK1-It
644   S R F R I I H R D L K P G N I L L D K Y M I P K I S D F G M A  SRK9-Bc
645   S R F R I I H R D M K P S N I L L D K Y M I P K I S D F G M A  SRK4-Bo 63   R I F P G S D Q A N T E R V V G T                              REK-Nt(5' end)
681   R I F G G D E T D A N N T K R V                                IRK1-It
675   R I F A R D E T Q A R T D N A V G T                            SRK9-Bc
676   R I F A R D E T E A N T                                        SRK4-Bo
```

B.

```
  1   G L L C V Q E Y A E D R P N V S V V L S M L T S E I S D L P S  REK-Nt(3' end)
784   G L L C V Q E Q A E D R P N M A T V V L M L G S E S A T L P Q  IRK1-It
784   G L L C I Q E R A E H R P T M S S V V W M L G S E A T E I P Q  SRK9-Bc
785   G L L C I Q E R A E D R P T M S S V V W M L G S E A T D I P Q  SRK4-Bo 32   P A Q P A F I T R P S C S E K E S S K T Q G - - - - - - - S V  REK-Nt(3' end)
815   P K H P G F C L G S R P A D M D S S T S - N C D E S C - - T V  IRK1-It
815   P K P P V Y C L I A S Y Y A N N P S S S R Q F D D D E S W T V  SRK9-Bc
816   P K P P I Y C L I T S Y Y A N N P S S S R Q F E D D E S W T V  SRK4-Bo 56   N T V S I T I M E G R                                          REK-Nt(3' end)
843   N Q V T V T M L D G R                                          IRK1-It
846   D K Y T W S V I D A R                                          SRK9-Bc
847   N K Y T C S V I D A R                                          SRK4-Bo
```

FIG. 3

A.
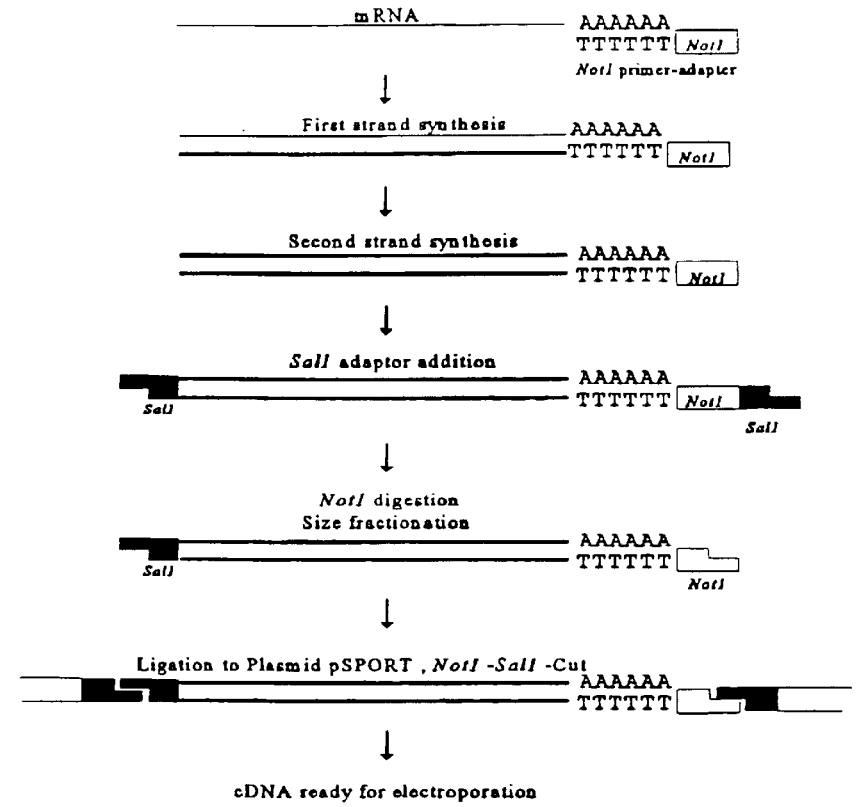
B.
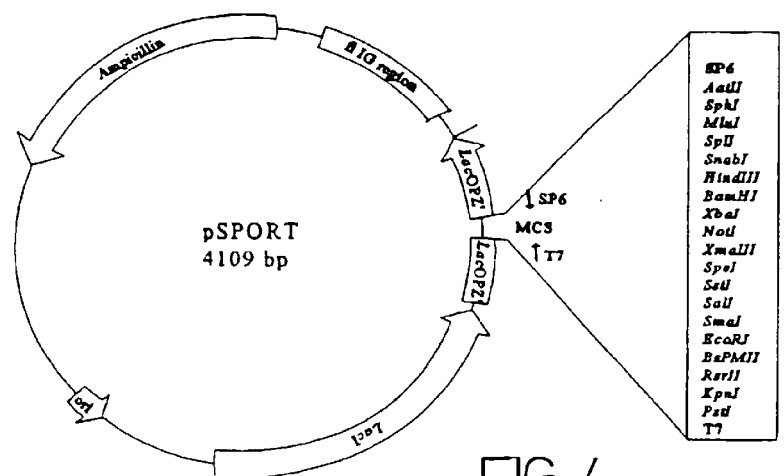
FIG. 4

FIG. 6

| | | |
|---|---|---|
| 17  | R F R A V T S A Y Y R S A V G A L L V Y D I S R K T T F E N I | smG-Nt2 |
| 74  | R F R A V T S A Y Y R G A V G A L I V Y D I S R R T T F D S V | Soybean |
| 74  | R F R A V T S A Y Y R G A V G A L I V Y D I T R R T T F D S V | L. Japonicus |
| 74  | R F R A V T S A Y Y R G A V G A L V V Y D I T R R T T F E S V | A. thaliana1 |
| 73  | R F R A V T S A Y Y R G A V G A L V V Y D I T R S S T F E N V | A. thaliana2 |
| 65  | R F R A V T S A Y Y R G A F G A L V V Y D I T R R T T F D S I | N. tabacum2 |
| 48  | Q C W L D E L H T H C D T T V A R M L V G N K C D L E N I R D | smG-Nt2 |
| 105 | G R W L D E L K T H C D T T V A M M L V G N K C D L E N I R A | Soybean |
| 105 | S R W L D E L K T H C D T T V A M M L V G N K C D L E N I R A | L. Japonicus |
| 105 | G R W L D E L K I H S D T T V A R M L V G N K C D L E N I R A | A. thaliana1 |
| 104 | G R W L D E L N T H S D T T V A K M L I G N K C D L E S I R A | A. thaliana2 |
| 96  | P R W L D E L K T H S D T T V A R M L V G N K C D L D N I R A | N. tabacum2 |
| 79  | V S I Y E G K N L A E E G L F F I E T S A L D S T N V K Q P | smG-Nt2 |
| 136 | V S I D E G K S L A E A E G L F F M E T S A L D S T N V K M A | Soybean |
| 136 | V S I E E G K S L A E A Q G L F F M E T S A L D S T N V R T A | L. Japonicus |
| 136 | V S V E E G K A L A E E E G L F F V E T S A L D S T N V K T A | A. thaliana1 |
| 135 | V S V E E G K S L A E S E G L F F M E T S A L D S T N V K T A | A. thaliana2 |
| 127 | V S V E E G K S L A E S E G M F F M E T S A L D A T N V N K A | N. tabacum2 |
| 110 | L K L S S A Q I Y Q N L S R K V L H S D S Y K T E L S V H P V | smG-Nt2 |
| 167 | F E M V I R E I Y N N V S R K V L N S E T Y K A E L S V N R V | Soybean |
| 167 | F E M V I R E I Y N N V S R K V L N S D T Y K A E L S V D R V | L. Japonicus |
| 167 | F E M V I L D I Y N N V S R K Q L N S D T Y K D E L T V N R V | A. thaliana1 |
| 166 | F E M V I R E I Y S N I S R K Q L N S D S Y K E E L T V N R V | A. thaliana2 |
| 158 | F D M V I R E I Y N S V S R K V L N S D S Y K A E L S V N R V | N. tabacum2 |

```
 11  L I F S L E T F L L V L L F F T L V S S S A S E I F F E E S F D D G   CAL-tN (5'end)
  6  N K L S F F C F F F L V S V L T L A P L A F S E I F L E E H F E G G   CRT1-At 45  W R S R W V K S D W K I S E G R A G S F K H I A G I W A G D P D D K   CAL-tN (5'end)
 40  W K S R W V L S D W K R N E G K A G T F K H T A G K W P G D P D N K   CRT1-At 79  G I K I Y N D A K H F A V S A K I P E F S N K N R T L V V Q Y S I K   CAL-tN (5'end)
 74  G I Q T Y N D A K H Y A I S A K I P E F S N K N R T L V V Q Y S V K   CRT1-At 113  F E Q D I E C G A Y I K L L S G Y V H K K F G G D T P Y S F M F       CAL-tN (5'end)
108  I E Q D I E C G A Y I K L L S G Y V H Q K Q F G G D T P Y S L M F     CRT1-At 147  G A D I C G S Q T K K F S C L I C F Y F G A L L P F L P E K N L       CAL-tN (5'end)
142  G P D I C G T Q T K K L H - V I V S Y Q G Q N Y P I - - K K D L       CRT1-At
```

A

```
  1  G V W H - - E P D I A K I S D S K K C L F I G E A E K L A F E E A E   CAL-Nt (3'end)
340  - I L - C D D P A Y A R S I V D D Y F A G H R E S E K E L F A E A E   CRT1-At 33  K V K K A K E E E A Q K A R E E G E R K R K E R G R - - D K H K D     CAL-Nt (3'end)
373  K E R K A R E D E E A R I A R E E G E R R R K E R D H R Y G D R R R   CRT1-At 65  R K K K R I N N D Y M D D Y H D E L                                   CAL-Nt (3'end)
407  R Y K R P N P R D Y M D D Y H D E L                                   CRT1-At
```

```
CCAAATCCCATCTCAAAATGAATGATCTATTTTCAGGATCTTTCTCTCGTTTCAGAGCTG        60
                 M  N  D  L  F  S  G  S  F  S  R  F  R  A
ACGATCAATCGGACTCTCACGCCATAGAAATGGGAGACATTACTGGCGGAGTCAATCTCG       120
 D  D  Q  S  D  S  H  A  I  E  H  G  D  I  T  G  G  V  N  L
ACAAATTCTTCGAAGATGTTGAAGCCATTAAAGACGAACTCAAAGGCCTCGAGAAAATCT       180
 D  K  F  F  E  D  V  E  A  I  K  D  E  L  K  G  L  E  K  I
ATTCCCAACTCCAATCTTCCCATGAAAAAAGCAAGACTCTTCACAACGCTAAAGCCGTTA       240
 Y  S  Q  L  Q  S  S  H  E  K  S  K  T  L  H  N  A  K  A  V
AAGATCTAAGATCCAACATGGATAATGACGTTTCCATGGCATTGAAGAAAGCCAAATTCA       300
 K  D  L  R  S  N  M  D  N  D  V  S  M  A  L  K  K  A  K  F
TCAAAGTTCGTCTCGAAGCCTTAGACAGATCAAATGCAGCGAATCGAAGCCTCCCTGGAT       360
 I  K  V  R  L  E  A  L  D  R  S  N  A  A  N  R  S  L  P  G
GTGGACCCCGGAAGTTCATCTGACAGGACGAGAACTTCAGTTGTGAACGGATTAAGGAAGA      420
 C  G  P  G  S  S  S  D  R  T  R  T  S  V  V  N  G  L  R  K
AACTTCAAGAGTCAATGAATCAGTTCAACGAGCTAAGGCAAAAGATGGCATCTGAATATA       480
 K  L  Q  E  S  M  N  Q  F  N  E  L  R  Q  K  H  A  S  E  Y
GGGAAACAGTTCAACGACGATATTATACCGTCACAGGAGAAAATCCTGATGAAGCAGTTC       540
 R  E  T  V  Q  R  R  Y  Y  T  V  T  G  E  N  P  D  E  A  V
TTGATACACTCATATCTACAGGTCAAAGTGAGACGTTCTTGCAAAAGGCAATTCAAGAGC       600
 L  D  T  L  I  S  T  G  Q  S  E  T  F  L  Q  K  A  I  Q  E
AAGGGAGAGGACAAGTGATGGATACAGTTATGGAAATTCAAGAAAGGCATGAAGCTGTGA       660
 Q  G  R  G  Q  V  M  D  T  V  M  E  I  Q  E  R  H  E  A  V
AGGAATTGGAGAGGAATTTGAAAGAATTGCATCAAGTATTCTTGGACATGGCTGTTTTGG       720
 K  E  L  E  R  N  L  K  E  L  H  Q  V  F  L  D  M  A  V  L
TTGAAAGTCAAGGAGCTCAACTTGATGATATTGAGAGCCAAGTGAATAGGGCTAATTCCT       780
 V  E  S  Q  G  A  Q  L  D  D  I  E  S  Q  V  N  R  A  N  S
TCGTTAGAGGGGGTGCTCAGCAACTGCAAGTGGCAAGGAAGCACCAGAAGAACACTAGAA       840
 F  V  R  G  G  A  Q  Q  L  Q  V  A  R  K  H  Q  K  N  T  R
AATGGACTTGTTTTGCTATTATTCTTCTGCTTATCATCATTTTGGTGGTGGTTCTTTCTA      900
 K  W  T  C  F  A  I  I  L  L  L  I  I  I  L  V  V  V  L  S
TTCAGCCATGGAAAAAATGAGAATTTGTCTATGGTCAAAGGTCTTCTGGTGGACCCCTTC       960
 I  Q  P  W  K  K  .
AATGTTTTGAATATTCTAAATTTTTATATTTTATTATTTTAGCCATGCTTATTATTTTGT      1020
GTTATTTTGGATTTTTTTTTTGTTTTTAATGTGGGGAAGAGTAAAACTGGATGGGGGTCCA     1080
TGTGCTATTTAGAGAAATACTTGGGAGTTCTCTTTTTGTAATTATTGCTGTATTTAGAGT      1140
ATAATTCTTTTTCTATATTGTTGGCACGTTAATTTGTTTGTTTGATTATATTCTCATTTA      1200
GATTT                                                              1205
```

FIG.9 A

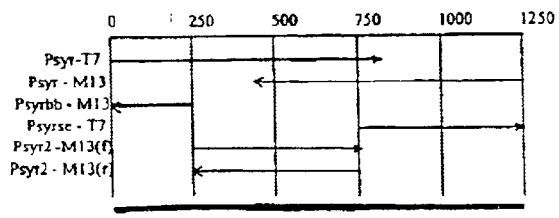

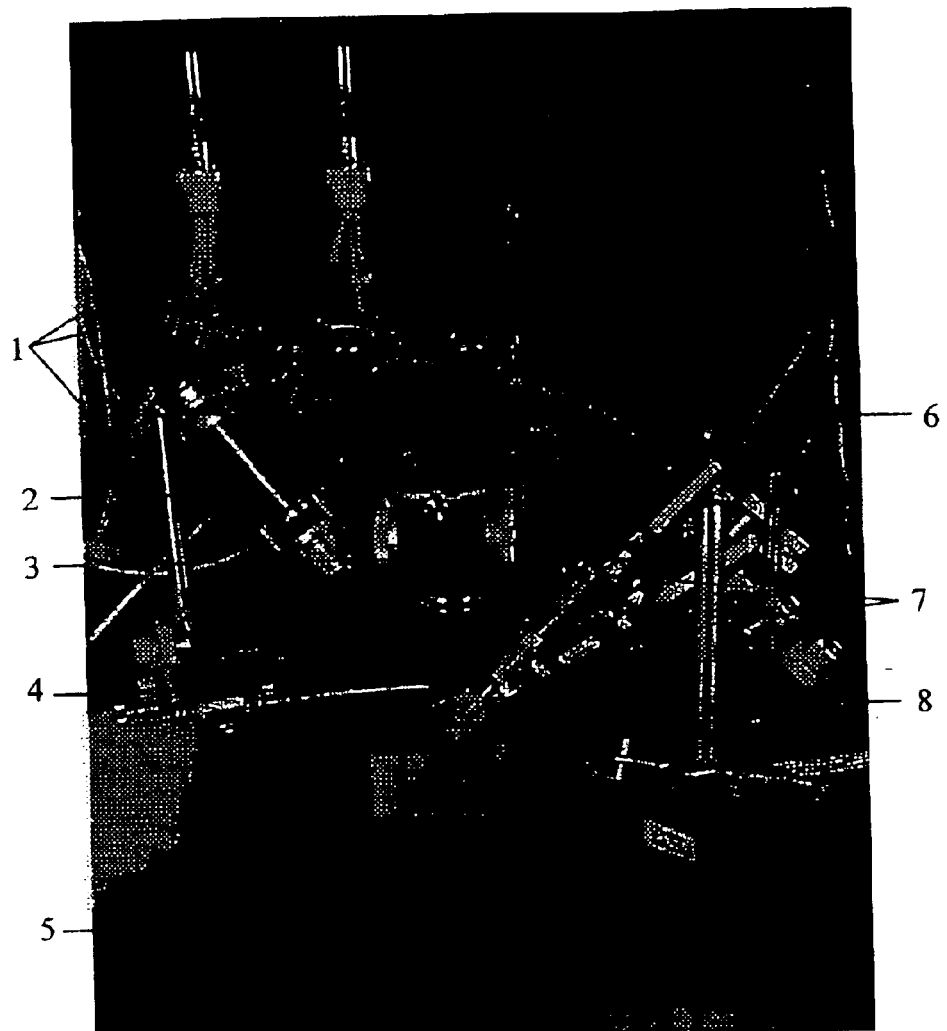
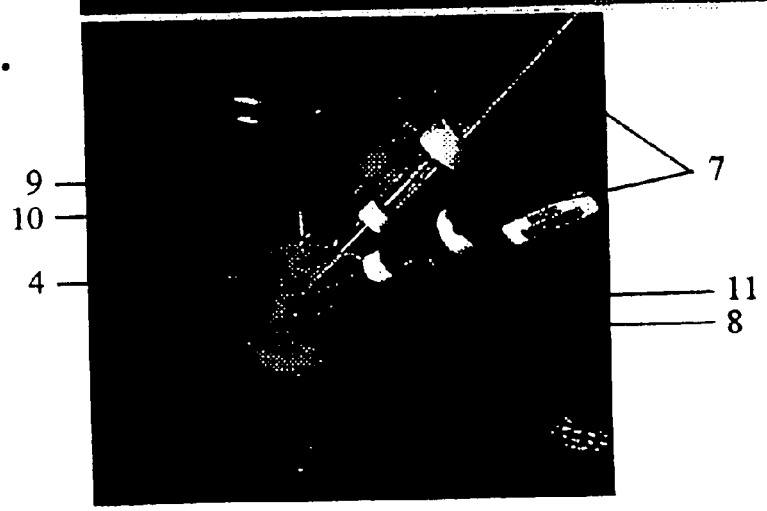
FIG. 13

| Pool size | - ABA | + ABA |
|---|---|---|
| | 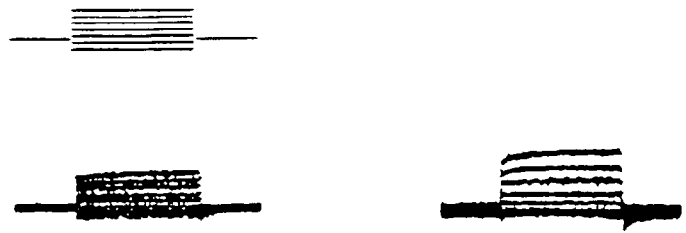 | |
| 20000 | | |
| 2000 |  | |
| 200 |  | |
| 20 | 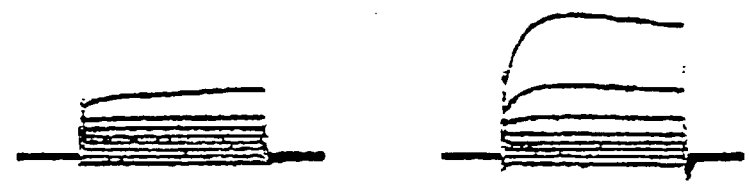 | |
FIG. 20

2.5 mM K⁺
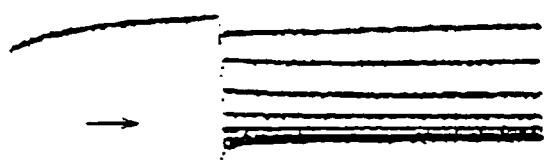
25 mM K⁺
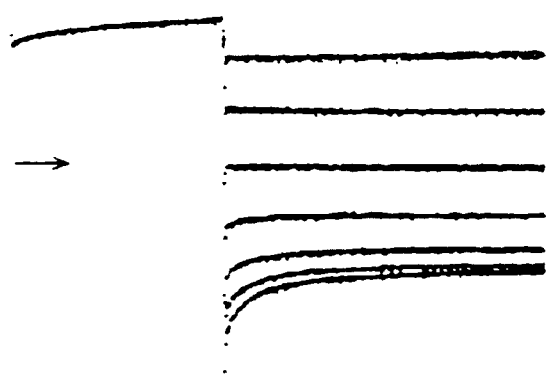
FIG. 24

FIG. 27
A.  LQVARK      SYR-Nt
    TKKALK      syntaxin 1A-DRO
    TKKAVK      syntaxin 1A-RAT, syntaxin 1A-HUM
    TDKAVK      SSO1-yeast
    TNKAVK      SSO2-yeast
B. 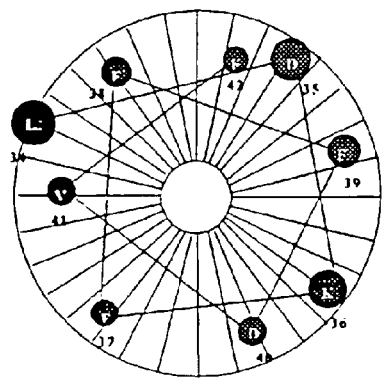 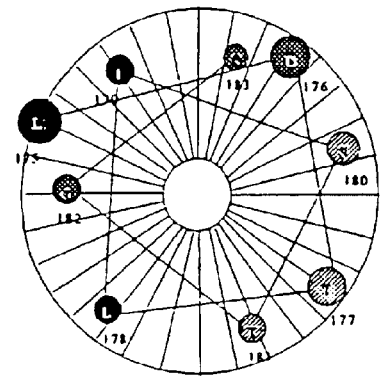

A.

Contr -ABA

Contr +ABA

B.

BotC -ABA

BotC +ABA

C.

BotD -ABA

BotD +ABA

FIG. 28

A. Contr inst 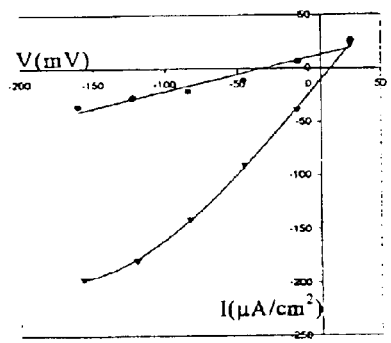 Contr St-St 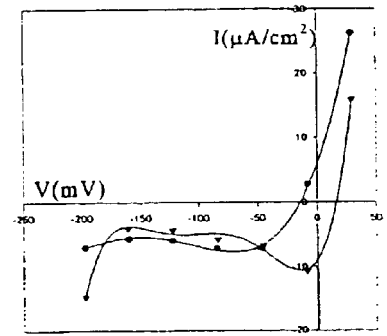
B. BotC Inst 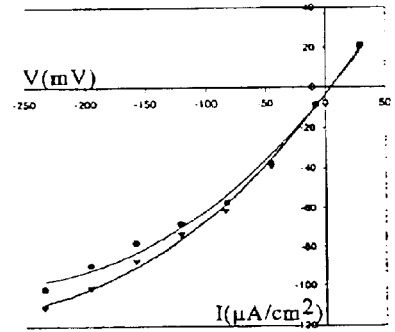 BotC St-St 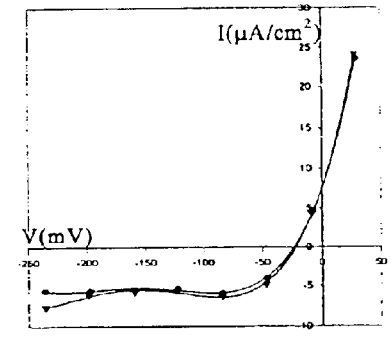
C. BotD Inst 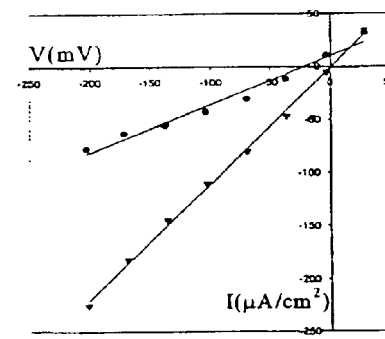 BotD St-St 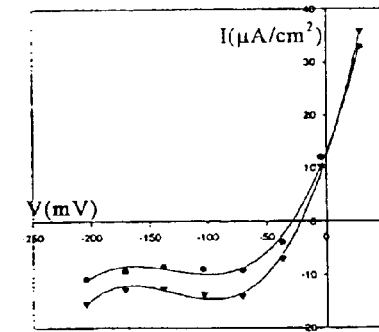
- −ABA
- +ABA
FIG. 29

FIG. 30

A.
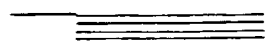
Contr -ABA                                   Contr +ABA
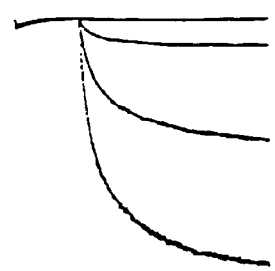              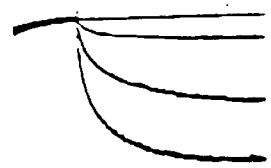
B.       BotC -ABA                            BotC +ABA
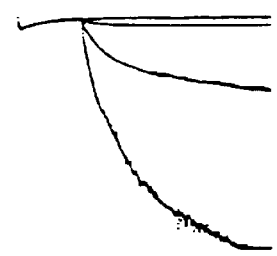              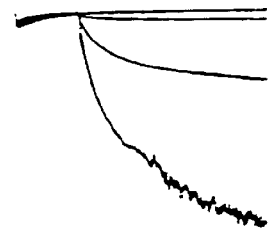
C.       BotD -ABA                            BotD +ABA
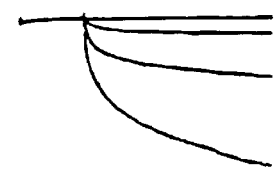              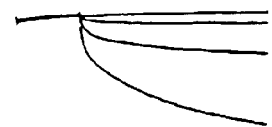
FIG. 31

A.
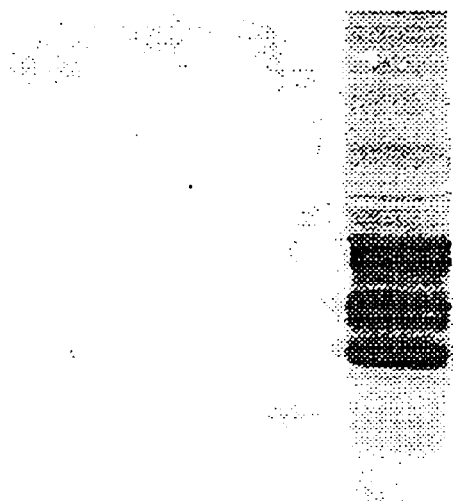
B.
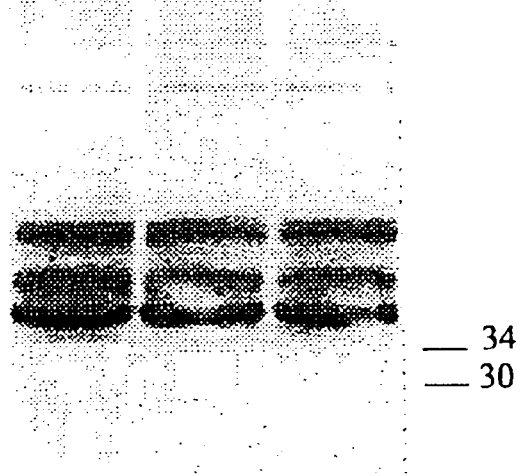
FIG. 36

```
TTTAGATTTACTCTTATATTAGTTTGTTTGTTTAATTGGACGGTTGTTATATCTTTTTCTTA
ATATGAGATTTATGTCGTTATTAATGTTTTTCTCTTGAGGGTTCATAAAGAGATTTATCGTG
TACCTGGGGGTAGGTCAAATGAGAAGGGGTGTAATTTTTGTTTTTTTTTTAGGTTTTATTGT
GTTTTATTATTCGTACCGATTTTATTATTTTATATTTTAAATCTTATAAGTTTTGTAACTT
CCCCAGGTGGTCTTCTGGAAACTGGTATCTGTTTAAGAGTAAAAAAGGTACCGACTTATCTT
TCTTGGTGGTGGTTTTACTACTATTCGTCTTCTTATTATCGTTTTGTTCAGGTAAAAGATCA
CAAGAAGACCACGAAGGAACGGTGAACGTCAACGACTCGTGGGGAGATTGCTTCCTTAATC
GGGATAAGTGAACCGAGAGTTATAGTAGTTCAACTCGAGGAACTGAAAGTTGGTTTTGTCGG
TACAGGTTCTTATGAACTACGTTAAGAAAGTTTAAGGAGAGGTTAAGGAAGTGTCGAAGTAC
GGAAAGAACTTAAAGGTATTGACATAGGTAGTGAACAGGAGAGGGAACGAGAACTTAACGGA
AAACGTTCTTGCAGAGTGAAACTGGACATCTATACTCACATAGTTCTTGACGAAGTAGTCCT
AAAAGAGGACACTGCCATATTATAGCAGCAACTTGACAAAGGGATATAAGTCTACGGTAGAA
AACGGAATCGAGCAACTTGACTAAGTAACTGAGAACTTCAAAGAAGGAATTAGGCAAGTGTT
GACTTCAAGAGCAGGACAGTCTACTTGAAGGCCCAGGTGTAGGTCCCTCCGAAGCTAAGCGA
CGTAAACTAGACAGATTCCGAAGCTCTGCTTGAAACTACTTAAACCGAAAGAAGTTACGGTA
CCTTTGCAGTAATAGGTACAACCTAGAATCTAGAAATTGCCGAAATCGCAACACTTCTCAGA
ACGAAAAAGTACCCTTCTAACCTCAACCCTTATCTAAAAGAGCTCCGGAAACTCAAGCAGA
AATTACCGAAGTTGTAGAAGCTTCTTAAACAGCTCTAACTGAGGCGGTCATTACAGAGGGTA
AAGATACCGCACTCTCAGGCTAACTAGCAGTCGAGACTTTGCTCTCTTTCTAGGACTTTTAT
CTAGTAAGTAAAACTCTACCCTAAACC
```

FIG. 40

FIG. 42
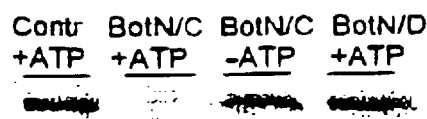
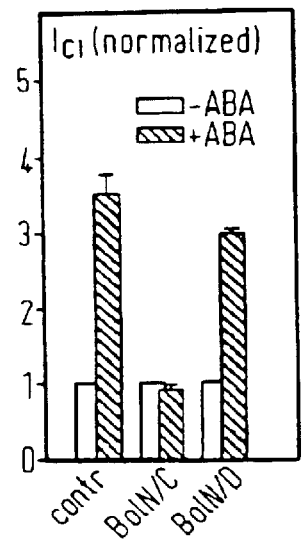
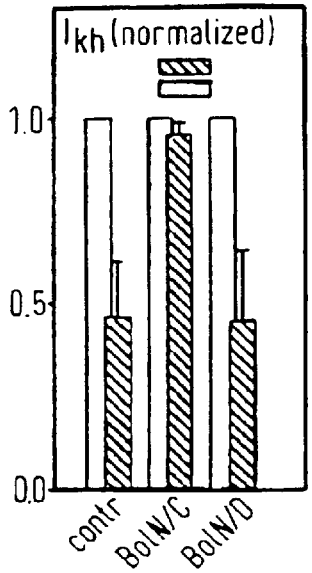
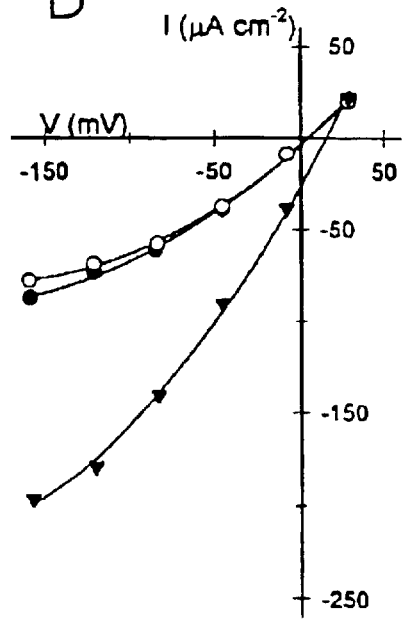

PROTEIN INVOLVED IN ABSCISIC ACID SIGNALLING

This application claims the benefit of priority under 35 U.S.C. § 371 to PCT Patent Application No. PCT/GB98/02937, filed Sep. 30, 1998, which designated the United States and was published in English, and which claims the benefit of foreign priority under 35 U.S.C. § 119 to Great Britain Patent Application No. 9720784.9, filed Sep. 30, 19971.

The present invention relates to an absicisic acid (ABA) signalling component, nucleic acid encoding the signalling component, and processes employing the same.

The plant phytohormone ABA plays an important role in growth and development of plants. In seeds it helps in embryogenesis and formation of seed-storage proteins. It prevents premature germination and growth of many seeds and buds. In vegetative tissue ABA protects the plant against adverse environmental conditions such as drought, high salinity, cold temperature or frost. Many of the actions of ABA result in rather long-term physiological changes and appear mainly to involve modification of gene expression at transcriptional level. Over 150 ABA responsive genes have been isolated from various plant species.

The importance of ABA as a stress hormone in connection with a lack of water was first suggested in 1969 by STC Wright and RWP Hiron at Wye College, London University. They found that ABA content of wheat leaves rose by a factor of 40 during the first half hour of wilting. Similar rise in ABA is now detected in leaves of monocot as well as dicot plants. Application of ABA to leaves causes stomatal closing or inhibits stomatal opening as observed in numerous species. Therefore, during water stress, increased ABA-levels reduce water loss.

We have found a novel protein that mediates in signalling evoked by ABA, and which responds to ABA.

According to the present invention there is now provided a protein capable of affecting an ABA response and comprising one or more of the following:

(i) a hydrophobic C-terminus;

(ii) at least one coiled coil region;

(iii) an EF-hand consensus sequence;

(iv) a nucleotide binding site; and (v) a hydrophilic N-terminus;

or a variant thereof.

In a preferred embodiment, the protein has (i), (ii), (iii) and (iv) as defined above, and optionally (v).

Further, the protein may also be capable of being cleaved by botulinum C. Thus preferably the protein includes two recognition domains for botulinum C and/or a cleavage site.

Preferably at least one of the coiled coil regions corresponds to an epimorphin pattern.

Preferably there are three coiled coil regions.

Preferably there are three coiled coil regions, at least one of which corresponds to an epimorphin pattern.

Preferably the protein further comprises phosphorylation sites.

The protein may be described as a novel syntaxin (t-SNARE) homolog. At the cellular level, ABA is best characterised by its action in regulating $K^+$ ands $Cl^-$ channels at the plasma membrane of stomatal guard cells, leading to stomatal closure that reduces transpirational water loss from leaf. The protein of the present invention may be a membrane-anchored protein that is associated with the plasma membrane. In vivo, both cleavage of the protein by Botulinum C toxin and competition by a soluble C-truncated fragment of the protein have been found to prevent ABA action in controlling $K^+$ and $Cl^-$ channels in the guard cells. These, and additional results, show that the protein of the present invention is involved in an ABA signalling complex, and responds to ABA.

The features of the protein can be defined as follows with reference to SEQ ID NO:24

| | Feature | Intervals — amino acids |
|---|---|---|
| (i) | hydrophobic C-terminus | 282–296/280–294 |
| (ii) | coiled coil region/epimorphin pattern | 210–247/216–240 |
| (iii) | an EF-hand consensus sequence | 16–28 |
| (iv) | nucleotide binding site | 116, 118 and 120/114–119. |
| (v) | hydrophilic N-terminus | 1–281/1–279 |
| (vi) | botulinum cleavage sites | 269–274 |

In an especially preferred embodiment, the protein comprises the amino acid sequence shown in SEQ ID NO:2 or SEQ ID NO:4.

The present invention includes variants of the protein defined above. Such variants include proteins having 50% or more overall homology with the sequence of SEQ ID NO:2. Typically the homology is 60% or more, more typically 65%, preferably 70%, more preferably 75%, even more preferably 80% or 85%, especially preferred are 90%, 95%, 98% or 99% homology.

Percentage homology preferably is calculated on the basis of amino acids that are identical in corresponding positions in the two sequences under consideration. Conservative substitutions are not taken into account. In calculation of percentage homology of a putative protein under investigation with the SEQ ID NO:2 or SEQ ID NO:4, if the protein under investigation has a different length, then the calculation is based on the amino acids in the portion of the molecule under investigation that overlaps with the sequence shown in SEQ ID NO:2 or SEQ ID NO: 4.

In particular, the term "homology" as used herein may be equated with the term "identity".

Here, sequence homology can be determined by a simple "eyeball" comparison of any one or more of the sequences with another sequence to see if that other sequence has at least 75% identity to the sequence(s).

Relative sequence homology (i.e. sequence identity) can also be determined by commercially available computer programs that can calculate % homology between two or more sequences. A typical example of such a computer program is CLUSTAL.

Sequence homology (or identity) may moreover be determined using any suitable homology algorithm, using for example default parameters. Advantageously, the BLAST algorithm is employed, with parameters set to default values. The BLAST algorithm is described in detail in, for example: Altschul, S. F., Gish, W., Miller, W., Myers, E. W. & Lipman, D. J. (1990) "Basic local alignment search tool." J. Mol. Biol. 215:403–410; Madden, T. L., Tatusov, R. L. & Zhang, J. (1996) "Applications of network BLAST server" Meth. Enzymol. 266:131–141.; Gish, W. & States, D. J. (1993) "Identification of protein coding regions by database similarity search." Nature Genet. 3:266–272; Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389–3402; Karlin, S. & Altschul, S. F. (1990) "Methods for assessing the statistical significance of molecular sequence features by using general scoring schemes." Proc. Natl. Acad. Sci. USA 87:2264–2268; Karlin, S. & Altschul, S. F. (1993) "Applications and statistics for multiple high-scoring segments in molecular sequences." Proc. Natl. Acad. Sci. USA 90:5873–5877, which are incorporated herein by reference. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul with a few enhancements.

Analysis may also be carried out using Lasergene DNA, Madison, U.S.A.

It will be appreciated that proteins capable of affecting an ABA response and/or responding to ABA from other species will exhibit inter-species differences, for example, differences in protein length, amino acid sequence and carbohydrate modifications. There may, for example, be variations in the C- and/or N-terminal residues, and in molecular weight.

In a general sense the term "variant" includes a protein which retains the essential properties, in the present case the ability to affect an ABA response and/or respond to ABA. Variants include allelic variants, and proteins, which differ by conservative amino acid changes. The variants may be natural or non-naturally occurring variants made, for example, by mutagenesis.

By conservative amino acid changes we mean replacing an amino acid from one of the amino acid groups, namely hydrophobic, polar, acidic or basic, with an amino acid from within the same group. An example of such a change is the replacement of valine by methionine and vice versa.

Confirmation that a protein is one which is capable of affecting an ABA response may be made by consideration of sequence homology and/or consideration of its structural relationship.

In addition to full-length proteins, the present invention also encompasses molecules that comprise less than a full length sequence. Such molecules or fragments may be polypeptides or peptides. For use as a substitute, a fragment should retain one or more of the biological activities of the parent molecule.

One method that may be used to test a putative molecule for the ability to affect an ABA response is the use of *Xenopus laevis* oocycles as a heterologous expression as described below.

The present invention does not cover the native protein according to the present invention when it is in its native environment and when it has been expressed by its native nucleotide coding sequence which is also in its natural environment and when that nucleotide sequence is under the control of its native promoter which is also in its natural environment. The protein of the present invention may also be isolated in the sense that it is substantially free from other proteins with which it is ordinarily associated. In addition the present invention does not cover the native nucleotide coding sequence according to the present invention in its natural environment when it is under the control of its native promoter which is also in its natural environment.

Although in the specific non-limiting example described below the ABA signalling component was obtained from *Nicotiana tabacum* (tobacco) the present invention relates in general to an ABA signalling component. For example, ABA signalling components from dicotyledonous and monocotyledonous plants, including cereals such as wheat, barley, rice, maize and sorghum; field crops other than tobacco such as canola, sunflower, sugarbeet and cotton; fruit and vegetables. As an example, the corresponding ABA signalling component in maize may be found using reverse transcription followed by polymerase chain reaction (RT-PCR) using known techniques and primers devised from the sequences of SEQ ID NO: 1. Confirmation that an ABA signalling component has been arrived at can be achieved using the assays of the present invention and described herein.

Using this approach we have also determined the corresponding ABA signalling component from *Arabidopsis thaliana*. The nucleic acid sequence is shown as SEQ ID NO:3 and corresponding amino acid sequence as SEQ ID NO:4. The present invention also includes variants of these sequences defined herein. For the avoidance of doubt the terms "a protein capable of affecting an ABA response" and "ABA signalling component" are used interchangeably. The terms refer to a molecule involved in the signal transduction pathway of the hormone abscisic acid. Similarly in relation to the assay method of the invention "signalling component" refers to a molecule involved in the signal transduction pathway of a hormone.

The protein of the present invention may be used in screens to detect protein-protein interactions. In particular, the protein may be used to screen for other members of a signal transduction pathway. One suitable method is the so-called two-hybrid system, in which the DNA-binding domain of the GAL4 protein is fused to the protein of the present invention. A second plasmid is constructed comprising the activation domain of the GAL4 protein fused to a protein (or peptide or polypeptide) under investigation. Interaction between the protein of the present invention and the protein under investigation leads to transcriptional activation of a reporter gene, such as detection by expression of a GAL1-lacZ gene fusion.

Thus the present invention also provides fusion proteins comprising the protein of the present invention, and similarly protein/nucleic acid complexes comprising the protein of the present invention. The protein and/or nucleic acid of the present invention may be associated with, for example, a targeting sequence, such a sequence which targets the nucleic acid encoding for the protein to a cell membrane.

Thus, the present invention also provides a method of detecting proteins which interact with the present protein. Interactive proteins found using such a screen are also the subject of the present invention. For example, we have found that there is interaction between the SYR protein of the present invention (see below) and clone 4 (see table 1) which is identified as having a phosphatase inhibitor domain.

Also included within the present invention are truncated proteins derivable from the proteins defined above. Typically such truncated proteins will be able to compete with the non-truncated protein in an ABA signalling pathway, and/or be capable of giving rise to antibodies to the non-truncated protein. Examples of such truncated proteins include Sp1 comprising amino acids 115–127 of SEQ ID NO:2 and Sp2 comprising amino acids 1–279 of SEQ ID NO:2. Thus, the present invention further includes a method of raising immunoglobins comprising administering a protein of the present invention to a mammal, such as a rabbit or human, and optionally isolating the immunoglobins generated.

The present invention also provides nucleic acid encoding the protein of the present invention.

In particular, according to another aspect of the present invention there is provided nucleic acid comprising the sequence from positions 18 to 917 shown in SEQ ID NO: 1, or from positions 77 to 991 shown in SEQ ID NO:3.

The present invention also includes DNA which shows homology to the sequence of the invention. Typically homology is shown when 50% or more of the nucleotides are common, more typically 60% or 65%, preferably 70%, more preferably 75%, even more preferably 80% or 85%, especially preferred are 90%, 95%, 98% or 99% or more homology.

The present invention also includes DNA which hybridises to the DNA of the present invention. Preferably such DNA codes for at least part of an ABA signalling component.

The present invention also encompasses nucleotide sequences that are complementary to the sequences presented herein, or any derivative, fragment or derivative thereof. If the sequence is complementary to a fragment thereof then that sequence can be used a probe to identify similar coding sequences in other organisms etc.

The present invention also encompasses nucleotide sequences that are capable of hybridising to the sequences that are complementary to the sequences presented herein, or any derivative, fragment or derivative thereof.

The term "complementary" also covers nucleotide sequences that can hybridise to the nucleotide sequences of the coding sequence.

The term "variant" also encompasses sequences that are complementary to sequences that are capable of hydridising to the nucleotide sequences presented herein.

Preferably such hybridisation occurs at, or between, low and high stringency conditions. In general terms, low stringency conditions may be defined as 3×SSC at about ambient temperature to about 65° C., and high stringency conditions as 0.1×SSC at about 65° C. SSC is the name of a buffer of 0.15M NaCl, 0.015M trisodium citrate. 3×SSC is 3 times as strong as SSC and so on.

The present invention also comprises sequences obtained from PCR techniques using a primer derived from the sequence of the present invention.

The DNA of the invention may be cDNA or DNA which is in isolated form.

The invention further includes DNA which is degenerate as a result of the genetic code to the DNA of the present invention and which codes of a protein which is capable of affecting an ABA response, and/or responding to ABA.

The present invention also relates to vectors which comprise the nucleic acid of the present invention, host cells which are genetically engineered with the vectors of the present invention and the production of proteins of the present invention by recombinant techniques. Such system will be well known to those skilled in the art. The term "vector" includes expression vectors and transformation vectors. The term "expression vector" means a construct capable of in vivo or in vitro expression.

Preferably the host cell is a plant, seed, fungus or mammalian cell. For the avoidance of doubt fungus includes yeast. Thus the present invention also provides suitably transformed plants, seeds, fungi and mammals.

The present invention therefore provides nucleic acid according to the present invention which is operably linked to a promoter. It is proposed that this system may be used in a method of selecting compounds capable of affecting a plant's response to stress. Such a method may comprise screening compounds which bind to the expressed ABA signalling component and selecting compounds exhibiting said binding.

The invention thus further provides compounds selected using said screen and particularly their use as agrochemicals.

Agrochemical formulations are known and a skilled worker would readily be able to formulate an acceptable composition comprising an effective amount of the agrochemical.

A particularly preferred feature of the present invention is a plant or seed transformed with the nucleic acid of the present invention such that the ABA-signalling component of the present invention is expressed or rather overexpressed, in the plant or seed.

In such cases the promotor may be an inducible promotor. The advantage of using such a system is that expression can be controlled.

Such transformed plants, which may be monocotyledonous as well as dicotyledonous, may have improved growth and development over non-transformed plants. This may include reduced premature growth of buds and improved protection/tolerance against adverse environmental conditions such as drought, high salinity, cold temperature and frost. A particular feature may be improved tolerance to water stress. One way this may manifest itself is through reduced water loss. Plants will be expected to show reduced wilting.

The transformed seeds may have improved embryogenesis and better seed-storage protein formation compared to the wild-type. They may also show reduced premature germination and growth.

The method employed for transforming the host cells is not especially germane to this invention and any method suitable for the target host may be used. For example, transgenic plants are obtained by regeneration from the transformed cells. Numerous transformation techniques are known from the literature such as agroinfection using *Agrobacterium tumefaciens* or its Ti plasmid, electroporation, microinjection of plant cells and protoplasts, and microprojectile transformation.

Neither is the plant species into which the sequence is inserted particularly germane to the invention. Dicotyledonous and monocotyledonous plants can be, transformed. This invention may be applied to any plant for which transformation techniques are, or become, available. The present invention can therefore be used in a variety of plants, including field crops such as canola, sunflower, tobacco, sugarbeet, and conon; cereals such as wheat, barley, rice, maize and sorghum; fruit and vegetables. The invention is also suitable for use in a variety of tissues, including roots, leaves, stems and reproductive tissues.

Mammalian homologs of the sequences derivable from plants may have application in therapy, and particularly in gene therapy. Thus according to a further aspect of the present invention there is provided pharmaceutical compositions comprising the protein and nucleic acid of the present invention and a pharmaceutically acceptable diluent, excipient, carrier or adjuvant.

The pharmaceutical composition may be for human or animal usage. Typically, a physician will determine the actual dosage which will be most suitable for an individual subject and it will vary with the age, weight and response of the particular individual.

The composition may optionally comprise a pharmaceutically acceptable carrier, diluent, adjuvant or excipient. The choice of pharmaceutical carrier, excipient, adjuvant or diluent can be selected with regard to the intended route of administration and standard pharmaceutical practice. The pharmaceutical compositions may comprise as—or in addition to—the carrier, excipient, adjuvant or diluent any suitable binder(s), lubricant(s), suspending agent(s), coating agent(s), solubilising agent(s), and other carrier agents that may aid delivery.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The present invention also provides an anti-sense sequence and host cells further comprising an anti-sense sequence to the nucleic acid of the present invention. Again such sequences may be used in screening methods.

Various further preferred features and embodiments of the present invention will now be described by way of non-limiting example with reference to the accompanying drawings, in which:

FIG. 1 is a diagram of documented effects on inward $K^+$ channels of ABA and signalling intermediates. Filled arrow indicates that elevation of $Ca^{2+}$ release by $IP_3$. Open arrows indicate inhibition. Hatched arrow indicates that elevation, by ABA, of cytosolic $Ca^{2+}$ levels is variable.

FIG. 3 shows alignment of the deduced amino acid sequence of clone number 9 (rek-Nt) (SEQ ID NO:6) with related receptor kinase protein sequences of different plant sequences. The homologous receptor kinases are SRK4 from *Brassica oleracea* (S39911, Kumar and Trick, 1993; SEQ ID NO:9); SRK9 from *Brassica campestris* (D30049; SEQ ID NO:8) or IRK1 from *Ipomoea trifida* (U2W48; SEQ ID NO:7).
A. N-terminus: deduced from the nucleotide sequence obtained using the T7 primer
B. C-terminus; deduced from the nucleotide sequence obtained using the M13(f) primer.

FIG. 4A illustrates steps in the construction of an expression library;

FIG. 4B is a map of the pSPORT1 expression vector used for cloning the cDNA library.

Figure 5:
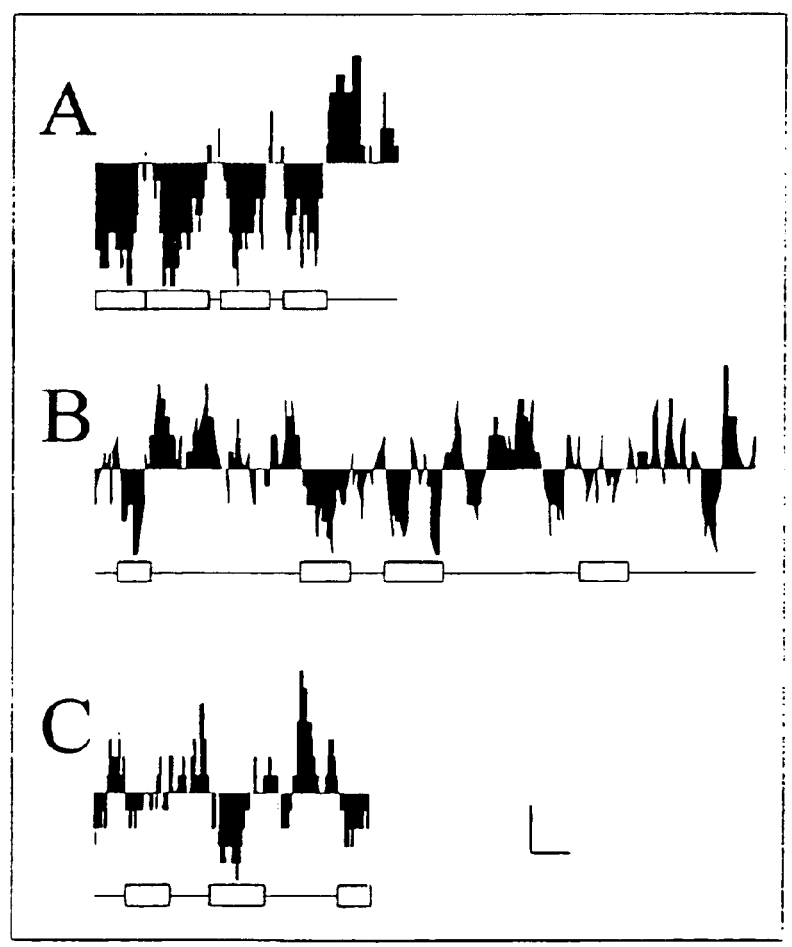

FIG. 5 shows hydrophilicity plots and predicted hydrophobic domains of the three proteins without significant homology. Amino acid sequence is deduced from clones number 2 (A), 8 (B) and 12 (C). Hydrophilicity plots and hydrophobic regions are as predicted using the Kyte-Doolittle algorithms. Scale: horizontal: 20 amino acids; vertical: 1 unit (Kyte-Doolittle).

FIG. 6 shows alignment of the deduced amino acid sequence of clone number 15 (smG-Nt; SEQ ID NO: 14) with related small Rab G-proteins from other plant species: GRM1 from *G. max*, (S47101, Borg and Poulsen, 1994; SEQ ID NO:15); RAB11G from *L. japonicus* (Z73955, Borg et al. 1997; SEQ ID NO: 16) ARA-4 (SEQ ID NO: 17) and RAB11 (SEQ ID NO: 18) both from *A. thaliana* (P28187, Anai et al. 1994 and Y08904, Lin and Lin,1997); NT-RAB11E (SEQ ID NO: 18) another small GTP binding protein of *N. tabacum* (L29272, Haizel et al 1995).

FIG. 7 shows alignment of the deduced amino acid sequence of clone number 19 (Cal-Nt; SEQ ID NOs:20 and 22) with a related calreticulin protein sequence CRT1 of *A. thaliana* (U66343, Nelson et al. 1997; SEQ ID NOs:21 and 23).
A. Alignment of the N-terminus of cal-Nt (SEQ ID NO:20) deducted from the nucleotide sequence obtained using the T7 primer. Box: the hydrophobic leader sequence.
B. Alignment of the C-terminus of cal-Nt (SEQ ID NO:22) deduced from the nucleotide sequence obtained sing the M13(f) primer. Box: the HDEL conserved domain.

Figure 8:
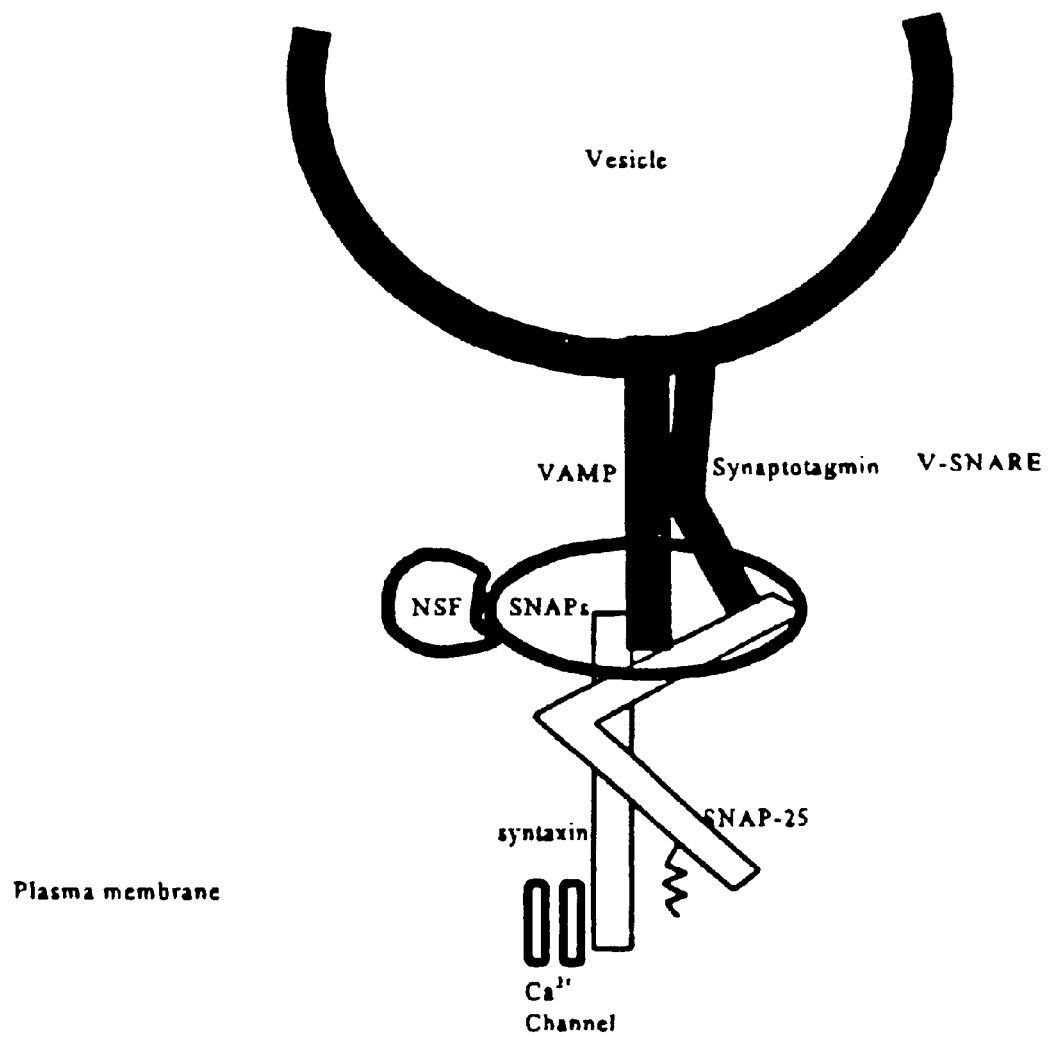

FIG. 8 is a cartoon of the protein-protein interaction among the major components during vesicle docking and fusion steps.

FIG. 9A shows the nucleotide sequence of the syr gene (SEQ ID NO:1) and predicted amino acid sequence (SEQ ID NO:2);

FIG. 9B shows contig of the sequence reactions.

Figure 10:
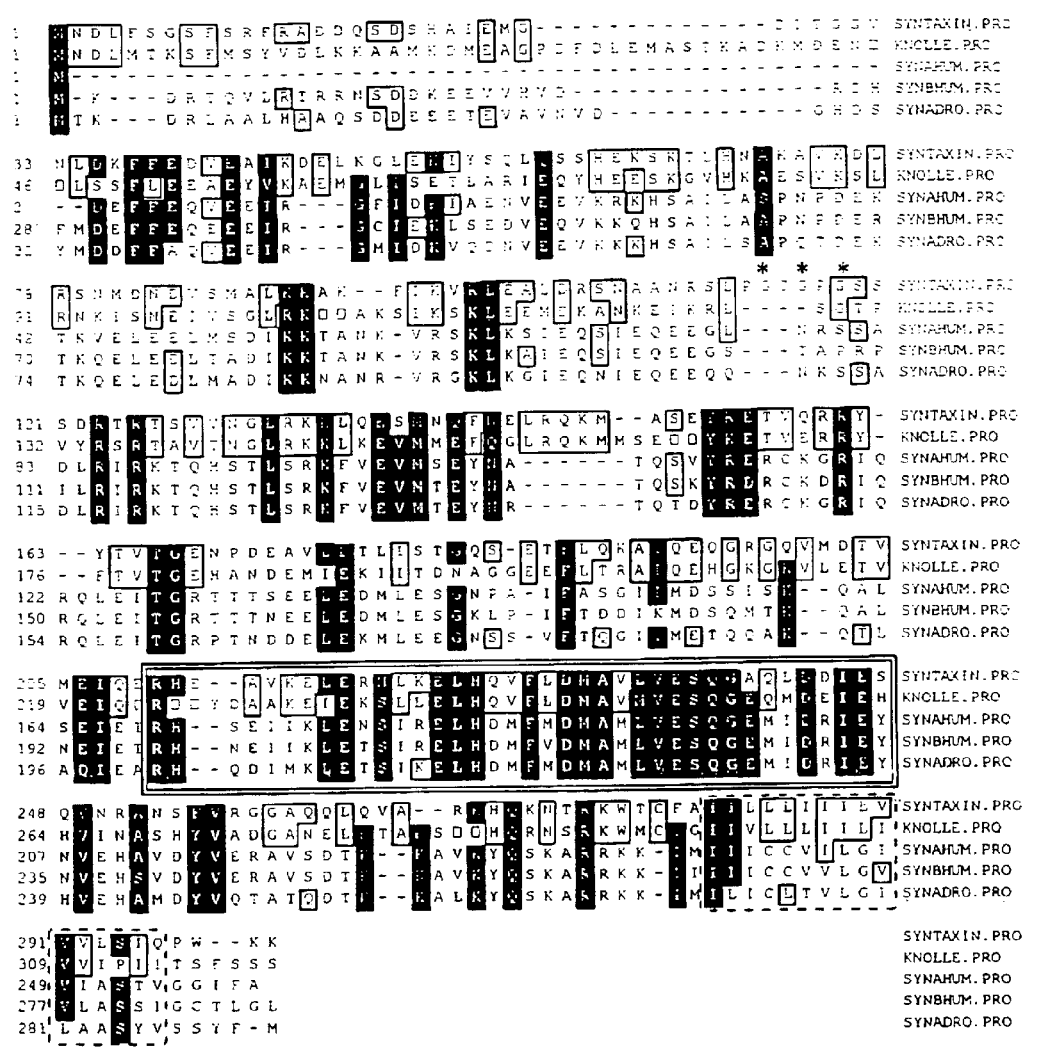

FIG. 10 shows alignment of the amino acid sequence of SYR-Nt (*Nicotiana tabacum*; SEQ ID NO:2) with KNOLLE-At (*Arabidopsis thaliana*, Lukowitz et al 1996; SEQ ID:NO:24), SYN1A-HUM (Bennett, et al., 1992; SEQ ID NO:25) and SYN1B-HUM (accession number R08740; SEQ ID NO:26), two different members of the human syntaxin family, and syntaxin A of Drosophila (SEQ ID NO:27).

Figure 11:
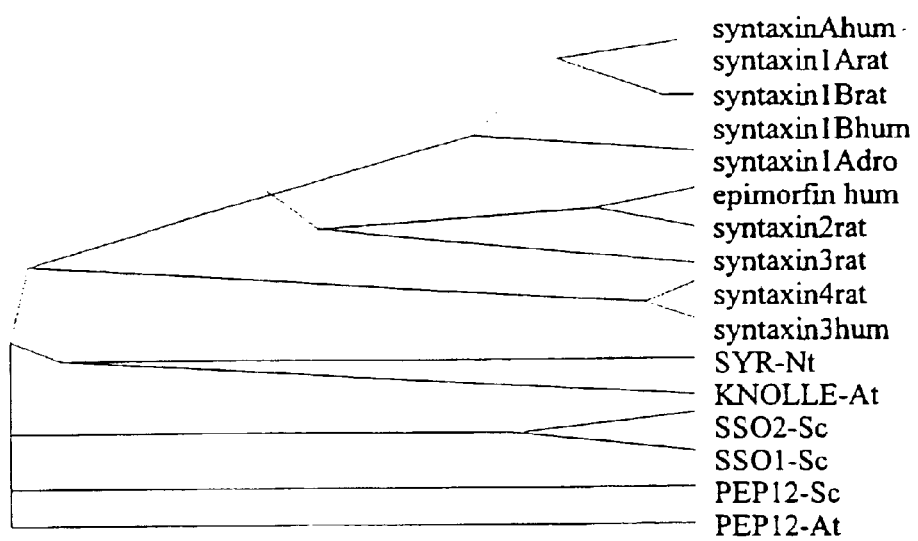

FIG. 11 shows a phylogenetic tree of some representative members of the syntaxin family.

Figure 12:
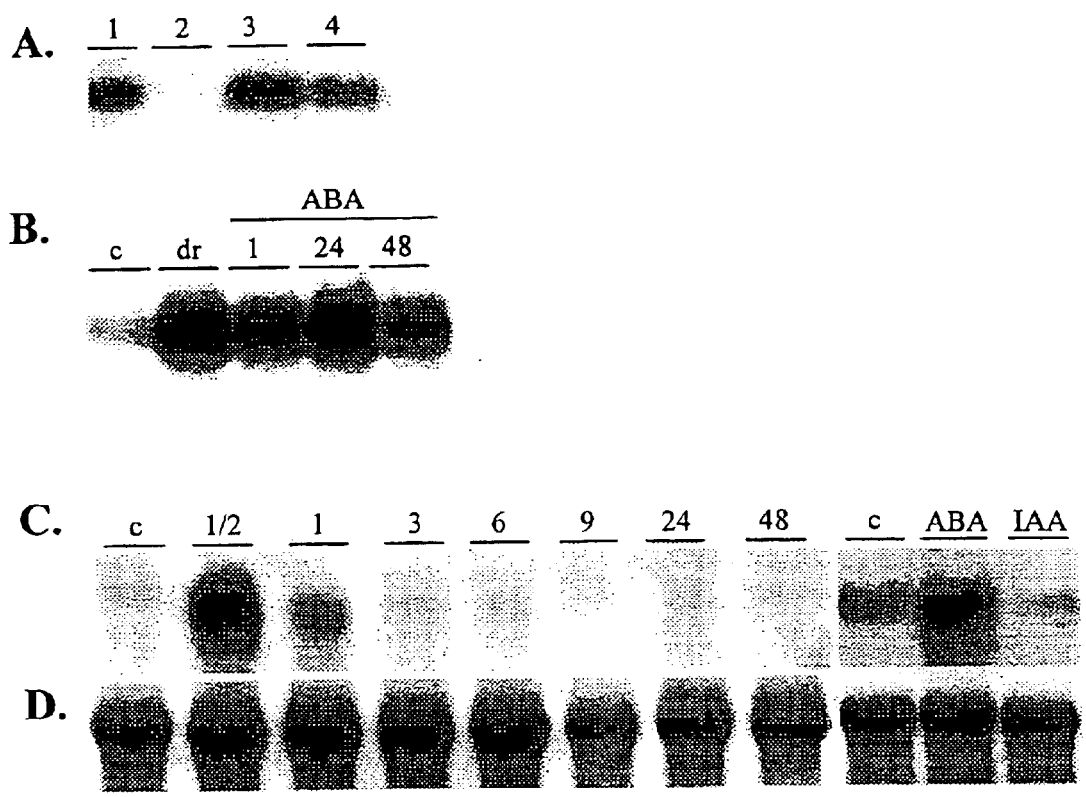

FIG. 12: shows northern analysis of SYR expression in *N. tabacum*.
A. mRNA was isolated from stems (lane 1 and 3) and leaves (lane 2 and 4). Plant growth conditions were wet (towards 100% humidity) for lane I and 2 and were in dry conditions (greenhouse conditions) for lane 3 and 4.
B. mRNA was isolated from leaves. Plants conditions were from left to right: 100% humid (control, c), drought stressed (dr) and treated with ABA for 1 h, 24 h, 48 h.
C. Total RNA was isolated from leaves. Plants were grown in highly humid conditions with from left to right: control c, and treated with ABA for 30 min (½). 1 h, 3 h, 6 h, 9 h, 24 h and 48 h, and 30 min IAA (IAA).
D. Photo of the UV illuminated EtBr stained ribosomal bands of the gels used in C.

FIG. 13A shows a photo of the oocyte voltage clamp experimental set up;

FIG. 13B shows a closeup photo of the chamber.

Figure 14:
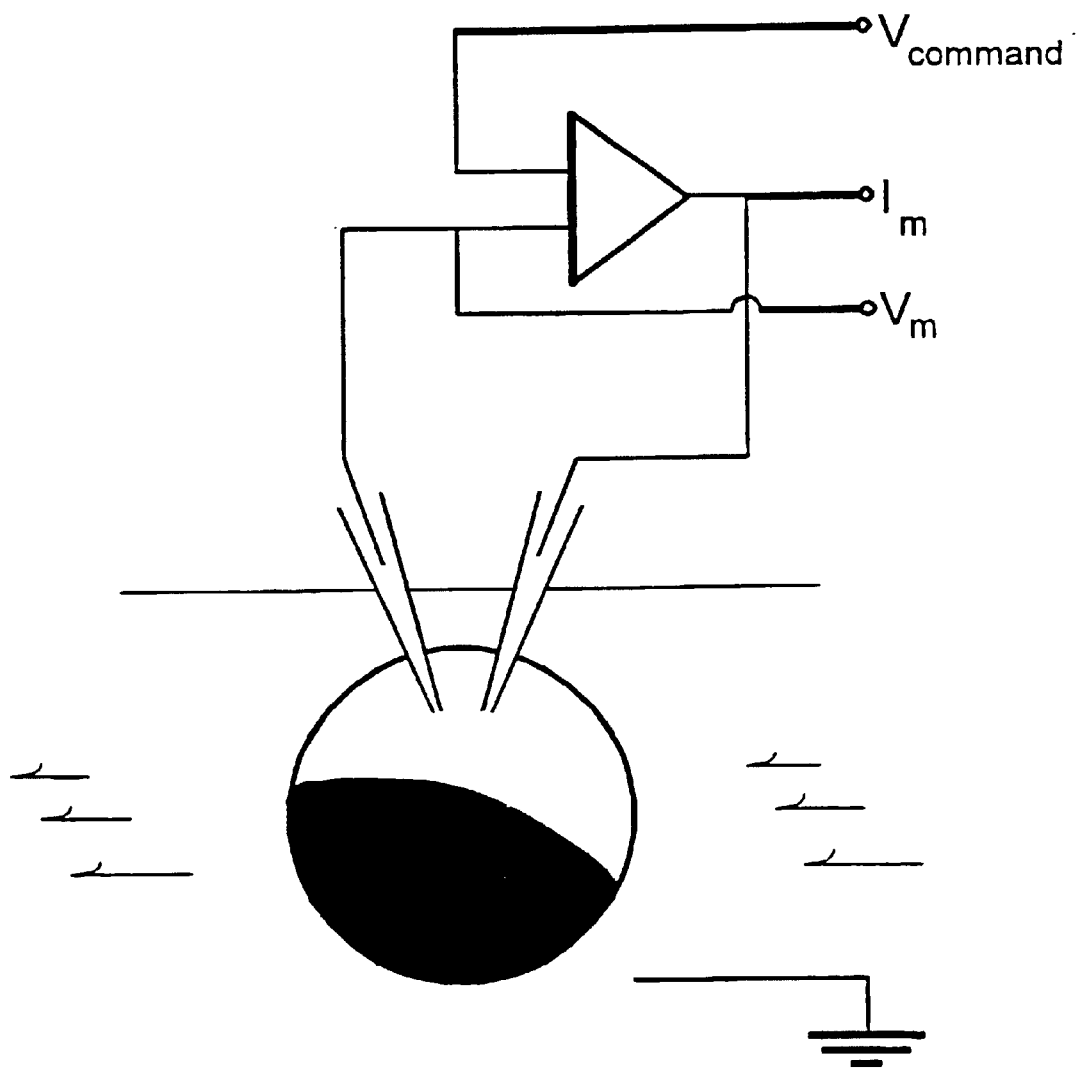

FIG. 14 is a schematic diagram of a voltage clamp circuit implemented on an oocyte membrane. $V_m$: free membrane potential; $V_{command}$: command voltage; $I_m$: current corresponding for the command voltage adjusted with the membrane voltage.

Figure 15:
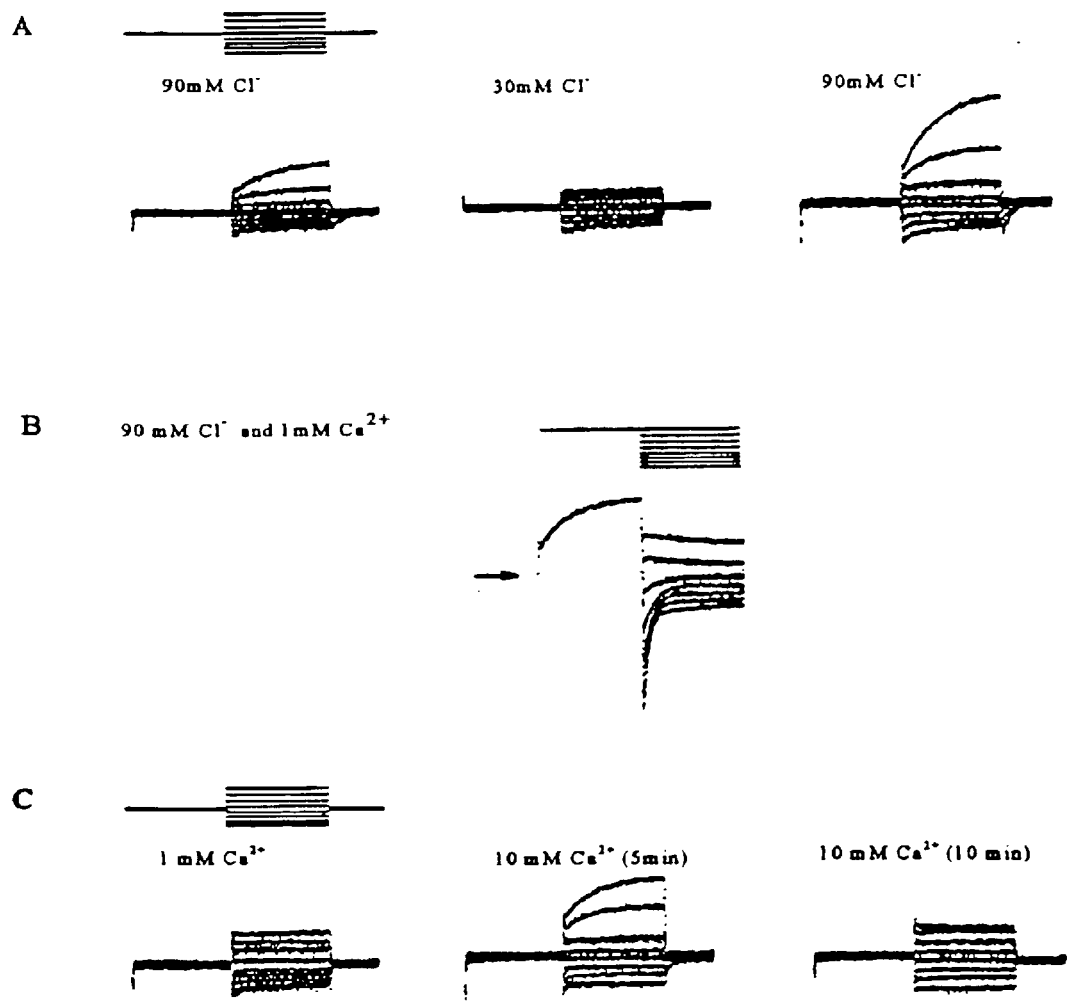

FIG. 15 shows outward rectifying oocytes currents are carried by $Cl^-$ and are $Ca^{2+}$ dependant. Each panel displays data from one oocyte: the voltage cycle protocol and corresponding clamp currents vs time.
A. Oocyte currents as recorded in 90 mM $[Cl]_o$ or 30 mM [Cl]. Voltage clamp cycles (above): prepulse, -60 V; 8 test pulses, from -180 mV to +40 mV; postpulse: -60.
B. The reversal potential of the outward rectifying currents in normal Ringer's buffer. Voltage clamp cycles (left): conditioning pulse, +50 mV; test pulses from -160 mV to +30 mV. The arrow shows where the current is inverted (between the −3 mV and −34 mV test pulse).
C. The Cl⁻ currents recorded with different $[Ca^{2+}]_o$. Voltage clamp cycle (above): prepulse −60 mV; test pulses from −180 mV to +40 mV; postpulse: −60 mV. Scale: vertical, 500 nA; horizontal, 500 ns.

Figure 16:
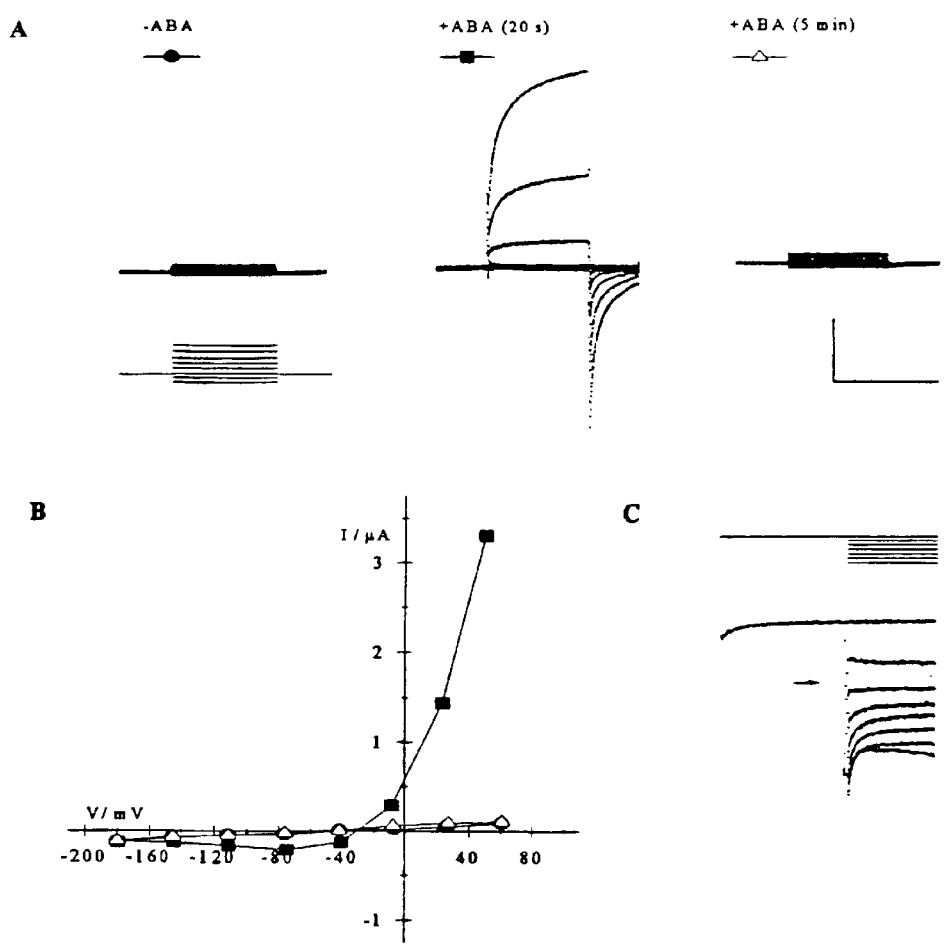

FIG. 16 shows ABA response for mRNA injected oocyte.
A. Current trajectories of a typical mRNA injected cell recorded before (circles) and during exposure to ABA after 20 s (squares) and 5 min (triangles). Voltage clamp cycles (above): prepulse and postpulse, −120 mV; 8 test pulses between −180 mV and +60 mV. Scale: vertical, 1 $\mu$A; horizontal, 1 s.
B. Steady-state current-voltage relations taken from currents at the end of the test pulses.
Symbols are cross-referenced to A.
C. The reversal potential of the outward-rectifying currents as measured for one mRNA injected oocyte during the ABA response in normal Ringer's buffer. Voltage clamp cycles (above): conditioning pulse, +20 mV; test pulses from −180 mV to +20 mV. The arrow shows where the current relaxation inverted (between the −15 mV and −35 mV test pulses). Scale: vertical, 500 nA; horizontal, 500 ms.

Figure 17:
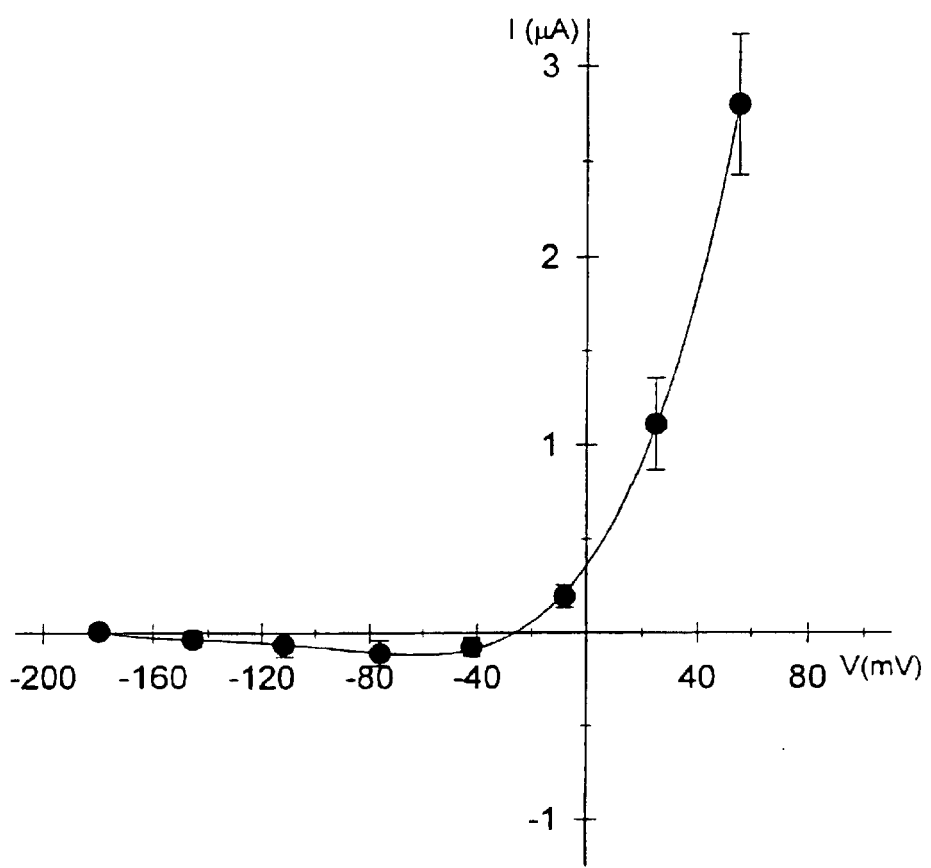

FIG. 17 shows steady-state current-voltage relations for ABA-induced currents. Steady-state currents were recorded at the end of the test voltage pulses before and during exposure of ABA. ABA-induced currents were calculated by substracting the background steady-state current (before ABA) from the response steady-state current as recorded during the first min of ABA exposure. Points are each means ±SE of the mRNA injected cells which showed an ABA response similar to that shown in FIG. 16 (n=3).

Figure 18:
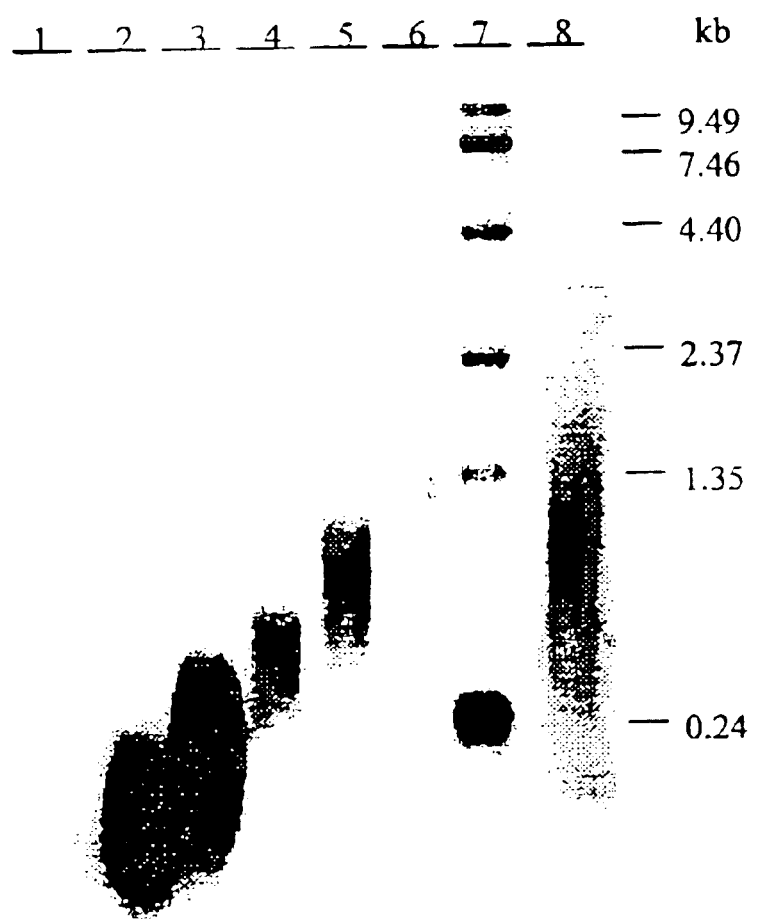

FIG. 18 shows an agarose gel representation of some fractions of the sucrose gradient and the cRNA derived from the library pool. Lane 1–6 are the sucrose gradient fractions 1–6 respectively. Lane 7 is a RNA molecular marker. Lane 8: cRNA from a pool of 2000 clones from the library.

Figure 19:
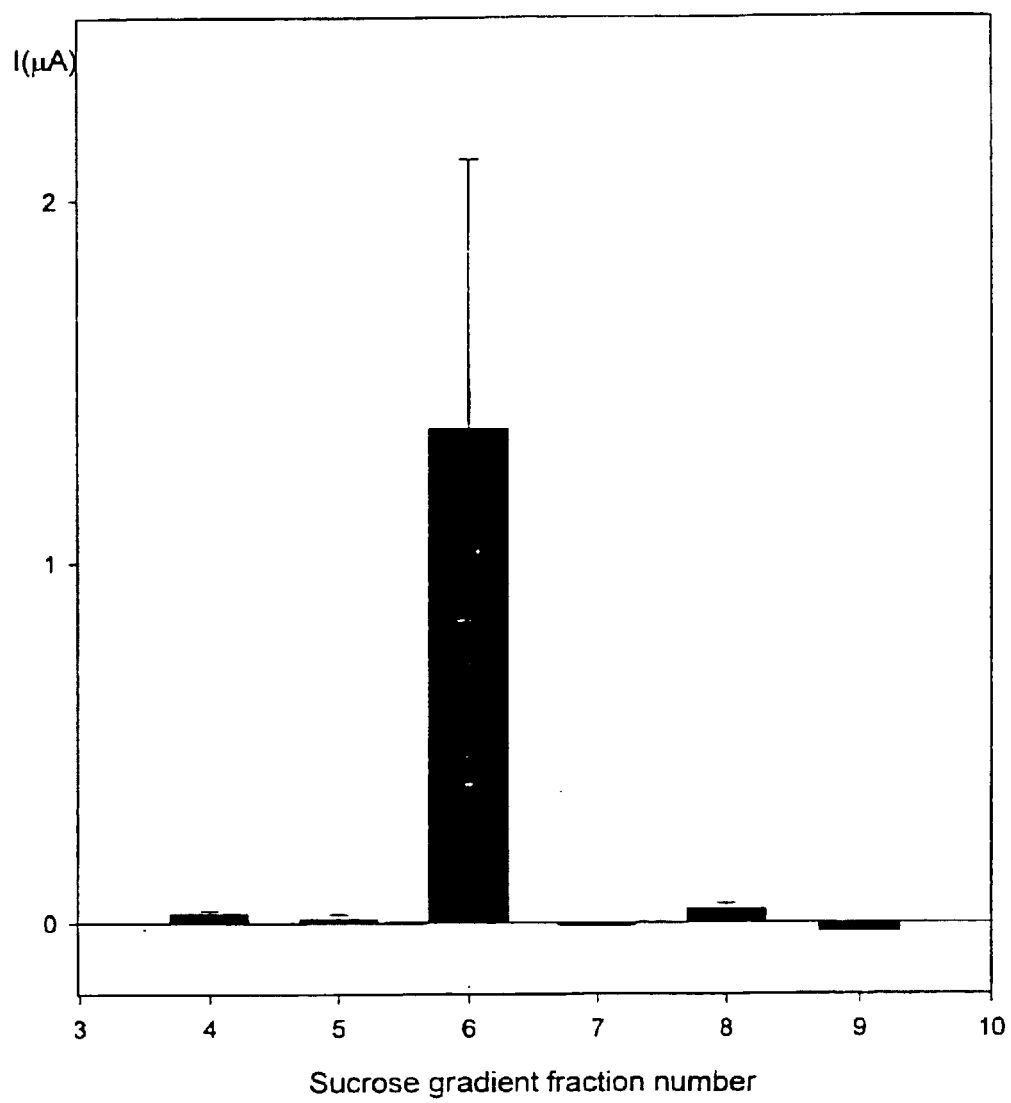

FIG. 19 shows the mean ±SE of the ABA induced steady-state current with the membrane voltage clamped at +60 mV for oocytes injected with the different mRNA pools of the sucrose gradient.

FIG. 20 shows clamp current traces before and after adding ABA of oocytes injected with cRNA from the subsequent positive pools, containing 20000, 2000, 200 or 20 transcripts. The voltage clamp protocol is shown at the top of the figure. Pre and post pulse, −120 mV8 test pulses from −180 mV to +60 mV. Scale: vertical, 500 nA; horizontal, 1 s.

Figure 21:
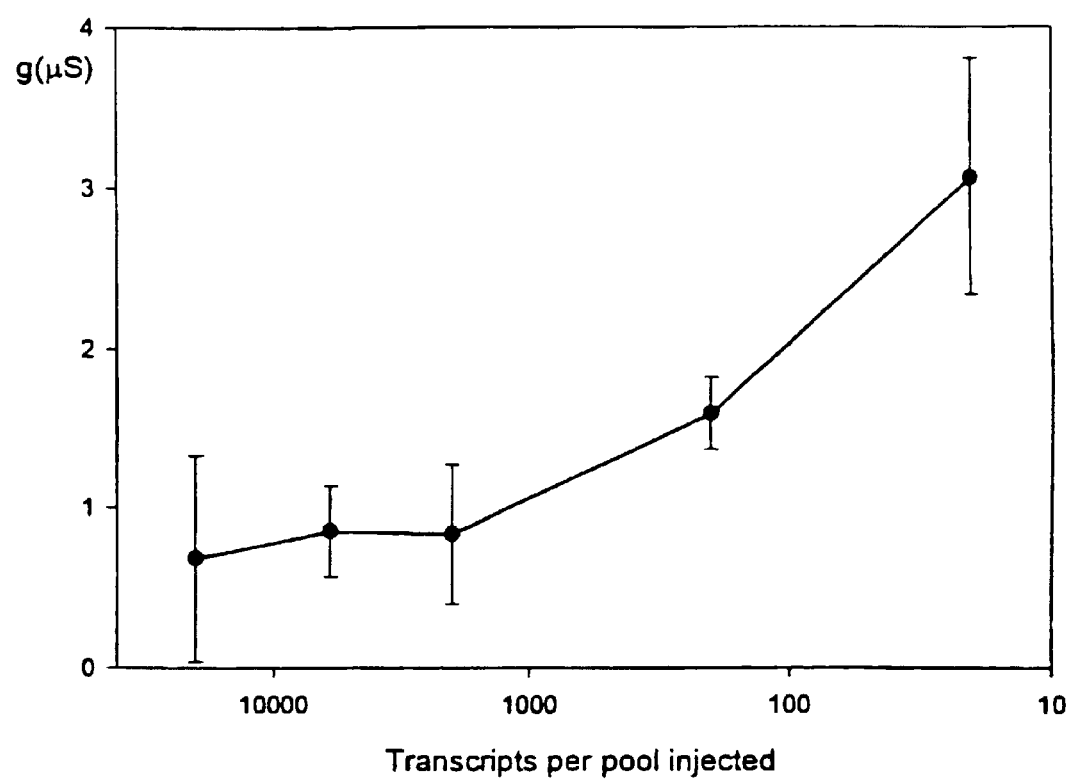

FIG. 21 shows semi logarithmic plot of the mean ±SE chord conductance as a function of the absolute amount of transcript per pool.

Figure 22:
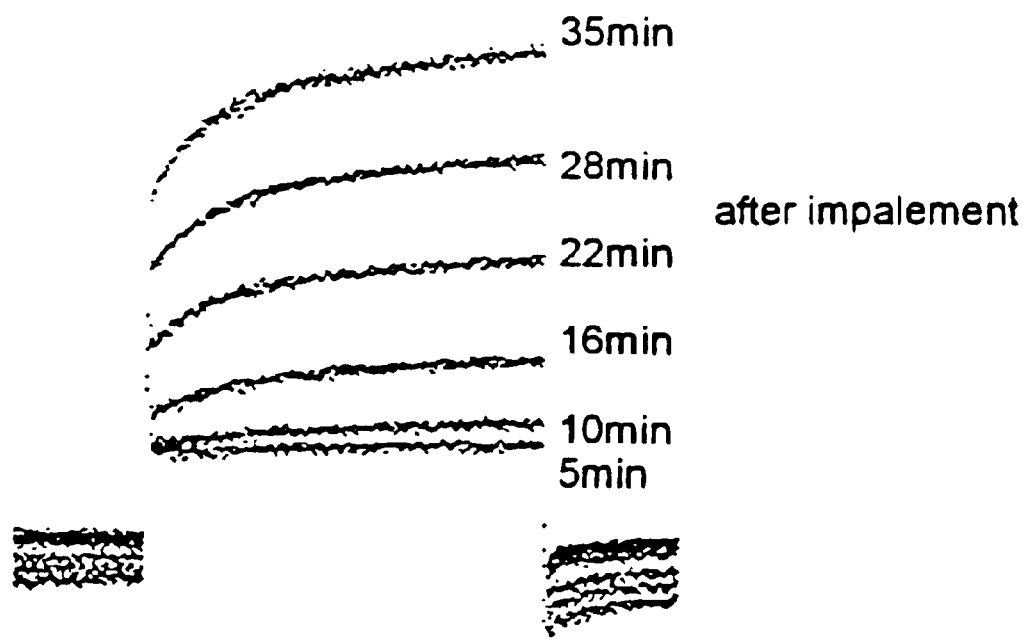

FIG. 22 shows current measured when the membrane of the oocyte expressing SYR was clamped at +60 mV. Measurements were carried out with indicated intervals after impalement of the cell. The pre and post pulse were −120 mV. Scale: vertical; 500 nA; horizontal: 500 ms.

Figure 23:
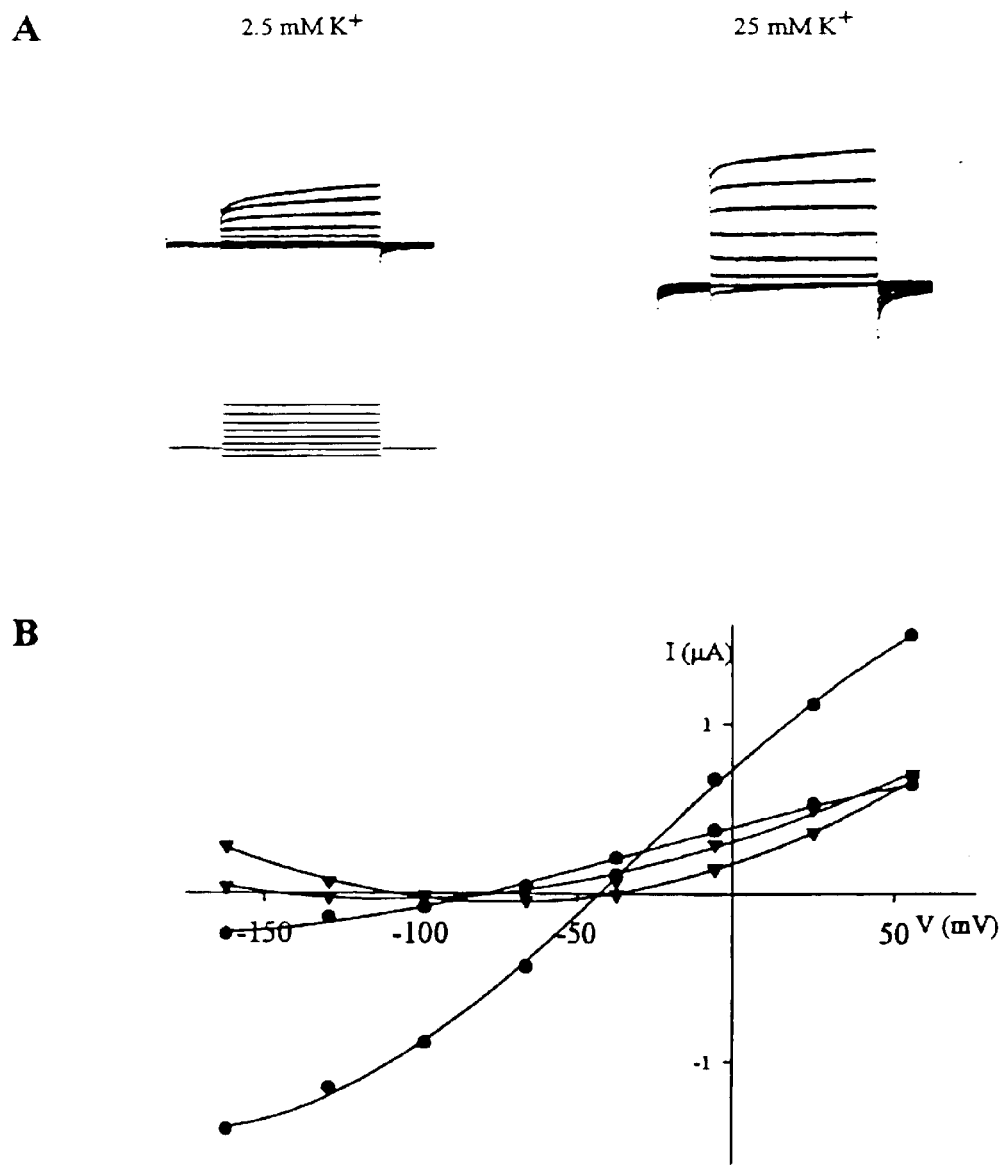

FIG. 23 shows outward rectifying currents of an oocyte expressing SYR.
A. Current traces as recorded in normal Ringer buffer with 2.5 mM K⁺ or in a modified Ringer buffer with 25 mM K⁺. under: voltage clamp protoocol: prepulse and postpulse of −20 mV, 8 test pulses, from −160 mV to +60 mV. Scale: vertical, 1 $\mu$A; horizontal, 1 s.
B. Current-voltage relationship of the instantaneous (circles) and time-dependent (triangles) components. 2.5 mM K⁺; and: 25 mM K⁺.

FIG. 24 shows tail current analysis of the outward-rectifying current from an oocyte expressing SYR in 2.5 mM K⁺ and at 25 mM K⁺. Voltage clamp cycle (under left): conditioning pulse at +50 mV; test pulses ranging from −160 mV to +30 mV. The arrow shows where the current relaxation inverted. Scale: vertical, 1 $\mu$A; horizontal, 1 s.

Figure 25:
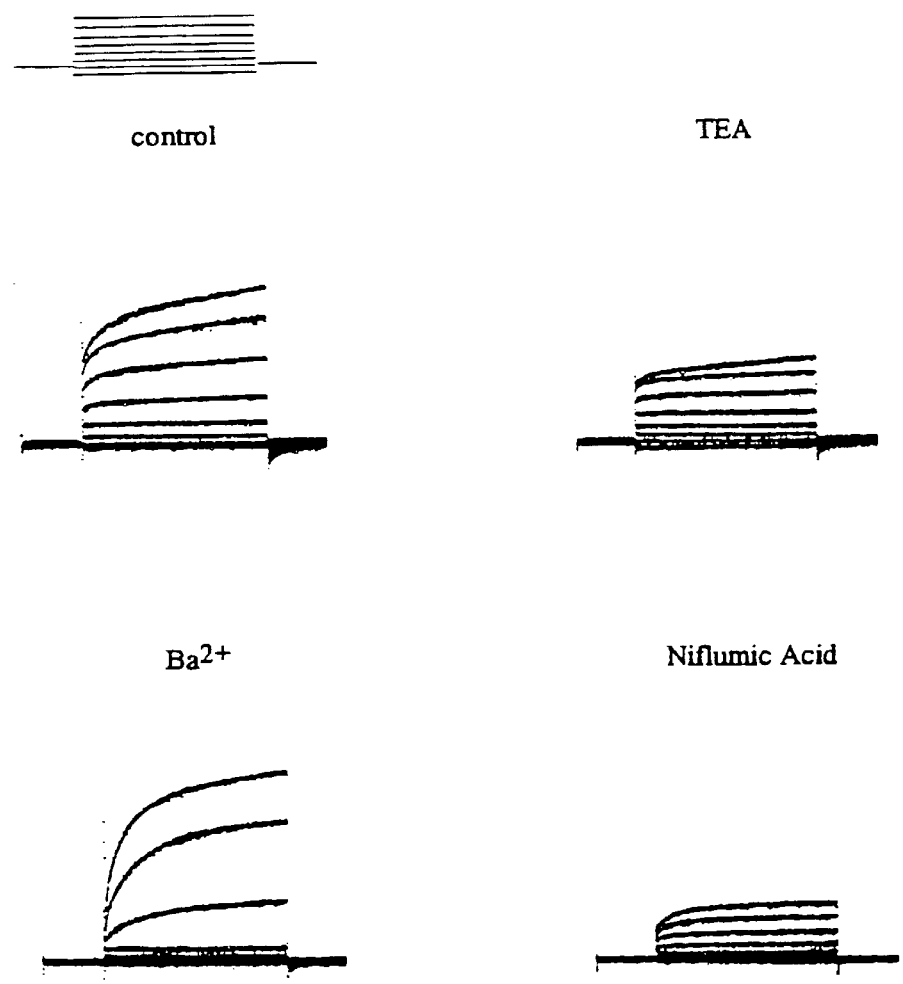

FIG. 25 shows current trajectories demonstrating the effect of various toxins, TEA, Ba²⁺, and niflumic acid in comparison with a control (no toxin). Voltage protocol: pre and Post pulse of −120 mV, 8 test pulses between −160 mV and +60 mV. Scale: vertical $\mu$A, horizontal: 1 s.

Figure 26:
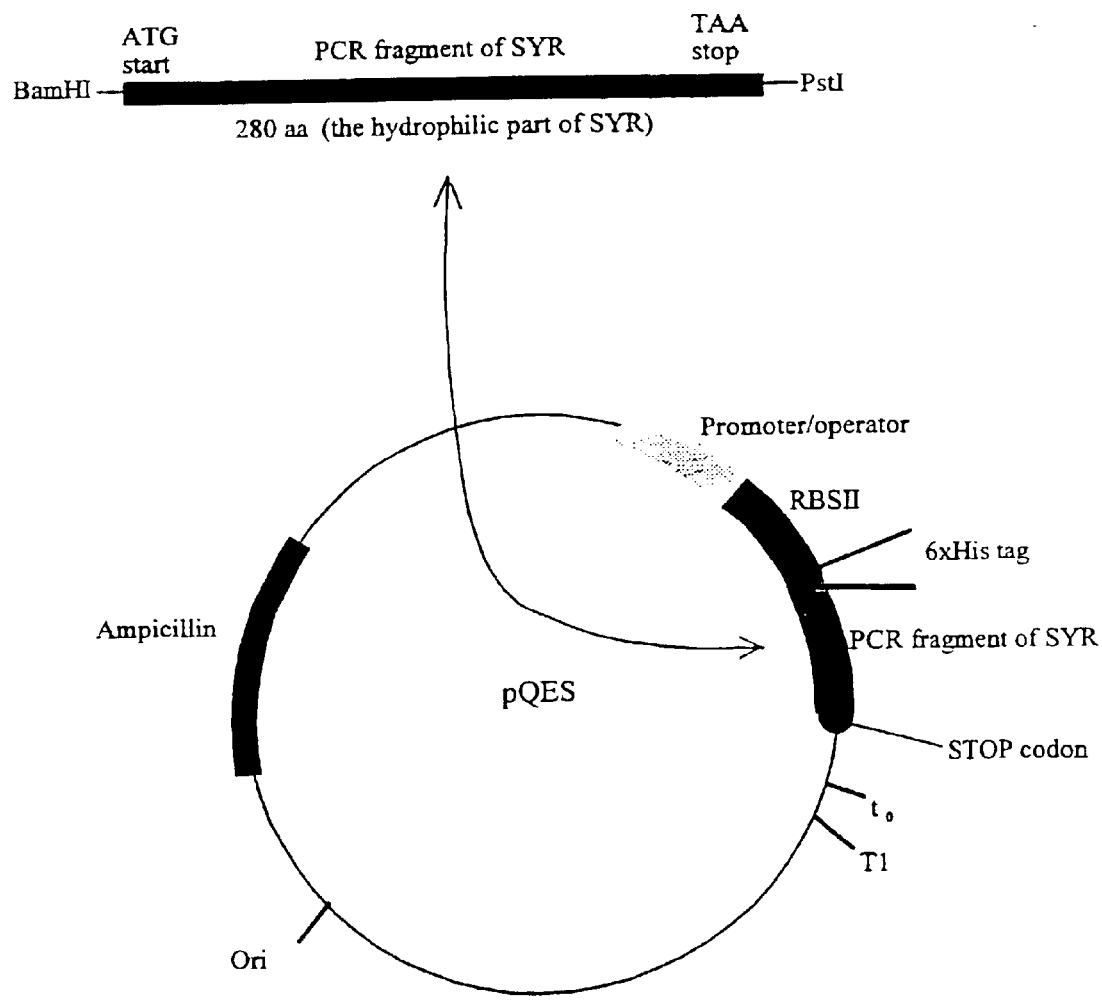

FIG. 26 shows pQES, SYR hydrophilic fragment cloned in the pQE-30 expression vector. The vector contains the ampicillin resistance gene, a strong promoter-operator element (phage T5 promoter and two lac operator sequences), a synthetic ribosomal binding site (RBS), The SYR gene preceded by 6 histidine residues in frame and followed by a STOP codon and two strong terminators (to from phage lambda and T1 from E. coli). The origin (ori) of replication is ColE1.

FIG. 27 shows sequence motifs required as template for BotN/C.
A. Cleavage site: SYR-Nt (SEQ ID NO:28); syntaxin 1A-DRO (SEQ ID NO :29); syntaxin 1A-RAT, syntaxin 1A-HUM (SEQ ID NO:30); SSO1-yeast (SEQ ID NO:3 1); SSO2-yeast (SEQ ID NO:32);
B. recognition motifs X1 and X2 of SYR: left face is mainly hydrophobic (34, 41 and 37 for X1; 175, 182 and 178 for X2); right face is mainly negative charged (35,39 and 36 for X1; 176, 180 and 177 for X2).

FIG. 28 shows current traces of the reaction of ABA on the anion current of typical guard cells of N. benthamiana under different treatment. The voltage clamp cycles (above): 8 test pulses between −230 mV and 30 mV. Left: absence of ABA, right: presence of ABA.
Scale: vertical 100 $\mu$A/cm², horizontal 2 s.
A. Control cell, no treatment
B. Cell treated with BotC
C. Cell treated with BotD.

Figure 30:
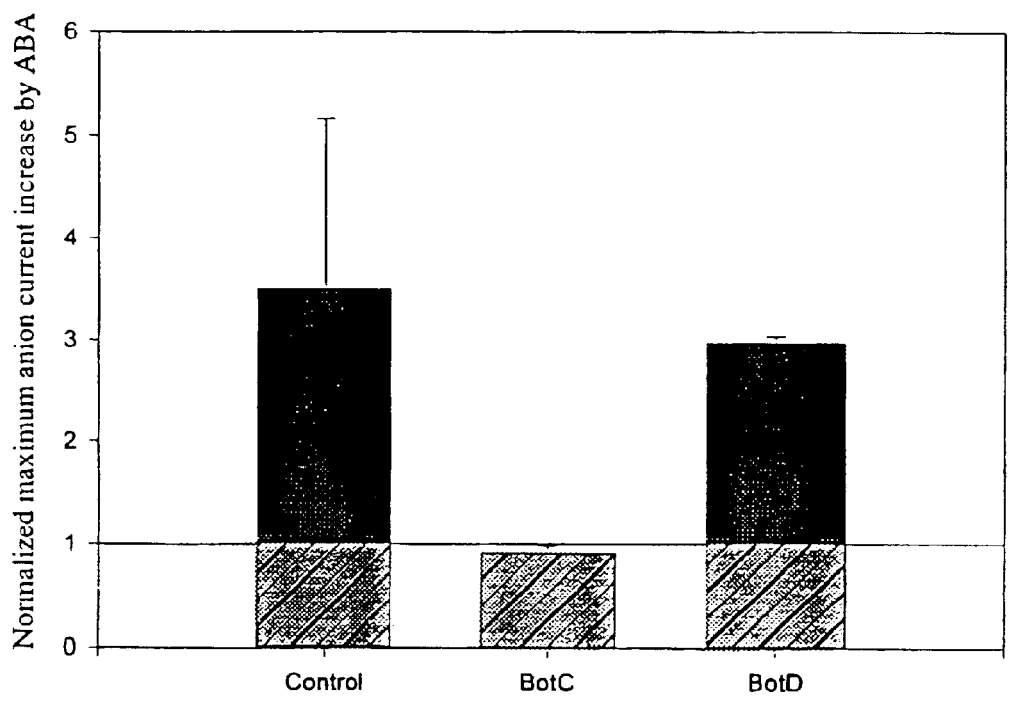

FIG. 29 shows current voltage relationship of the instantaneous (left), and steady state (right) current deducted from the current trajectories in FIG. 28 circles: absence of ABA, triangles: presence of ABA.
A. Control cell, no treatment
B. Cell treated with BotN/C
C. Cell treated with BotN/D FIG. 30 shows normalized maximum increase in instantaneous anion current. The mean is shown for 3 cells of the control cells: 6 cells of the BotN/C and 2 cells of the BotN/D treated cells. Values at −200 mV are normalized towards the amplitude of anion current before ABA was added.

Figure 32:
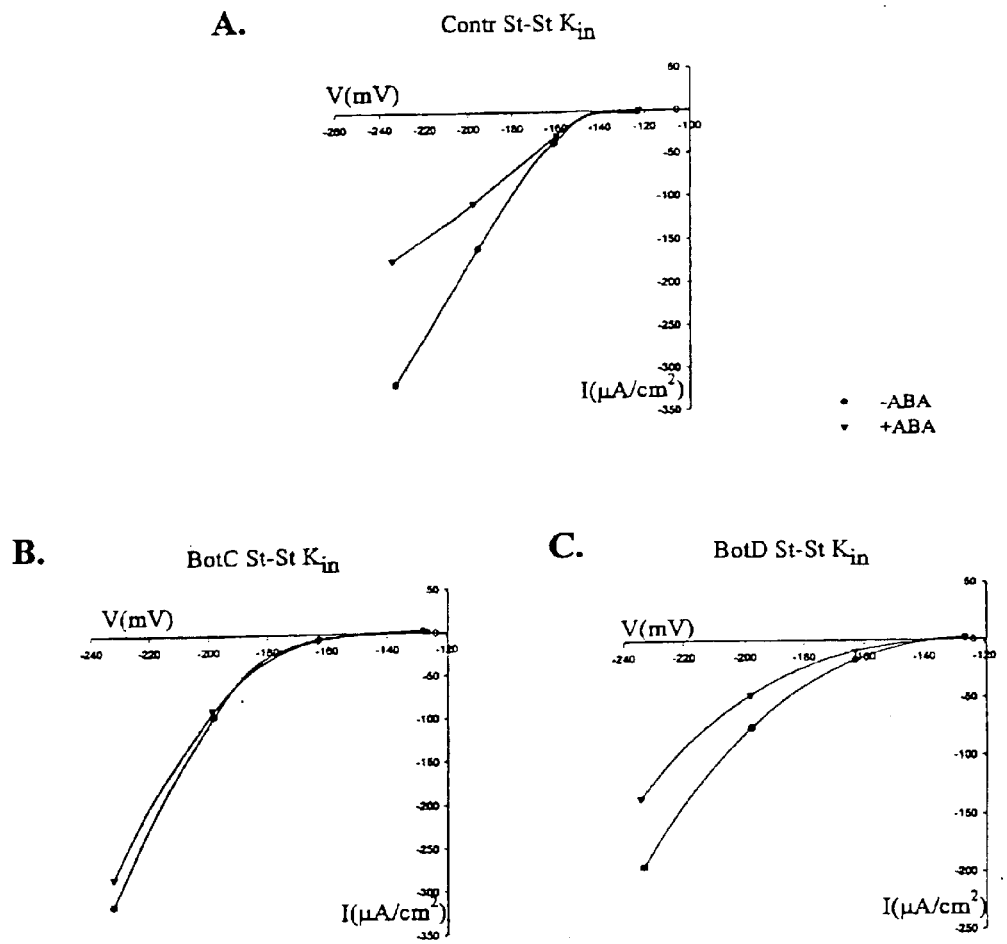
Figure 33:
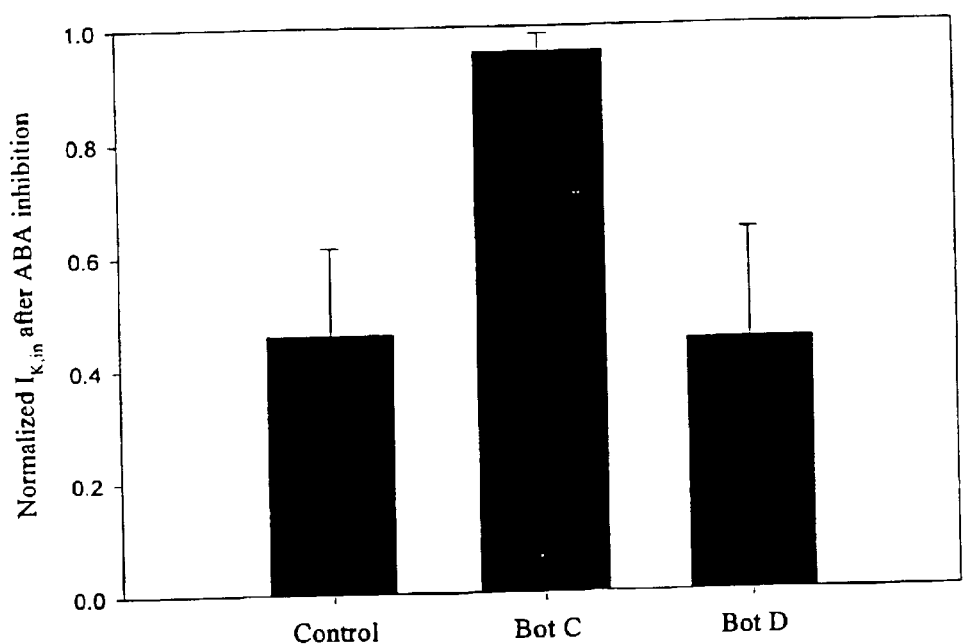

FIG. 31 shows current traces of the reaction of ABA on the $[I_K]_{in}$ of typical guard cells of N. benthamiana under different treatment. The voltage clamp cycles (above): conditioning pulse 1 s at −100 mV; 4 test pulses of 4 s between −230 mV and −130 mV. Left: absence of ABA, right: presence of ABA. Scale: vertical 100 $\mu$A/cm², horizontal 1 s.
A. Control cell, no treatment
B. Cell treated with BotC
C. Cell treated with BotD FIG. 32 shows current voltage relationship of the steady state current deducted from the current trajectories in FIG. 31 and adjusted for the leak circles: absence of ABA, triangles: presence of ABA.
A. Control cell, no treatment
B. Cell treated with BotN/C
C. Cell treated with BotN/D FIG. 33 shows ABA mediated $1_{K.in}$ values at voltage −200 mV normalized for the current value before adding ABA.

The mean ±SE is shown for 5 control cells, 4 cells treated with BotN/C, and 3 cells treated with BotN/D.

Figure 34:
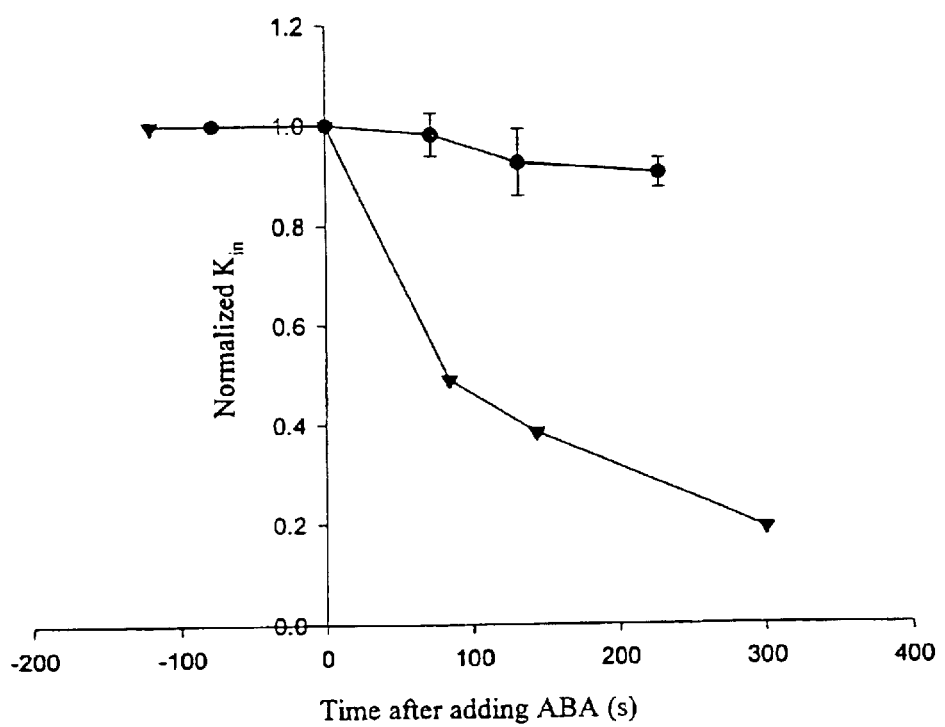

FIG. 34 shows ABA mediated $1_{K,in}$ values at voltage −200 mV normalized for the current value before adding ABA. The mean is shown for 3 BotN/C treated cells (circles), one value only was recorded as a control cell (triangles).

Figure 35:
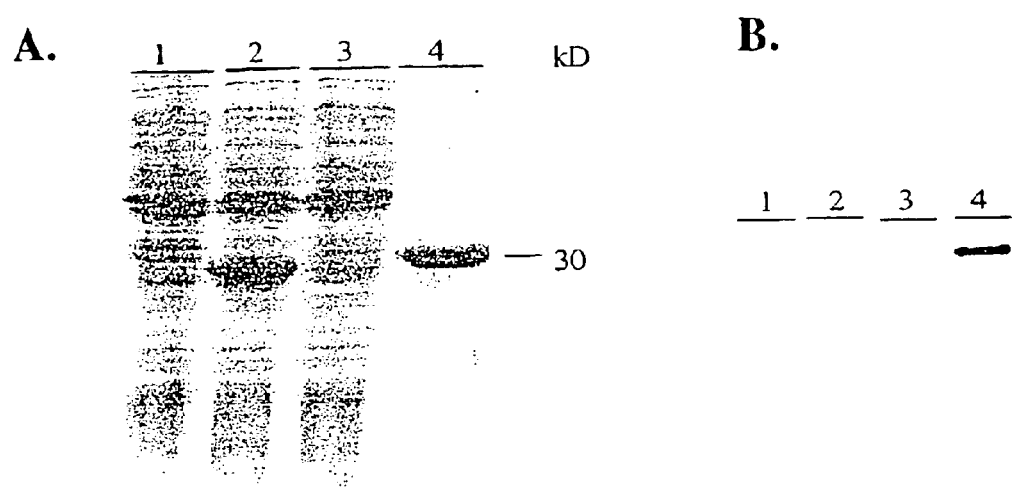

FIG. 35 shows A. Coomassie stain of a SDS PAGE.: Lane 1 and 2: total protein extractions of *E. coli* M15[pREP 14][pQES] before (lane 1) and after (lane 2) induction with IPTG. Lane 3: wash after the $Ni^{2+}$ resin binding. Lane 4: purified SP2.
B. Western blot of 5 ng (lane 1 and 3) and 50 ng (lane 2 and 4) pure peptide hybridized with pre-immune serum (lane 1 and 2) and SYR antibody (lane 3 and 4).

FIG. 36 shows A. Western hybridizations using the pre-immune (lane 1 and 2) and anti-SYR antibody serum (lane 3 and 4). Lane 1 and 3: W303-1A: lane 2 and 4: W303-1A (SYR)2.
B. Western blots of W303-1A(SYR) membrane protein extracts after treatment with botulinum toxins using anti-SYR antibody as probe. Lane 1: W303-1A(SYR) control; lane 2: W303-1A(SYR)+BotN/C; lane 3: W303-1A(SYR)+BotN/D; lane 4: molecular weight standards.

Figure 37:
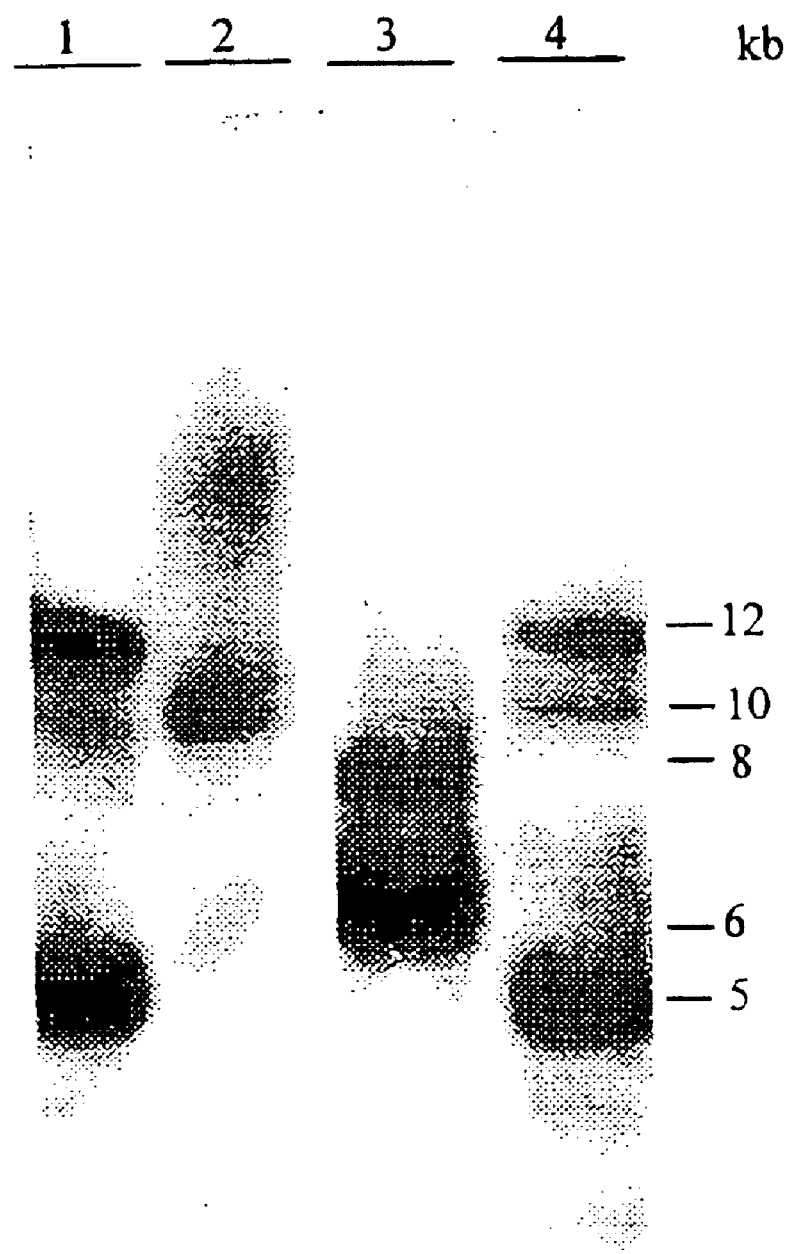

FIG. 37 shows Southern blot. DNA blotted from *N. benthamiana* (lanes 1 and 2), and from *N. tabacum* (lane 3 and 4). DNA was digested with EcoRI lanes 1 and 3), or HindIII (lanes 2 and 4).

Figure 38:

FIG. 38 shows growth of yeast strains on a galactose containing medium (A) and a galactose deficient medium (B). Three strains were used. WT: wild type *S. cerevisiae*, H440 (Aalto et al. 1993), and H440(SYR): the H440 strain expressing the SYR gene.
C. Western blot of the membrane protein extracts of the yeast strain H440. Lane 1 and 3: H440; lane 2 and 4: H440(SYR). Probes used were pre-immune serum (lane 1 and 2) and anti-SYR serum (lane 3 and 4).

Figure 39:
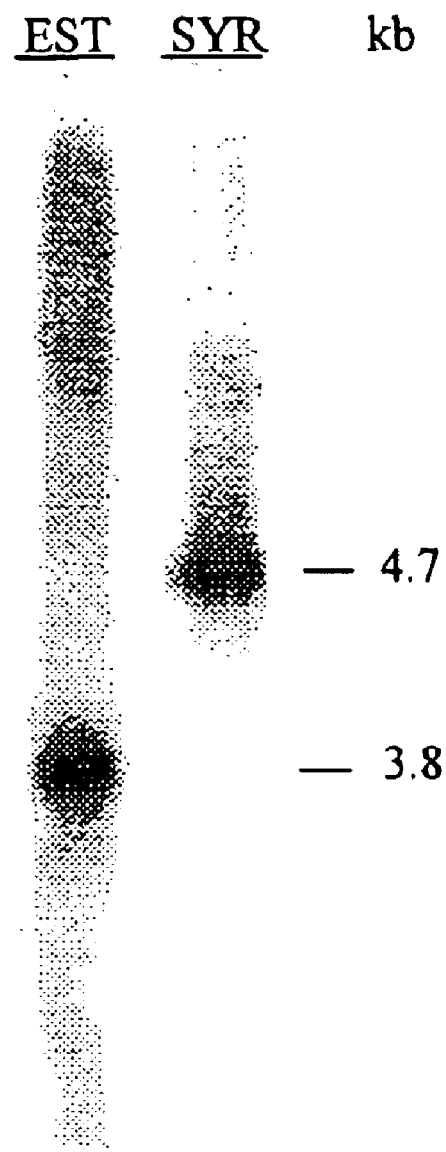

FIG. 39 shows Southern hybridization of Arabidopsis thaliana DNA. The DNA, digested with EcoRI was hybridized with the EST, P16862 (left lane) and with SYR (right lane).

Figure 41:
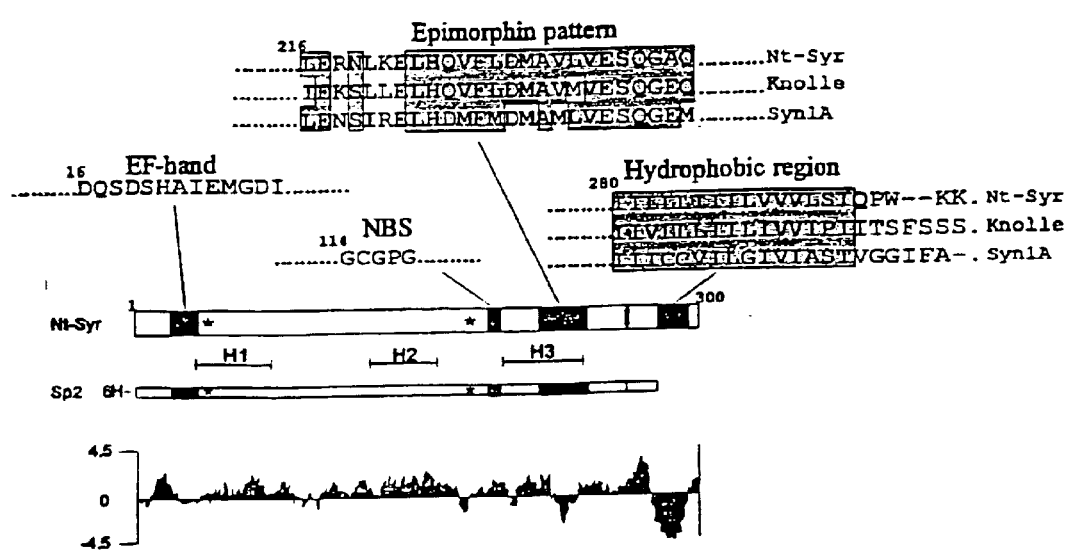

FIG. 40 (or SEQ ID NO:5) shows the antisense cDNA SYR cloned into pG3SA;

FIG. 41 shows hydrophobicity, alignment and expression analysis of the Nt-Syr protein. (A) Key features of Nt-Syr include putative Ca2+-binding (EF-hand; SEQ ID NO:33) and nucleotide-binding (NBS; SEQ ID NO:34) sites, partially conserved amphipathic X1 and X2 domains (*) for recognition and cleavage by BotN/C toxin, and three putative coiled-coil domains (H1–H3). High amino acid conservation with Knolle of *Arabidopsis thaliana* (15; SEQ ID:NOs:36 and 39) and with human Syntaxin-1A (Syn1A; SEQ ID NOs:37 and 40) (3) is found in the epimorphin pattern domain (=H3) (Nt-Syr=SEQ ID NO:35; Knolle= SEQ ID NO:36; Syn1A=SEQ ID NO:37) and the C-terminal hydrophobic tail (Nt-Syr=SEQ ID NO:38; Knolle=SEQ ID NO:39; Syn1A=SEQ ID NO:40). The truncated protein (Sp2), corresponding to the first 279 amino acids was N-His-tagged and used for generating antibodies.

FIG. 42 shows that Neurotoxin BotN/C but not BotN/D targets Nt-Syr and blocks ion channel response to ABA in guard cells of Nicotiana. (A) Microsomal protein fractions were isolated from Nicotiana leaves, pretreated either with or without 1 mM ATP, and incubated with BotN/C and BotN/D.
Proteins were separated by SDS-PAGE and assayed by Western blot analysis using the anti-Sp2 antiserum. Loading, 6 g protein per lane. (B) Voltage clamp analysis of Cl− channel response to 20 M ABA in guard cells with and without BotN/C. Voltage clamp steps (above): conditioning voltage (5 s), +30 mV (not shown); test voltages (6 cycles), −160 mV to +30 mV. Measurements carried out in 15 mM TEA-Cl and 15 mM CsCl to eliminate K+ channel currents. Current traces are from one guard cell loaded with 0.1 M BotN/C before and 8 min after adding 20 M ABA. Data from a second cell in ABA are shown for comparison. No significant difference in current characteristics were observed in the absence of ABA between non-loaded cells and cells loaded with either toxin. Scale: vertical 100 A cm-2, horizontal 2 s. (C) Means +/−SE of the ABA response of the Cl− current (ICl, top) and inward-rectifying K+ current (IK,in, bottom) from non-loaded (contr), BotN/C- and BotN/D-loaded guard cells (n 5). Data recorded at −200 mV and normalized to the corresponding measurements taken before ABA treatments. (D) Current-voltage relationship of the instantaneous currents from (B) cross-referenced by symbol.

Figure 43:
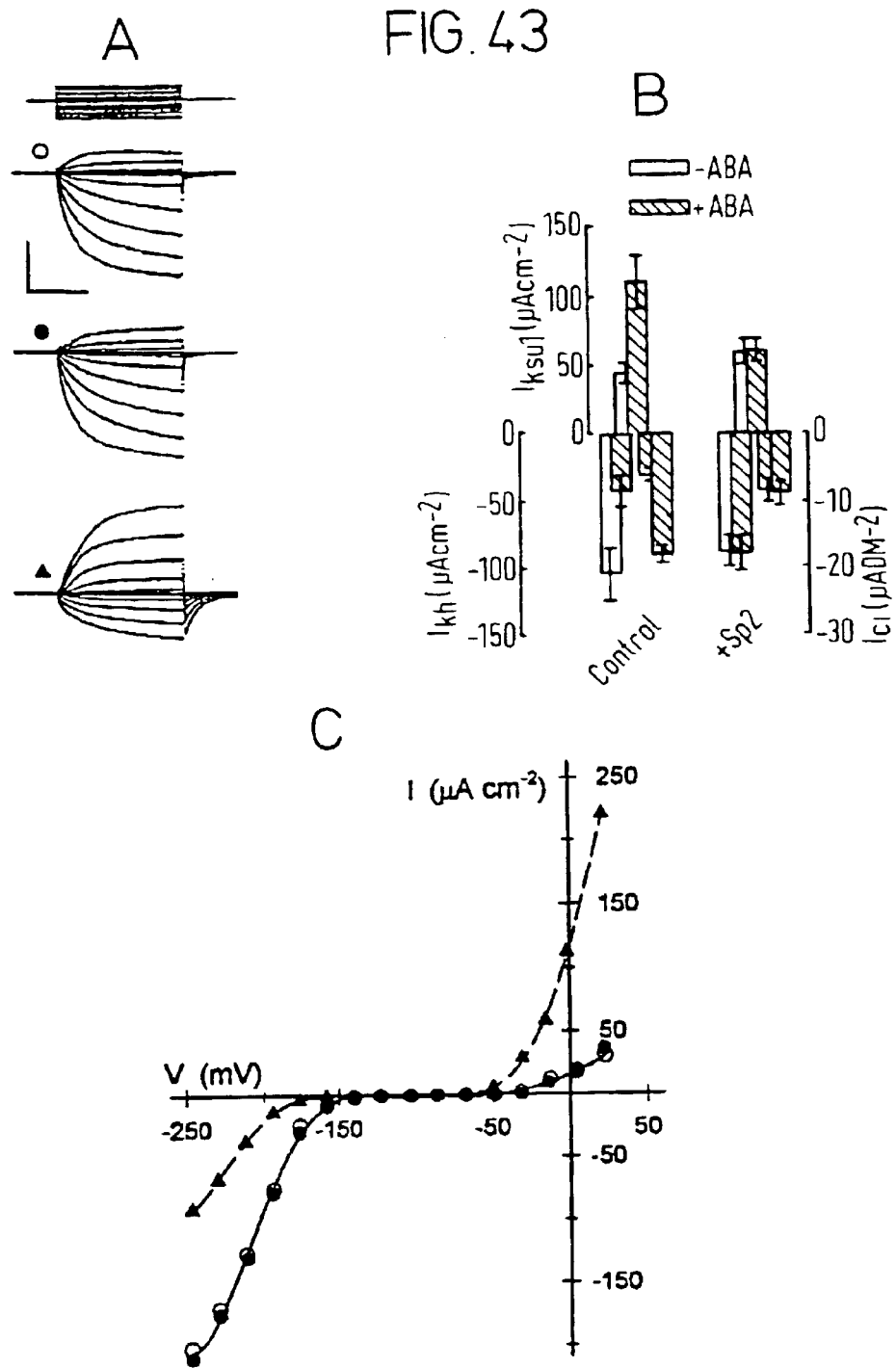

FIG. 43 shows how truncated Nt-Syr protein (Sp2) blocks ion channel response to ABA in Nicotiana guard cells. (A) Voltage clamp analysis of K+ channel response to 20 M ABA in guard cells. Voltage clamp steps (above): conditioning voltage, −100 mV; test voltages (16 cycles), −250 mV to +30 mV; tailing voltage, −100 mV. Measurements carried out in 10 mM KCl. Current traces are from one guard cell loaded with 20 M Sp2 before and 10 min after adding 20 M ABA. Data from a second cell in ABA are shown for comparison. No significant difference in current characteristics were observed in the absence of ABA between non-loaded cells and cells loaded with the Sp2 protein. Scale: vertical 100 A cm-2, horizontal 1 s. (B) Means +/−SE of measurements before and 10 min after adding ABA in non-loaded (Control) and Sp2 loaded cells. Data are for the inward-rectifying (IK,in, open bars down) and outward-rectifying (IK,out, open bars up) K+ currents and for the Cl+ current (ICl, shaded bars down) before and 10 min after ABA additions. Currents taken at steady-state recorded at −200 mV (IK,in), +30 mV (IK,out), and −100 mV (ICl). The steady state amplitude at a particular voltage for the three currents is displayed: IK,in (−200 mV, bars pointing down), IK,out(bars pointing up) and Icl (grey bars). (C) Current-voltage relationship of the steady state currents from panel A. Current values are the result of the subtraction of the leak instantaneous current from the total steady state current. Symbols are cross referenced in A.

STRATEGY FOR EXPRESSION CLONING OF AN ABSCISIC ACID SIGNALLING COMPONENT

In order to isolate an abscisic acid signalling component protein, the heterologous *Xenopus laevis* oocyte expression system was chosen. The rational for this was three-fold. (1) No substantive data is available for the receptor molecular structure or for the receptor DNA or protein sequence and no consensus exists over the receptor's location (membrane bound or cytosolic). (2) There is convincing evidence that $Ca^{2+}$ acts as a second messenger in the ABA signal pathway and the hormone should therefore be able to induce oocyte Cl− currents when ABA perception proteins are expressed in oocytes. Coupling of the ABA signal transduction and endogenous $Ca^{2+}$ dependent Cl− channels can be at any step along the pathway. (3) Expression of plant membrane proteins into the Xenopus oocytes has been repeated successfully. We used a strategy similar to the one described by Julius et al. (1988) Science 241:558–564 with some modifications. Initially this strategy requires injection of oocytes with enriched poly(A)+ mRNA purified out of young *Nic-*

*otiana tabacum* leaves. Screening is carried out by conventional electrophysiological, assaying for activation of the Xenopus $Ca^{2+}$-dependent $Cl^-$ channels (FIG. 2A). The specificity of the response is verified using weak acids such as potassium acetate as a negative control. Other controls may be carried out to verify the mRNA specificity of the ABA response using uninjected and water injected oocytes.

Once a response of the oocyte $Cl^-$ channels to ABA is confirmed, experiments can be directed towards isolating the active transcript. A sucrose gradient may be used to divide the mRNA into several fractions by size, and each fraction may be individually injected. Fraction(s) giving a positive ABA response(s) are then be used as a template for constructing a cDNA library. For purposes of expression analysis, the cDNA is cloned unidirectionally in an expression vector pSPORT where the insert is flanked by promoters for the RNA polymerases T7 and SP6. After plasmid DNA preparation and linearization, cDNA templates derived from subfractions of the pool of clones are then be transcribed in vitro with the T7 RNA polymerase, and the RNA capped with an mGpppG molecule within this synthesis step to produce functional cRNA copies of the cDNA inserts. Xenopus oocytes are injected with this cRNA and assayed for $Cl^-$ channel activation in response to ABA as before. In this way, the pool of cDNA clones giving a positive response would always include the minimum complement necessary for full functioning of ABA perception. This combination can be progressively subdivided into smaller pools (sib-selection) until the smallest positive fraction is obtained (FIG. 2B).

Molecular cloning and biochemical approaches so far have not yielded either a protein or a gene coding for a possible ABA receptor. The main difficulties with screening for an ABA receptor are suggested by the following: From physiological analysis, there is reason to believe that multiple ABA receptors may exist, each serving a different function. The ABA signal is evidently directed to different targets at different molecular levels. On one hand, ABA mediates rapid physiological regulation in cell homeostasis, including the control of ion transport proteins at the guard cell membrane that lead to stomatal closure. On the other hand, ABA evokes a number of slower responses at transcriptional and translational level, leading to alterations in expression of ABA responsive genes that are necessary for development and vegetative stress tolerance. There is little consensus about the cellular location (cytosolic or membrane attached) of the ABA receptor(s), even in the case of homeostatic transport control in stomatal guard cell. Moreover, different cells react with divergent responses to elevated levels of ABA, for instance mesophyll cells versus guard cells. While to an extend these various responses to ABA may depend on differences in the elements coupling each response, the findings also suggest the existence of multiple ABA receptors and make it difficult to predict their cellular location.

In order to clone an ABA signalling component, we explored another technique, making use of an expression-cloning strategy with *Xenopus laevis* oocytes. An advantage of using this approach to clone an ABA signalling component lies in the fact that it is not necessary to anticipate its molecular structure. One concert, was that the ability to couple signalling components to oocyte signal pathways had never demonstrated for plants before. Whilst not wishing to be bound by any theory we believe the ABA stimulus is superimposed onto a Xenopus oocyte signalling pathway because of the common second messenger, cytosolic-free $Ca^{2+}$ concentration.

The first step was to verify the $Ca^{2+}$-dependency of the $Cl^-$ channels from *Xenopus laevis* oocytes. Thereafter before cloning an ABA signalling component by heterologous expression we analysed the efficacy of the oocytes to couple the expressed *Nicotiana tabacum* mRNA transcripts with its endogenous channels via $Ca^{2+}$ by measuring the $Cl^-$ currents in response to ABA.

*Xenopus laevis* Oocytes used as an Heterologous Expression System *Xenopus laevis* and its Oocytes

*Xenopus laevis* is a clawed toad with a South African origin. Oogenesis in Xenopus is a continuous, asynchronous process and oocytes in all stages of development are present in the ovary at all times during the adult life of a female animal. Production of fully grown immature oocytes (stage VI, see below) takes 5 to 7 weeks. Oocyte development is divided into six stages. Stage I consists of small (50 μm–100 μm) colourless oocytes whose cytoplasm is transparent. Their large nuclei and mitochondrial masses are clearly visible in the intact oocyte. Stage II oocytes range up to 450 μm in diameter, and appear white and opaque. Stage I and II are both previtellogenic. Pigment and yolk accumulation (vitellogenesis) begins during stage III. Vitellogenesis continues through stage IV (600 μm–1000 μm), the oocytes grow rapidly, and the animal (brown) and vegetal (yellow) hemispheres become differentiated. By stage V (1000 μm–1200 μm) the oocytes have nearly reached their maximum size and yolk accumulation gradually ceases. Stage VI oocytes are characterized by the appearance of an essentially unpigmented equatorial band. They range size from 1200 μm–1300 μm, are postvitellogenic and ready for ovulation and maturation.

The fully grown oocyte (stage VI) is surrounded by the following layers (beginning with the innermost). The cell is contiguously surrounded by a vitelline membrane, which is a non-cellular fibrous layer. Above, there is a layer of follicle cells. These cells are connected with the oocyte via gap junctions, which allow free passage of molecules up to 1 kD and provide electrical connection. The teca, surrounding the follicle cells, is a connective tissue layer in which smooth muscle cells, nerve fibres, and capillaries are embedded. Finally outermost is a layer of epithelial cells that form a continuation of the ovary wall. All outer layers, except for the vitelline membrane, are generally referred to as 'follicular layers' and can be enzymatically removed with collagenase.

Second Messengers and Electrical Properties of the *Xenopus laevis* Oocytes $Ca^{2+}$ Signalling in Oocytes $Ca^{2+}$ mediated signal transduction pathways including those mediated via G-protein and inositol-1,4,5-triphosphate ($IP_3$) synthesis, have been well studied in oocytes by analysing oocyte fertilization and by introducing novel receptors. A wave of calcium release and membrane depolarization accompanies Xenopus oocyte fertilization and this event is thought to be triggered by IP3. Injections of $IP_3$ have been shown to induce intracellular calcium release in mature Xenopus oocytes. Cytosolic-free $Ca^{2+}$ concentration ($[Ca^{2+}]_i$) has an effect on current activity at the membrane, notably of $Ca^{2+}$-dependent $Cl^-$ channels (see below).

Oocyte $Ca^{2+}$-dependent $Cl^-$ Channels.

In the early 1980's electrophysiologists described a voltage-activated, $Ca^{2+}$-dependent $Cl^-$ current ($I_{Cl(Ca)}$) in the membrane of Xenopus oocytes. Upon depolarization of the oocyte membrane from a holding potential of −120 mV to voltages more positive then −20 mV, a transient outward current was elicited. The amplitude of the outward current was very variable among oocytes, in most oocytes it was not detectable in normal physiological conditions, while in some occasions its peak size was in the range of 100 nA. The current was dependent on external Cl⁻, but not on K⁺ or Na⁺ and had a reversal potential around −25 mV to −30 mV, this value being close to the equilibrium potential of Cl⁻ ($E_{Cl}$). Moreover the current was inert to typical K⁺ channel blockers such as tetraethyl ammonium (TEA) but was abolished by niflumic acid, a Cl⁻ channel blocker. These results led to the conclusion that this outward current was mainly carried by an influx of Cl⁻ ions into the cell. [Note that outward-rectifying current underlies efflux of positively charged cations or influx of negatively charged anions. Inward-going current is caused by influx of cations or efflux of anions].

The $Ca^{2+}$-dependency was initially determined by ion substitution and by changing external $Ca^{2+}$ concentrations. Replacement of external $Ca^{2+}$ by $Mg^{2+}$ or $Sr^{2+}$ eliminated the current. By contrast, increasing the external $Ca^{2+}$ concentration ($[Ca^{2+}]_o$) increased the amplitude of the outward current.

More recently, it has become clear that there exist two $Ca^{2+}$-activated Cl⁻ currents with different kinetics, each consisting of two current components. First, it was found $IP_3$ injections elicited a rapidly stimulated and transient outward Cl⁻ current ($I_{Cl-1}$) upon depolarization of the membrane potential. The maximum current (2–4 μA) was reached after 30 s and declined nearly to the baseline in approximately 1.5 min. This early induced current had a reversal potential close to $E_{Cl}$, and showed two kinetic components. One component was an instantaneous current with a linear current-voltage (IV) relationship. The second component comprised a time-dependent current, that rose more slowly with a halftime of 250 ms at 20 mV. The second current, $I_{Cl-2}$ developed slowly with a half-maximal response of about 3 min after $IP_3$ injection to a maximum peak of 1–2 μA and was stable for at least 15 min. $I_{Cl-2}$ also had a reversal potential close to $E_{Cl}$ and similarly consisted of two components: a time-independent $I_{Cl-21}$ and time-dependent $I_{Cl-2D}$ component. The current-voltage relationship of the instantaneous current $I_{Cl-21}$ was linear while for $I_{Cl-2D}$ the current-voltage relationship was strongly inward-rectifying.

The Cl⁻ currents $I_{Cl-1}$, and $I_{Cl-2}$ are $Ca^{2+}$-activated because IP3 induction of both currents can be abolished when the cells were injected with the $Ca^{1+}$ chelator BAPTA. The two currents depend on $Ca^{2+}$ from different sources. $I_{Cl-1}$ was dependent on $Ca^{2+}$ released from internal stores and $Ca^{2+}$ influx. $I_{Cl-2D}$ however, was dependent on external $Ca^{2+}$ influx, because when external $Ca^{2+}$ was either depleted or prevented from entering the cell (by adding $Ca^{2+}$ channel blockers such as $Mn^{2+}$), the current $I_{Cl-2D}$ was eliminated. Under the same conditions $I_{Cl-1}$ remained intact.

Other Oocyte Channels

As suggested above, Xenopits oocytes possess voltage-gated $Ca^{2+}$ channels in their membranes that might be expected to contribute $Ca^{2+}$ influx to activate Cl⁻ currents. These $Ca^{2+}$ channels were permeable for other divalent cations. 40 mM external $Ba^{2+}$ was used to eliminate the interference of Cl⁻ currents, as they are not activated by changing internal $Ba^{2+}$ concentrations. With 40 mM external $Ba^{2+}$, an inward current was detected when the membrane was depolarized at voltages more positive then −30 mV. The current was suppressed by typical $Ca^{2+}$ channel blockers such as $Co^{2+}$ and $Cd^2+$. The results suggest that the observed current was carried by $Ba^{2+}$ through a voltage-dependent $Ca^{2+}$ channel. Under the assumption that the permeabilities of $Ba^{2+}$ and $Ca^{2+}$ were similar, the $Ca^{2+}$ current was calculated to be 1 nA and therefore below the limit of resolution in physiological conditions (2 mM external $[Ca^{2+}]_o$).

When a $Ca^{2+}$ channel blocker is applied to eliminate background Cl⁻ currents, a small (30–40 nA) outward-rectifying K⁺ current is observed, indicating the presence of a $Ca^{2+}$- insensitive K⁺ channel. The reversal potential of this current was affected by external K⁺ concentrations and followed the equilibrium potential of K⁺, indicating that this current is carried mainly by K⁺ ions. The current is sensitive to a typical potassium channel blocker TEA (tetraethylammonium).

One final current, carried by Na⁺ is known in these cells. Upon long depolarization (minutes) of the cell membrane, a voltage-activating Na⁺ channel is opened. The biological function of these channels in oocytes is not clear. It is accepted that the Na⁺ repolarising current may play a role in preventing excessive membrane depolarization and in providing a balance of inward and outward currents during maturation and fertilization of the oocytes. They may be the precursors for the channels found in fertilized eggs.

In conclusion, detail analysis of oocytes has revealed a number of currents with typical characteristics in voltage-dependency and [intra- and extracellular] $Ca^{2+}$-dependency. All currents are identifiable by ion selectivity and kinetic properties.

Expression and Cloning of Mammalian Receptors in *Xenopus laevis* Oocytes

Efficiency and Accuracy of Heterologous Expression

*Xenopus laevis* oocytes have been physiologically and electrophysiologically well characterized and have been repeatedly used to express heterologous mammalian genes such as ion channels and membrane receptors by injecting purified mRNA or in vitro transcribed RNA. The oocyte is a self-contained system, capable not only of translation of exogenous mRNA's but also of post translational modifications. These modifications might be important for receptor expression and include phosphorylation, glycosylation and subunit assembly as well as the ability to insert the molecule into the membrane. Proteins are targeted to any other predestined subcellular compartment and secretory proteins are exported.

Functional Expression of G-protein Coupled Receptors.

Figure 1:
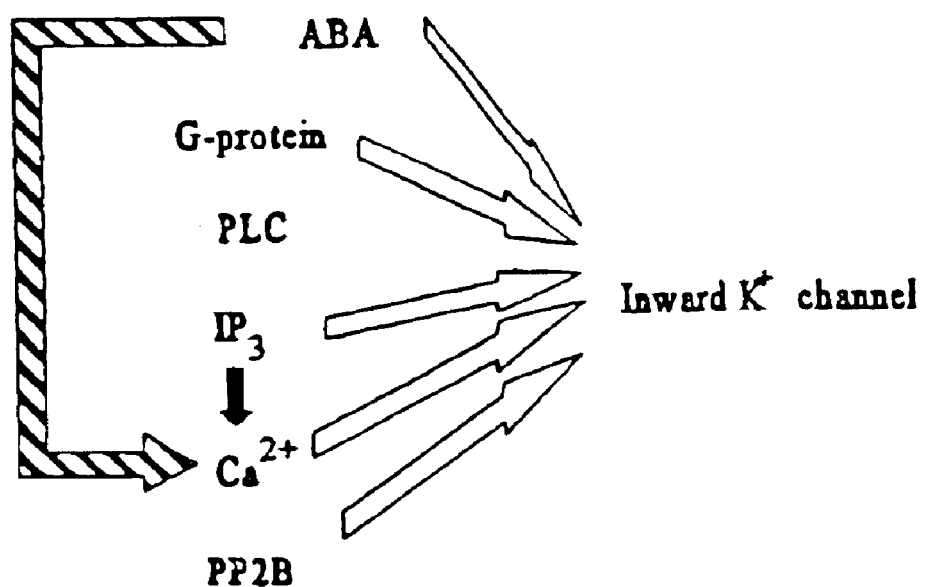
Figure 2:
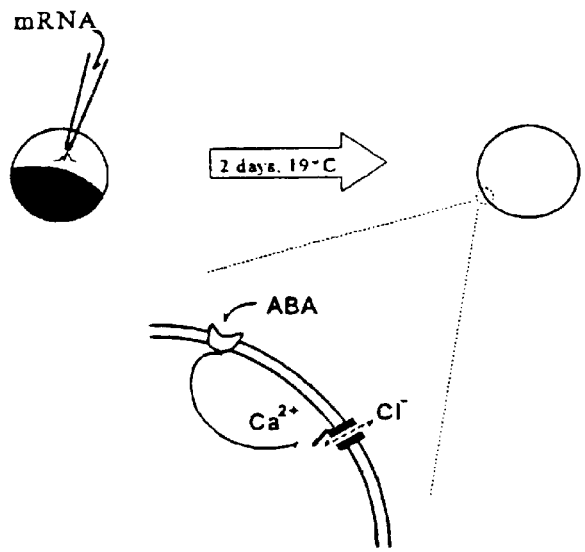
FIG. 2A is a scheme of anticipated coupling of a plant ABA signalling component to oocyte endogenous signal components. ABA current response is used as assay for ABA signalling component expression in RNA injected oocytes.
FIG. 2B is a flow diagram of the cloning strategy for isolation of a functional ABA cDNA clone.

G-protein coupled receptors belong to a family of membrane spanning receptors featuring 7 membrane segments (7TMS). 7TMS receptors can be functionally expressed into Xenopus oocytes, and successfully coupled to endogenous signal transduction components. Evidence exists that foreign 7TMS receptors can be coupled to G proteins and to phospholipase C (PLC) native to the oocyte. Thus, $IP_3$ induced $Ca^{2+}$ mobilization occurs when oocytes, expressing muscarinic receptor are stimulated with acetylcholine. Coupling of 7TMS receptors to endogenous channels via intracellular $Ca^{2+}$ is known. Recently it has been shown that an adenylate cyclase coupled receptor can also be functionally expressed in oocytes and coupled to an endogenous G protein. In this case, the agonist of the EP2 and IP prostanoid receptors was found to activate a co-expressed cystic fibrosis transmembrane conductance regulator, a cAMP-dependent Cl⁻ channel via stimulation of an adenylate cyclase which elevated intracellular cAMP elevation FIG. 2 summarizes the general pattern of expression and coupling indicated from these related studies. The fully expressed and functional receptor is inserted into the oocyte membrane and coupled to the oocyte endogenous G protein. After stimulation by an appropriate ligand, PLC activation occurs. Phosphoinositol diphosphate ($PIP_2$) hydrolysis results in synthesis of $IP_3$ and diacylglycerol (DAG) and $IP_3$ stimulates the release of $Ca^{2+}$ from internal stores. The rise in intracellular $Ca^{2+}$ activates an endogenous $Ca^{2+}$-dependent $Cl^-$ channel. Indeed any coupling pathway that ultimately leads to an increase in $[Ca^{2+}]$ will promote native $Cl^-$ currents. Alternatively adenylate cyclase is activated by G proteins, resulting in the production of cAMP and stimulation of heterologous cAMP-dependent $Cl^-$ channels.
Expression Cloning of Receptors.

It has been shown that poly(A)$^+$ RNA isolated from mammal brains and injected into Xenopus oocytes could direct to the synthesis and incorporation of functional ion channels that could then be activated by voltage or by neurotransmitter drugs. This expression system can also be used in a strategy to partially clone neurotransmitter receptors and voltage-operated channels. Thus the power of the system can be used to isolate and analyse membrane transporters and receptors.

*Xenopus leavis* Oocyte's Endogenous $Cl^-$ Currents are ABA Inducible when Injected with *N. tabacum* mRNA We have now found that plant mRNA, isolated from plant tissue, or synthesized in vitro using a cDNA clone as template, is also translated when injected in a *Xenopus laevis* oocyte.

Initially, voltage clamp recordings were performed on unifolliculated defolliculated oocytes of *Xenopus leavis*. The outward-rectifying currents measured for cells with fluctuating currents were carried by $Cl^-$ and consisted of two components, one instantaneous and the other time-dependent. The amplitude of this current was $[Ca^{2+}]_i$ dependent. When the outside $[Ca^{2+}]_o$ was elevated, the $Cl^-$ current increased to a maximum value of 500 nA it showed a $t_{1/2}$ for activation of 300 ms at 40 mV after 4 min and subsequently decayed to the background level within 5 min. This $Ca^{2+}$ stimulation most likely results from the $Ca^{2+}$ ions entering the cell via voltage-dependent channels, consistent with previous observations as discussed above.

*Nicotiana tabacum* poly(A)$^+$ RNA was injected and functionally expressed into oocytes. By injecting the mRNA, the oocytes were able to recognize the ABA. The strongly outward-rectifying $Cl^-$ currents, measured in response to ABA were induced most likely via a rise in intracellular $[Ca^2]$ and decayed within 5 min. The maximum current amplitude, 3.1 $\mu$A and kinetics, $t_{1/2}$ 100 ms at 60 mV measured were comparable to the $I_{Cl-1}$ current analysis as described in literature (2.5 $\mu$A and $t_{1/2\ 250}$ ms at 20 mV).

Coupling of the ABA-oocyte Signal Transduction Pathway

With this specific ABA response implanted in oocytes by injection of tobacco mRNA, a coupling has been established between upstream plant hormone perception components and downstream oocytes signalling elements. This is implied by the specificity of the current response. Only when ABA was applied to mRNA injected oocytes was a signal was recorded. When either the ABA or mRNA injections were omitted or substituted, the signal could not be recovered. (1) Potassium acetate, a weak acid like ABA did not evoke the ABA signal in mRNA injected oocytes. (2) Water injected oocytes did not respond to ABA.

A final parallel between plant and oocyte ABA response suggested similar upstream regulatory elements in each case. When a convincing ABA response was obtained, it was never possible to reinduce the outward-rectifying currents a second time with ABA (as tested for 2 positive cells). This suggests desensitisation of the hormone perception molecule (s). Desensitisation is achieved through a negative feedback and often occurs by phosphorylation of amino acid residues in the receptor molecule.

These experiments demonstrate a link formed between hormone perception proteins derived from plants and more downstream transduction elements of *Xenopus laevis* oocytes. This coupling makes it possible to detect and analyse an ABA specific response in the heterologous oocyte system. ABA stimulates a voltage-dependent outward-rectifying $Cl^-$ currents in oocytes, only when the plant components necessary for ABA perception are expressed. The transcript-specific and ABA-induced outward-rectifying currents can now be continually used through the procedure to enrich for and clone the essential genes for this coupling.

Up until now only a total mixture of transcripts has been considered, and it was at this stage that we sought to enrich for and order these candidates to isolate more pivotal ones. The strategy used for cloning was based on the method outlined by Julius et al. (1988) supra with some modifications, and involves fractionation of the mRNA and subsequent construction of a cDNA library in preparation for the sib-selection strategy to isolate the clone(s) that it is responsible for ABA sensitivity in the oocytes.

The mRNA was divided into 10 fractions by size, on a continuous sucrose gradient. The one positive fraction was cloned into a cDNA library using the pSPORT1 expression vector. In vitro transcribed cRNA of the plasmid DNA from 20,000 colonies was injected into oocytes and after in vivo translation, a small but significant ABA response was seen as a transient increase in the outward-rectifying $Cl^-$ current. Sib selection resulted in subsequent isolation of a positive pool of 2,000:200 and finally 20 transcripts which in each case evoked a similar ABA response. With the decreasing pool size the signal was enhanced, consistent with purification of the active transcript(s).

To prepare the library, a plasmid was used as the vector and *E. coli* as the bacterial host. The BRL Superscript Plasmid kit using the pSPORT1 vector was chosen. mRNA was fractionated on a continuous sucrose gradient before arranging the transcripts into a cDNA library.

Via sib-selection a group of 20 cDNA clones were isolated containing genes coding for possible ABA signalling components. cRNA transcripts complementing these genes, were expressed in *Xenopus leavis* oocytes and yielded an ABA signal resulting in the activation of endogenous $Cl^-$ channels. Attempts to subdivide this pool failed in the sense that it was not possible to regain the ABA signal in oocytes expressing cRNA from single clones or pools smaller than 20 clones, ie. the ABA signal could not be recorded when this pool of 20 clones was divided into smaller subsets of clones.

All 20 cDNAs were then analysed by their nucleotide sequence to get an idea which clones might be candidates for ABA signalling elements and which ones could be definitely excluded from further study. All the possible amino acid sequences deduced from this nucleotide sequence were compared with the protein databases. Similarities indicated that some genes were comparable to enzymes or proteins with functions unrelated or unlikely to be associated with signalling, others showed no similarity to anything in the databases, but were considered interesting because they contained several putative membrane spanning regions. Finally, several genes of major interest showed homology with proteins known to have distinct functions in signal transduction. Amongst them were a small G-protein (smG-Nt; SEQ ID NO:14), a calreticulin (cal-Nt; SEQ ID NO:20), a receptor kinase (rek-Nt; SEQ ID NO:6), and a syntaxin like (syr) protein (SEQ ID NO:2).

For the purposes of this section only, the sequence similarity results given by NCBI return with a score and a probability. When the score is higher than 80, the similarity is highly probable, as was seen in most cases (Table 1). When the score is lower than 80, the similarity was not considered to be very significant. This was the case for clones number 5 (transcription factor), 8 (possible surface protein) and 9 (rek-Nt). The low score in number 5 could have been because the similarity here lies between a plant and a *Xenopus leavis* sequence. This clone was not investigated further as homologues may be already present in the *Xenopus leavis* oocytes. Clone number 8 did not show significant homology with anything in databases, but the low score homology with a putative surface protein was interesting because its sequence does contained putative membrane spanning regions. Clone number 9, the receptor kinase like gene, showed at the 5' end similarity with a receptor kinase protein of Brassica oleracea (Table 2) with a high score of 151 which is significant. The low score at the 3' end (65) was also shown to be of importance as a considerable stretch of DNA aligned very well with parts of the receptor kinases (FIG. 3). The probability follows the same but inverted line as the score.

The overall accuracy of the sequence information is estimated to be >99% over the first 300 bp. Analysis of the effects of sequence errors has indicated that such errors do not significantly reduce the probability that the DNA sequence can be identified by BLAST searches.

Additionally, no fill length sequences were used for comparison which might result in only homologous domains instead of full sequence homology. Only the terminal domains (at the 5' and/or 3' ends) were used in BLASTX searches, although they cover more than 50% of the total cDNA insert length and could therefore give a correct image of the sequence similarity of the gene. Clones number 11 (without ORF). 13 (signal recognition particle of human) and 20 (methyltransferase) were sequenced for less than 50%.

As it was not possible to reproduce the ABA signal with pools consisting of less than 20 samples, a different approach was followed to unravel the function of the 20 individual clones. The cDNA inserts of the 20 clones were all partially or fully sequenced, in order to examine which genes might be involved in ABA signal transduction and which ones could be ruled out (Table 1). Initially, the size of the inserts were estimated on agarose gels after digestion of the clones with NotI-EcoRI endonuclease restriction enzymes. Clones number 10 and 17 contained inserts smaller than 200 bp, and were not investigated further. The nucleotide sequence of all the other clones was obtained using the Taq polymerase PCR-sequence reactions and the ABI PRISM 310 Genetic Analyzer. The PCR reaction was accomplished using the T7 primer. The T7 promoter sequence is located in the pSPORT1 vector, flanking the cDNA insert at the 5' end (FIG. 4). For inserts larger than 900 bp, two sequencing reaction were performed, except in the cases of clone numbers 5, 11 and 20. This second reaction was performed using the M13(f) primer. The M13 (f) complementary sequence is located in the pSPORT1 vector flanking the cDNA insert at the 3' end. A sequence of approximately 700 bp was obtained for each reaction.

Sequences were edited manually (EDITSEQ program) to remove vector and poly(T) sequences at the 5' end of the sequence and to resolve ambiguous sequences that were not assigned by the automatic sequencer. The average sequence produced this way was approximately 400 bp in length. The six possible deduced amino acid sequences of the cDNA nucleotide sequences were compared to the nonredundant protein databases using the BLASTX e-mail server provided by NCBI. The results of these BLASTX searches are summarized in Table 1 for the highest scoring homologies together with the score and probability characteristics of the homology. In general, the score is determined from the sum of the integer values of the aligned amino acids from the region of the sequences with the highest similarity. For the purposes of this section only the deduced amino acid sequence homology between the cDNA and a known sequence should be considered significant when the score is greater than 80. The probability P(N) values reported for each sequence homology, represents the number of times a sequence is expected to occur by chance alone during the database search. The closer this value approaches to zero, the more reliable the search is. The closer this value approaches to 1, the less significant the similarity is. The probability values are dependent on numerous factors, including which scoring scheme is employed, the residue composition of the query sequence, an assumed residue composition for a typical database sequence, the length of the query sequence, and the total length of the database.

TABLE 1

The BLASTX results from the 20 clones of the positive pool.
Highlighted clones might be involved in signal transduction.

| nr | size (bp) | T7[a] | M13[a] | Possible function | P(N)[b] | Score[b] | Accession number |
|----|-----------|-------|--------|-------------------|---------|----------|------------------|
| 1  | 750       | *     | —      | —                 | —       | —        | —                |
| 2  | 850       | *     | —      | —                 | —       | —        | —                |
| 3  | 900       | *     | —      | PAR-pathogen related protein (*N. tabacum*) | $8.3e^{-51}$ | 386 | S57419 |
|    |           | —     | *      | PAR-pathogen related protein (*N. tabacum*) | $1.4e^{-16}$ | 136 | S57419 |
| 4  | 1100      | *     | —      | Inorganic Phosphate transporter (*S. tuberosum*) | $3.9e^{-113}$ | 850 | X98890 |
|    |           | —     | *      | Inorganic Phosphate transporter (*S. tuberosum*) | $1.4e^{-33}$ | 267 | X98890 |
| 5  | 1000      | *     | —      | Phosphatase inhibitor (rabbit) Rubisco activase (*N. tabacum*) | 0.036 | 50 | |

TABLE 1-continued

The BLASTX results from the 20 clones of the positive pool.
Highlighted clones might be involved in signal transduction.

| nr | size (bp) | T7[a] | M13[a] | Possible function | P(N)[b] | Score[b] | Accession number |
|---|---|---|---|---|---|---|---|
| 6 | 1100 | * | — | Rubisco activase (N. tabacum) | $6.0e^{-53}$ | 239 | S25483 |
|  |  | — | * | Pathogen related pr4B-protein (N. tabacum) | $3.9e^{-43}$ | 348 | S25483 |
| 7 | 750 | * | — | Putative surface protein (M. sativa) | $8.3e^{-98}$ | 480 | S23800 |
| 8 | 1300 | * | — | — | $9.9e^{-05}$ | 73 | U28149 |
|  |  | — | * | S receptor kinase K4 (B. oleracea) | — | — | — |
| 9 | 1200 | * | — | Receptor kinase (I. trifida) | $3.7e^{-40}$ | 151 | S39911 |
|  |  | — | * | — | $3.2e^{-05}$ | 65 | U20948 |
| 10 | — | — | — | No ORF found | — | — | — |
| 11 | 1250 | * | — | — | — | — | — |
| 12 | 2100 | * | — | — | — | — | — |
|  |  | — | * | Signal recognition particle receptor (human) | — | — | — |
| 13 | 1300 | * | — | Syntaxin-related protein (A. thaliana) | $3.9e^{-16}$ | 167 | W68942 |
| 14 | 1250 | * | — | Syntaxin-related protein (A. thaliana) | $7.3e^{-38}$ | 180 | U39452 |
|  |  | — | * | Small G-protein (rab) (L. japonicus) | $1.0e^{-32}$ | 141 | U39452 |
| 15 | 750 | * | — | No ORF found | $3.2e^{-59}$ | 333 | Z73955 |
| 16 | 500 | * | — | — | — | — | — |
| 17 | 200 | — | — | Carbonic anhydrase (N. tabacum) | — | — | — |
| 18 | 1000 | * | — | Carbonic anhydrase (N. tabacum) | $1.4e^{-117}$ | 765 | M94135 |
|  |  | — | * | Calreticulin (A. thaliana) | $2.0e^{-61}$ | 430 | M94135 |
| 19 | 2500 | * | — | Calreticulin (A. thaliana) | $2.1e^{-62}$ | 495 | U27698 |
|  |  | — | * | SAM methyltransferase (Soybean) | $8.3e^{-09}$ | 131 | U27698 |
| 20 | 1200 | * | — |  | $2.6e^{-61}$ | 267 | U43683 |

[a]*indicates whether either T7 or M13(f) primer were used in the sequencing reaction.
[b]More detailed explanation of the score and probability P(N) of the BLASTX results is given in the text.

Table 1 also lists the possible functions of the 20 proteins encoded by the cDNA inserts. Clones number 10 and 17 were 'empty' clones, with inserts probably too small to code for functional proteins. Additionally, two clones, number 11 and 16 did not appear to contain ORFs (open reading frames). A number of clones, 3, 4, 5, 6, 7, 13, 18 and 20 were homologous to sequences that were well-characterized with functions not obviously related to signal transduction. Indeed, most of these genes have enzymatic functions totally different from a signal perception system. Additionally, clone number 1 did not show any similarities using BLASTX searches. However, when compared to a data bank containing short sequencing patterns (Prosite 13, Lasergene, DNA*, Madison, USA), the gene appeared to possess a multicopper oxidase signature with a 100% accuracy. The homology to this pattern suggest that the protein coded by gene number 1 belongs to a family of copper binding oxidases.

The clones with a highlighted function (Table I) could be of more interest for different reasons. BLASTX searches of clones number 2, 8 and 12 failed to align these sequences to any known sequences stored in the database. Interestingly these clones all possessed membrane spanning regions. Hydrophilicity plots of parts of the deduced amino acid sequences of these genes are shown in FIG. 5 as well as an indication of the possible membrane spanning domains. Possible membrane spanning regions are recognized by a sequence of 20 or more hydrophobic amino acid residues.

(1) Protein number 2 contains four hydrophobic regions in the first 109 amino acid sequence, followed by a very hydrophilic region (FIG. 5A). (2) Protein number 8 showed some similarity to a putative surface protein at the 5' end of the sequence, although the score 73 of this similarity was below 80 which indicates low significance of the homology. The putative surface protein is derived from Medicago Sativa and no more information is available at this point. The hydrophobicity plot of an annealing of the two sequenced stretches using the T7 primer at the 5' end and the M13(f) at the 3' end, reveals three possible different hydrophobic domains from 20 or more amino acids per region and one region close to 20 amino acids residues (FIG. 5B). (3) Finally, a hydrophobicity plot of the first 130 amino acids of protein number 12 shows three hydrophobic domains of at least 20 amino acids long (FIG. 5C).

Small G-protein

One of the clones, number 15 (SEQ ID NO: 14) codes probably for a Rab/Ypt type small G-protein. Even though it can not possibly be a receptor, it could be involved in the signal pathway more downstream of the initial perception event. Similarity searches were performed with a 109amino acid sequence of the cDNA (15) isolated from N. tabacum (SMG-Nt2; SEQ ID NO: 14) (FIG. 6). The highest identity (74.2%) was detected with a constitutively expressed Rab/Ypt -related sequence isolated from soybean (Glycine max), GRM1 (SEQ ID NO: 15). Other very homologous small G proteins are derived from Lotus japonicus, RAB11G (SEQ ID NO: 16) or from Arabidopsis thaliana (ARA-4; SEQ ID NO: 17, and RAB11; SEQ ID NO: 18). Additionally, SMG-Nt2 showed 70.2% homology with another small GTP binding protein of N. tabacum, NT-RAB11E (SEQ ID NO:19).

Small GTP binding proteins have the ability to specifically bind and subsequently hydrolyze guanine nucleotides, thereby using the GTP/GDP cycle as a molecular switch in which the active/inactive state depends on the binding of GTP or GDP, respectively. Small GTP binding proteins can be divided into five families, namely Ras, Rho, Rab/Ypt, Arf, and Ran. The Rab/Ypt family, of which smG-Nt is a member, has been shown to be involved in vesicle-mediated transport and secretion. Rab/Ypt proteins have been found to be associated with membranes through the C-terminal cysteine motif via a fatty acid, mainly a modified isoprenyl moiety.

Calreticulin

FIG. 7 shows an alignment of the clone number 19, cal-Nt (SEQ ID NOs:20 and 22) with the *Arabidopsis thaliana* calreticulin (SEQ ID NOs:21 and 23). The alignments of a 178 amino acid stretch at the 5' end resulted in a similarity of 63.1% and the alignments for 86 amino acids at the 3' end led to 48.8% similarity between the two sequences. Calreticulins are calcium binding proteins in the endoplasmatic reticulum and have an established role as molecular chaperones. It was also suggested they may play a role in signal transduction, specifically in calcium distribution. Some reports support specific functions for calreticulins outside the endoplasmatic reticulum, such as the interactions with steroid hormone receptors. The sequence show a hydrophobic leader sequence, at the N-terminal site of the protein, and a HDEL motif indicating the location in the endoplasmatic reticulum (FIG. 7).

Receptor kinase

Clone number9, rek-NI(SEQ ID NO:6), appeared to be homologous to receptor kinase type proteins, from *Brassica oleracea* (SEQ ID NO:8) or *Brassica campestris* (SEQ ID NO:9) or *Ipomoea trifida* (SEQ ID NO:7). FIG. 3 shows the alignment of the two separately sequenced amino acid strands. The similarity between the N-terminal sequences (FIG. 3A; SEQ ID NOs:6–9), was found to be higher (approximately 60%) than of the C-termini (FIG. 3B; SEQ ID NOs: 10–13), which showed around 400 homology with the receptor kinases from other plant species.

The receptor kinase from *Brassica oleracea* is located in the S gene locus. This locus codes for proteins involved in the self-incompatibility system of these plants that inhibit germination or growth of pollen at stigmatic surfaces that express matching S alleles. This receptor kinase is a transmembrane protein with an extracellular receptor-like domain and a cytoplasmic domain that exhibits serine/threonine kinase activity. However, when expression analysis revealed presence of these receptor kinases in vegetative tissues, other cell-cell signalling roles for these receptor kinases were suggested such as transduction of plant hormone signals.

Syntaxin Related Protein

Experimental evidence suggested that clone number 14, syr (SEQ ID NO:2) which shows homology to the syntaxin-related gene of *Arabidopsis thaliana* is of particular interest. One of these indications is given by the observation of currents when this protein was expressed in oocytes.

One clone, psyr isolated via the sibselection strategy yielded currents in oocytes when expressed in excess. BlastX searches revealed homology with an *Arabidopsis thaliana* protein KNOLLE (SEQ ID NO:24) which is a syntaxin-like protein. Syntaxin proteins are members of a big family and are thought to function as receptors for transport vesicles with different isoforms of this family localized to various membranes throughout the cell. Syntaxin is Greek meaning "putting together in order".

Vesicle Docking and Fusion

The directed movement of molecules within and between cells depends on the precise targeting of transport vesicles to specific membrane compartments. Molecular studies have uncovered a substantial similarity among secretory systems from yeast to neurons. The molecular machinery for both constitutive and regulated secretion was based on dynamic interactions between proteins from a donor (vesicle) and an acceptor membrane (plasma membrane). A model at molecular level of the mechanism of vesicle docking and fusion to its target membrane is generally accepted. The fusion between the two compartments was mediated by a protein complex consisting of cytosolic proteins, NSF (N-ethylmaleimide-sensitive fusion protein) and , SNAPs (soluble NSF attachment proteins) which interact with three synaptic proteins, the SNARE (SNAP receptor) proteins, SNAP-25 (synaptosome-associated protein of 25 kD), VAMP (vesicle associated membrane protein or synaptobrevin) and syntaxin. These three SNARE proteins comprised the minimal core proteins of the docking and fusion machinery. The VAMP resided on the vesicle membrane and is referred to as v-SNARE (vesicle-associated SNARE). Syntaxin and SNAP-25 were localised at the plasma membrane and are referred to as t-SNARE (target-membrane SNARE). The 'SNARE hypothesis' suggests that vesicle targeting and fusion as well as its specificity were governed by the interaction between a v-SNARE and a t-SNARE. The soluble NSF operated as a molecular switch (via ATP hydrolysis) and drove the dissociation of the SNARE complex, releasing syntaxin, SNAP-25 and VAMP and leading to membrane fusion (FIG. 8). Recently, this 'SNARE hypothesis' has been challenged, and it has been described how syntaxin and VAMP would function in vesicle fusion, downstream of the docking in drosophila.

Syntaxin, a Major Component of the t-SNARE Complex.

Syntaxin seems likely to play a central role in exocytosis. The family of syntaxins (syntaxin 1–6) seems still expanding. All syntaxins share common structural features: a hydrophobic transmembrane domain at the carboxy-terminal and the amino-terminal domain is located in the cytoplasm. The cytoplasmic domain contains discrete regions with a high probability of forming a coiled-coil structure. One isoform, syntaxin 1A is very abundant and highly conserved among organisms distant in evolution such as Drosophila and yeast. Originally syntaxin 1A was isolated from brain membranes. It was associated with several of the relevant vesicular or plasma membrane proteins including VAMP and SNAP-25 and the cytosolic proteins NSF and two forms of SNAPs. As a t-SNARE, syntaxin 1A has two postulated functions in the 'SNARE hypothesis'. The first is as a target protein in the plasma membrane, one which interacts with a partner on the approaching vesicle (VAMP of v-SNARE) to ensure specificity of the docking process. The other is as a receptor for the soluble SNAPs, which may be a necessary step in the pathway leading to fusion.

Later it was found that syntaxin can also be associated with other proteins involved in the secretory system. The syntaxin was shown to interact with Munc 13 and Munc 18 (also designated n-sec 1, rop, or rbsec 1) proteins. The function of these proteins are not fully understood, they may be regulators of the core complex formed during this vesicle fusion process. [Note: Only for these two types of proteins (Munc 13 and Munc 18) is the N-terminal region of the syntaxin molecule important for binding, all other syntaxin binding proteins bind at the predicted coiled coil domain immediatly upstream of the amino terminal hydrophobic domain.

It has also been shown that syntaxin interacts with synaptotagmin. Synaptotagmin is an exocytotic $Ca^{2+}$ sensor tagged to the vesicle membrane. As $Ca^{2+}$ rise, the synaptotagmins form dimers and these dimers interact with syntaxin and triggers exocytosis.

Syntaxins as well SNAP-25 and synaptotagmins bind voltage-gated N-type $Ca^{2+}$ channels in a $Ca^{2+}$-dependent way. Coexpression of syntaxin with the N-type $Ca^{2+}$ channels into Xenopus oocytes reduces the $Ca^{2+}$ current amplitude and changes the gating characteristics. Deletion of the C-terminus of the syntaxin abolishes this effect on the $Ca^{2+}$ channels, indicating the interaction lies at the transmembrane region. These experiments show that syntaxin influences the rate of $Ca^{2+}$ influx and provide a link between the $Ca^{2+}$ flux regulation and vesicle fusion.

The ability to participate in these various complexes renders syntaxin 1A a likely candidate for a protein whose interactions with its neighbours could control important aspects of different mechanisms.

Other Possible Functions of Syntaxin

Other functions have been assigned to syntaxin. Only recently it was suggested syntaxin 1A could mediate membrane assembly events throughout Drosophila development.

Interestingly, originally, it has been described that syntaxin 1B from rat could function as a glutamate receptor. Syntaxin was picked up via a screen using antibodies against glutamate binding proteins. When syntaxin was expressed in Xenopus oocytes, it formed glutamate-activated ion channels. It was suggested that some of the amino terminal hydrophilic part of the protein was located extracellular as shown with antibody screens. It was discussed that syntaxin, as in the case for the metabotropic glutamate receptors, might modulate the release of glutamate from synaptic terminals.

Plant Syntaxin Related Genes

Two syntaxin related clones have been described in *Arabidopsis thaliana*. The first one, KNOLLE, was a gene isolated via an Arabidopsis mutant screen. When the KNOLLE gene was knocked out, the plant was impaired in its cell division, in a similar way as a caffeine treatment to plants. It was thought that the protein played a role in fusion of vesicles at the newly forming cell plate.

The second gene cloned is called aPep12 and can functional complement a yeast pep12 mutant. APEP12 is a syntaxin homologue which may function in vesicle trafficking of vesicles from the trans-Golgi network to the vacuole.

Sequence Alignments and Analysis

Nucleotide Sequence and Sequencing Strategy

FIG. 9A shows the nucleotide sequence of the cDNA insert of the syr clone (SEQ ID, NO:1). The derived amino acid sequence (SEQ ID NO:2) is displayed for the open reading frame starting with an ATG sequence at position 17 and terminating at position 920 with a TGA stop codon. The amino acid sequence is 300 amino acids long. Panel B of FIG. 9 shows the strategy used during sequencing. Two deletions were made in either end of the cDNA insert. In order to delete the 3' end of the gene, the psyr was digested with BglII and BamHI restriction enzymes, and the remaining strand was religated. This new construct, psyrbb was used as a template in a sequencing reaction with the M13(f) primer. The other 5' end was deleted by digesting the psyr clone with SacI and EcorI, the overhanging single strand DNA ends were made blunt using the T4 polymerase and the vector was consequently religating. This new construct, psyrse was used as template in a sequence reaction with the T7 primer. The centre part of the cDNA between the BglII and SacI restriction enzymes was cloned into pBluescript vector, so that the insert is flanked by the two M13 primers: the forward M13(f) and the reverse M13(r) primer, which were used in the two sequencing reactions with this construct, psyr2. By merging the sequences of these reactions into a contig (FIG. 9B), all dubious nucleotide sequences could be resolved and the full length sequence of the syntaxin related gel was obtained (FIG. 9A).

Sequence Alignments and Protein Structure

The SYR amino acid sequence (SEQ ID NO:2) was aligned with the KNOLLE syntaxin like protein from *Arabidopsis thaliana* (SEQ ID NO:24) and with two proteins from the syntaxin family, syntaxin A (SEQ ID NO:25) and syntaxin B (SEQ ID NO:26) from human (FIG. 10). The protein sequence contains 3 main regions. (1) The hydrophobic C-terminus which can be a membrane spanning domain. (2) A zone upstream from the hydrophobic domain consists of an epimorphin pattern as aligned with the 'boxes' of the Prosite Database (Lasergene, DNA*, Madison, USA) (3) The N-terminus of the protein sequence is hydrophilic and does not contain significant homology to known sequence signatures.

(1) The overall hydrophobicity profile is the same for all members of the syntaxin family. The C terminus end exists of a sequence of 21–24 hydrophobic amino acid possibly representing a membrane spanning region. (2) The epimorphin pattern is very highly conserved amongst the syntaxin proteins with an identity of >80% at amino acid level between the syntaxin A and B proteins of rat and human. The highest amino acid identity level in this epimorphin pattern zone of the tobacco SYR protein is 64.1% with the KNOLLE, 53.8% with the syntaxin A of Drosophila, and 51.3% with syntaxin A and B of human and rat. This epimorphin pattern collocates with a coiled coil region, indicating that protein protein interaction is common among the syntaxin family. (3) The N-terminus is the most divergent region, the first 62 amino acids of the SYR protein of tobacco showed only 17.7% identity with the KNOLLE protein and the first 209 showed 34% with the KNOLLE, but this N terminal hydrophilic region was more divergent with all the mammalian syntaxins, the highest identity scores recorded were 17.3% with the syntaxin A of human and syntaxin B of rat. This region however, showed higher homology amongst the syntaxin A and B of human and rat. Similar identity scores were detected as for the epimorphin pattern, higher then 77%. Additionally, an interesting domain, a nucleotide binding site (NBS) was observed in the SYR protein that was absent in the KNOLLE gene (*A. thaliana*) or in any other syntaxin protein whose sequence is published. This NBS domain, together with the overall dissimilarity levels of this N terminal hydrophilic zone, indicates a different regulation of the SYR protein in comparison with the so far identified members of the syntaxin family.

One other gene of this family has been cloned in plants, namely the pep 12, syntaxin like proteins from *Arabidopsis thaliana*. Homology of the SYR tobacco protein with this protein however is low, only 18.3% overall amino acid identity. The protein PEP12 is located in the post-golgi compartment, which shows a different function as the syntaxin 1A or 1 B proteins which are located in the plasma membrane. To provide an overview of the alignments, a phylogenetic tree is displayed of a representation of members of the syntaxin family in FIG. 11. This tree is based on the comparison of the full amino acid sequences.

More particularly, sequencing of the transcript cDNA showed that it contained an open-reading frame that encoded a syntaxin- (t-SNARE-) related protein (Nt-Syr) of 300 amino acids with a predicted molecular mass of 34.01 kD and an isoelectric point of 7.95. Alignments of Nt-Syr protein by the Clustal method using Megalign (DNAstar, Madison USA) showed 37.7% identity with one other syntaxin-like protein from plants, the Knolle gene product identified from *Arabidopsis thaliana*, and a low but significant homology (22.8% amino-acid identity) to its closest mammalian homolog encoded by the human syntaxin gene SYN-1A. Structural and PRO-SITE analyses of Nt-Syr revealed features common to syntaxin proteins (FIG. 41) including a single, putative membrane-spanning (hydrophobic) domainatits C-terminus (FIG. 41; SEQ ID NOS:38–40), and three domains (H1–H3) with high probabilities for forming coiled-coil structures in protein-protein interactions. Of these putative coiled-coil domains the third, adjacent to the putative membrane-spanning region (SEQ ID NO:35) showed 84% identity (92% homology) with the epimorphin consensus sequence of mammalian Syntaxin-1A (SEQ ID NO:37). Nt-Syr also showed partial conservation of the three dispersed sites necessary for binding and cleavage of the protein by Clostridium botulinum type C toxin (BotN/C; FIG. 41). However, unlike other syntaxin proteins characterised to date, Nt-Syr was found to include a single, EF-hand consensus sequence (SEQ ID NO:33) between amino-acid residues 16 and 28, and a putative nucleotide binding site (SEQ ID NO:34) between residues 114 and 119.

New Screen

The pool of 20 clones can not be subdivided or a component is lost necessary to detect the ABA responsive signal. Expression of the syr gene only in oocytes resulted in a recording of increasing outward-rectifying K$^+$ current, and the ABA signal was lost.

Induction of K$^+$ Currents

The SYR protein, which is a syntaxin-related protein, yielded upon expression in oocytes an in time increasing outward-rectifying currents. Syntaxin proteins are likely to interact with Ca$^{2+}$ channels (N-type). However, the currents yielded with the SYR protein are not sensitive to ω-conotoxin, a toxin that specifically inhibits type N Ca$^{2+}$ channels. In contrast, the currents observed on the SYR expressing oocytes appeared to be carried by K$^+$, as characterized with the reversal potential and various toxins (TEA and Ba$^{2+}$). These experiments together with the fact that a similar current can be detected in uninjected oocytes indicates that when SYR is expressed in high quantities in oocytes, it associates to oocyte endogenous voltage-dependent K$^+$ channels. The SYR protein would this way act as regulatory subunit of a pre-existing silent channel complexes rather then forming a channel per se.

After impalement of the oocytes expressing SYR, the outward-rectifying current induced over time.

Experiments are presented below to unravel the function of the SYR protein in plants. The first one comprises the elimination of (a) syntaxin like protein(s) in Nicotiana benthamiana and Vicia faba by a specific toxin (botulinun) leading to a failure of ABA response in the guard cells. The experiment to knock out the SYR protein implemented the botulinun toxin, which very specifically digests the SNARE proteins. The family of botulinum toxins are neurotoxins produced by Clostridium botulinum and causes neuroparalytic syndromes to human by blocking the release of neurotransmitters. There are 7 different types of botulinum toxins, and they are all composed of two disulfide-linked polypeptide chains. The larger subunit is responsible for recognition and cell penetration. Reduction releases the smaller chain in the cytosol, where it displays its zinc-endopeptidase activity specific for components of the exocytosis apparatus. Botulinum B, D, F and G recognize specifically VAMP. Botulinum A and E recognize specifically SNAP-25. Botulinum neurotoxin type C cleaves syntaxin (for review see: Montecucco and Giampietro, 1995). The effect of this syntaxin specific botulinum C (BotN/C) was tested on guard cells, botulinum D (BotN/D) was used as form of control.

Botulinum toxin BotN/C Abolished ABA Response in Guard Cells

In normal conditions, the effect of ABA on the guard cells of n. benthamiana resulted in an increase of the anion currents and a reduction in the inward-rectifying potassium current. Antagonistic effects on both the distinct currents in guard cell membranes were abolished when the cells were loaded with BotN/C, ensuring the reliability of this elimination experiment. It was interesting to note that the BotN/C toxin did not show any immediate reaction upon the currents per se in the guard cells but only when the cells were challenged with ABA was the impact of BotN/C apparent. These results particularly indicate that the syntaxin-like proteins which were inhibited by BotN/C have a function in the ABA signal response pathway in guard cells. Additionally, the action of BotN/C was confirmed by eliminating the inhibitory effect of ABA in the I$_{kin}$ of V. faba. These results indicate that BotN/C acts universally in all plants. The specificity of the BotN/C toxin was further demonstrated by testing the effect of another endopeptidase, BotN/D as control. The ABA response; of each of the currents, anion and potassium, in the guard cell of N. benthamiana were unaffected after treatment with BotN/D.

Other analysis yielded also more information about the function of SYR in Nicotiana tabacum. The gene expression pattern during stresses or ABA treatment was examined. The genomic organisation in Nicotiana tabacum, and Nicotiana benthamiana and Arabidopsis thaliana was analysed to test whether the SYR gene which was present in the different plant species was a member of a closely related family as in the mammalian world. Additionally, a yeast strain mutated in its syntaxin like genes was transformed to express the SYR protein. The SYR protein of N. tabacum turned out to be functionally non-interchangeable with the yeast analogues.

We used BotN/C toxin to disable the Nt-Syr (also called SYR) protein in planta. BotN/C toxin specifically cleaves human syntaxin-1A and related syntaxins containing the necessary recognition and cleavage sites with the consequent disruption of secretion. Nt-Syr includes homologs of the X1 and X2 recognition sites necessary for BotN/C recognition and shows partial conservation of the BotN/C cleavage site between the epimorphin pattern consensus sequence and the C-terminal membrane-spanning domain (FIG. 41). Western blot analysis of Nicotiana leaf microsomal proteins showed that Nt-Syr was specifically recognised and cleaved by the BotN/C toxin, whereas Nt-Syr was unaffected by BotN/D toxin (FIG. 42A) which targets the v-SNARE protein synaptobrevin. Loss of the protein cleavage (30 kD) band in assays with BotN/C was probably related to instability of the cleavage product and its subsequent breakdown by endogenous proteases. Nonetheless, the specificity of BotN/C action was indicated by the fact that cleavage was observed only when protein extracts were pretreated with ATP (FIG. 42A). Syntaxin susceptibility to BotN/C depends on disassembly of the syntaxin-SNARE complex which is facilitated by the NSF ATPase. On the basis of these results, and of observed binding of the Sp2 antibody to high-molecular-weight bands (51 kD and >120 kD, not shown) in leaf protein extracts, it seems likely that Nt-Syr participates in a similar complex in vivo. We tested the effects of BotN/C and BotN/D toxins on ABA-mediated control of guard cell K+ and Cl− channels in Nicotiana and in Vicia. Intact guard cells were loaded after impalement with microelectrodes containing 0.1 M of one or the other of the toxins or, in control experiments, with microelectrodes containing only the normal K+-acetate electrolyte. In guard cells, ABA treatment normally results in a 40–60% inactivation of the dominant, inward-rectifying K+ channel current and a 2- to 4-fold stimulation of current through the Cl-channels. FIG. 42B-D summarises data from Nicotiana, and similar results were obtained in recordings from Vicia guard cells (not shown). In control experiments and in guard cells loaded with BotN/D toxin, ABA treatments led to the characteristic K+ and Cl-channel responses. For the data shown in FIG. 42B and D, measurements were carried out in the presence of 15 mM CsCl and 15 mM TEA-Cl to eliminate the background of K+ currents, and the Cl-channel current quantified during steps to voltages between +30 mV and −200 mV after preconditioning steps to +50 mV to activate the current. Adding 20 M ABA resulted in a 3-fold stimulation of the Cl− current amplitude (FIG. 41B, D:, −ABA; , +ABA) and a characteristic slowing of its relaxation at negative voltages (FIG. 41B, below) compared to the control (FIG. 41B, above). In contrast after loading with BotN/C toxin voltage clamp recordings showed a complete loss of sensitivity to ABA (FIG. 41B, center and FIG. 41D, ). A similar loss of sensitivity to ABA was found for the inward-rectifying K+ channels after treatment with BotN/C, and these results are summarised along with data for the Cl− channels in FIG. 42C. In separate experiments we used the truncated Nt-Syr (Sp2) protein (see FIG. 41A) to "poison" Nt-Syr functioning in planta. We reasoned that if a SNARE-like complex with Nt-Syr was necessary for transmission of the ABA stimulus, adding a truncated Nt-Syr—including the putative protein-protein interaction domains, but lacking the C-terminal membrane anchor—might compete with the native protein for partners and thereby prevent formation of the functional complex. Again, intact guard cells were loaded after impalement, in this case with microelectrodes containing 20 or 100 M of the Sp2 protein. FIG. 43A,C shows the results for the two K+ currents from one set of experiments and additional data, including measurements of Cl− channel currents, are summarised in FIG. 43B. For the data shown in FIG. 43A and C, measurements were carried out in 10 mM K+ outside, and the K+ channel currents quantified during steps to voltages between +30 mV and −250 mV after preconditioning steps to −100 mV (FIG. 43A, top) to deactivate the currents. Under these conditions, activation of the outward-rectifying K+ channels was evident as a sigmoidal rise in positive current at clamp voltages positive of −50 mV and activation of the inward-rectifying K+ channels was characterised by a monophasic increase in negative current at clamp voltages near and negative of −150 mV (FIG. 43A, above). Adding 20 M ABA resulted in roughly a 2-fold stimulation of the outward-rectifier current and, at −200 mV, at reduction of the inward- rectifier current to 24% of the control (FIG. 43A,C: −ABA; , +ABA). ABA treatment also effected a pronounced shift in the voltage-sensitivity of the inward-rectifying K+ channels (FIG. 43C, inset), consistent with an ABA-evoked rise in $[Ca^{2+}]_i$ and the sensitivity of these K+ channels to $[Ca^{2+}]_i$. After loading with the Sp2 protein, however, voltage clamp recordings showed a complete loss of sensitivity to ABA (FIG. 43A, center and FIG. 41C, ). A similar loss of sensitivity to ABA was found for the Cl− channels after treatment with the Sp2 protein, and these results are summarised along with data for the K+ channels in FIG. 43B. These results indicate a central role for Nt-Syr in ABA signalling and adaptation to water stress, and a close interaction with other protein elements in early steps of stimulus perception and transduction. In the first instance, our data implicate Nt-Syr as part of a functional heteromultimeric complex with other proteins.

SYR is Upregulated by ABA

Northern analysis indicated that SYR was upregulated by drought stress and ABA in leaves of V. tabacum. Two independently performed northern experiments with ABA both revealed transient induction of SYR.

SYR is not from a Large Family but is Present in Different Plant Species

From studies with mammalian syntaxin proteins, and because some genes are already known in Arabidopsis thaliana (KNOLLE and PEP12), one might expect a family of syntaxin-like proteins in N. tabacum. Southern analysis using DNA of N. tabacum and SYR as a probe surprisingly showed only few bands indicating that SYR may not be a member of a large family of homologous clones and that only one or two copies of SYR are present. If SYR is part of gene family the sequence homology with other members would be expected to be lower than 70%. Homologous genes with the SYR of N. tabacum were found in the other plant species N. bethamiana and A. thaliana. Also in these plants only one or two copies appear to be present.

Agrobacterium-mediated Transient Expression

To analyse the function of syr, the gene was knocked out from Nicotiana tabacum leaves by introducing an antisense construct into the plant. Introducing the antisense cDNA in the genome of leave cells was done by a transient expression system using Agrobacterium tumefaciens. A. tumefaciens is a plant pathogen bacterium that delivers a well-defined piece of DNA, the transferred DNA (T-DNA), into the plant cell.

The results show that when the syr gene was knocked out by antisense, the leaf tissue was impaired in its transpirational adaptation to drought conditions, in other words, the stoma closure regulation may be impaired and this is exactly the "task" of ABA. The results indicate the in vivo involvement of syr in the signal transduction pathway of the plant stress related hormone, abscisic acid.

EXAMPLE 1

Isolation of Poly(A)+-tailed RNA from Nicotianta tabacum Leaves

Growth Condition of Plants

Seeds of Nicotiana tabacumwere germinated in a greenhouse on water soaked soil covered with plastic foil to maintain the highest humidity possible. A 12:12 hour day-night cycle was applied using Osram 400 W sodium lamps as light source. The temperature was kept around 25 C–28 C. After one week when seeds had germinated the plastic foil was removed. After 5–6 weeks the young leaves were harvested using a scalpel, and immediately weighed and frozen in liquid nitrogen. The frozen tissue was stored at −70 C for further use.

Preparation of Poly(A)+tailed RNA

All aqueous solutions used were pretreated with DEPC (0.001%) which was added to the solution, incubated overnight at room temperature, and autoclaved for 20 min at 120 C and 1 bar. Tris solutions which can not be DEPC treated were prepared with DEPC treated $H_2O$ and autoclaved as above. All plastic material used was direct from the manufacturer and handled with disposable gloves only.

20 g of frozen plant material was ground thoroughly in liquid nitrogen with mortar and pestle until a fine powder was obtained. 10 g of plant tissue may also be used and all necessary solutions halved, otherwise all procedures are identical. The powder was suspended in 100 ml extraction buffer (0.1 M NaCl, 0.01 M EDTA, 2% SDS and 0.05 M Tris.Cl at pH 9) preheated at 45 C and supplemented with 20 mg of proteinase K just before use. This suspension was vigorously shaken in a waterbath at 45 C for 10 min. 50 ml phenol was added, the mixture was transferred to a centrifuge tube, and centrifuged at 6000 g (6000 rpm) in a GSA rotor at 20 C. The upper, aqueous phase was transferred to a new tube and this extraction procedure was repeated with 50 ml phenol plus 50 ml chloroform, and a third time with 100 ml chloroform. Once clarified, the aqueous phase was put on ice after determining the volume. 10% NaCl (5 M stock) (v/v) was added and the mixture set on ice for 20 min. Thereafter, it was centrifuged for 10 min at 23500 g (12000 rpm) in a GSA rotor at 4 C and the supernatant decanted and set on ice.

mRNA was purified by oligo-dT chromatography. For this step 0.5 g oligo-dT cellulose (Boehringer Mannheim) was pretreated with a wash of 30 ml 0.1 M NaOH in a new 50 ml plastic tube. The oligo-dT cellulose was spun down by centrifugation at 1500 rpm for 5 min. The pretreatment was followed by two similar washes with $H_2O$ and two washes with binding buffer (0.4 M NaCl, 0.2% SDS, 0.01 M Tris.Cl at pH 7.5). The oligo-dT cellulose was divided equally between two 50 ml tubes with a total of 10 ml binding buffer per tube, and the plant extract was added to both tubes. The suspension was gently agitated by turning the tubes up and down at room temperature for 30 min in order to hybridize the poly(A)$^+$ strand of the transcripts to the oligo-dT strand attached to the cellulose. Thereafter the tubes were centrifuged at 1500 rpm for 5 min, the supernatant decanted, and the cellulose was washed twice with binding buffer and twice with washing buffer (0.1 M NaCl, 0.01 M Tris.Cl at pH 7.5). The cellulose was suspended in 25 ml wash buffer per tube and transferred to one single plastic column (diameter 1 cm, length 10 cm, BioRad) where washing was continued with washing buffer (~100 ml) until the eluate was free of RNA as measured spectrophotometrically ($A_{260=0}$). The poly(A)$^+$ tailed RNA retained on the cellulose was eluted with elution buffer (0.01 M Tris.Cl at pH 7.5) preheated to 55 C. 1 ml elution buffer was poured onto the column and 1 ml eluate was collected each time in each of 10 separate eppendorfs. RNA quantities in each of these tubes was estimated by spottogram (see below). The aliquots containing the RNA (usually in the $3^{rd}$ and $4^{th}$ eppendorf), were ethanol precipitated by adding 10% NaCl (5 M stock) (v/v) and 2.5 times this total volume of chilled (−20 C) ethanol. The solution was chilled to −20 C for at least an hour to precipitate the RNA. RNA can be stored in ethanol for several weeks. When needed, the poly(A)$^+$ tailed RNA was centrifuged at highest possible speed for 20 min in a microcentrifuge and the pellet formed was washed with 70% chilled (−20 C) ethanol. The pellet was dissolved in an appropriate amount of DEPC treated water to a concentration of approximately 1 $\mu g/\mu l$.

Spottogram

RNA samples of small concentrations were quantified by comparison with a standard RNA sample with known concentration. This sample can be purchased commercially or it can be an unused RNA sample from which the concentration was determined by spectrophotometry. For standard RNA samples at an approximate concentration of 1 $\mu g/\mu l$ the solutions were diluted at a rate of 10 $\mu l$ in 990 $\mu l$ water and the OD was measured at 260 mm to determine the concentration using the conversion factor where $A_{260}$ of 1.0=40 $\mu g/ml$ RNA. Once known, this standard RNA sample was diluted to a concentration of 10 ng/$\mu l$. A weighing boat was used to make a series of standards in drops using ethidium bromide (EtBr 10 $\mu g/ml$) which was added last, just before detection on the UV lamp, as follows:

| RNA (ng)      | 0 | 10 | 20 | 30 | 40 | 50 | 60 | 70 | 80 | 90 |
|---------------|---|----|----|----|----|----|----|----|----|----|
| RNA ($\mu l$) | 0 | 1  | 2  | 3  | 4  | 5  | 6  | 7  | 8  | 9  |
| $H_2°$ ($\mu l$) | 9 | 8  | 7  | 6  | 5  | 4  | 3  | 2  | 1  | 0  |
| EtBr ($\mu l$) | 1 | 1  | 1  | 1  | 1  | 1  | 1  | 1  | 1  | 1  |

In parallel, 2 $\mu l$ of the unknown samples were loaded in separate drops diluted with 8 $\mu l$ of $H_2O$ and supplemented with 1 $\mu l$ EtBr. The weighing boat was put on the UV lamp and RNA concentration was determined by comparison of luminescence intensity.

EXAMPLE 2

The *Xenopus laevis* Oocytes and their Preparation

Maintenance of *Xenopus laevis*

Female *Xenopus laevis* toads from South Africa were purchased from Blades Biologicals in the UK. They were kept at 18–20 C with a 12:12 hours day/night cycle in a large water tank containing about 10 cm dechlorinated water (obtained by air evaporation overnight) so that the animals had unrestricted access to the surface. The toads were fed 3 times a week with beef mince or chopped heart (<5% fat). The tanks were cleaned about 3–4 hours after feeding. For purpose of identification, individual toads were labelled subcutaneously with coded transponders (Animalcare Limited, York, UK).

Preparing Oocytes for Injection

Oocytes were removed from the *Xenopus laevis* toads by surgery after anaesthetization on ice for 3 hours. Using a scalpel, a small incision (about 1 cm) was made in the lower third of the abdomen through both the loose skin and the wall of the body cavity. The ovary lobes were easily identified and were gently teased out using forceps. The lobes were cut away and placed in a Petri dish containing Barth's solution (88 mM NaCl; 1 mM KCl; 0.33 mM Ca(NO$_3$)$_2$; 0.4 mM CaCl$_2$; 0.82 mM MgSO$_4$; 2.4 mM NaHCO$_3$ and 10 mM Hepes at pH 7.5 sterilized by autoclaving and supplemented with gentamycin sulphate (0.1 mg/ml) and sodium penicillin (0.05 mg/ml)). The incision was closed with two stitches through both the outer dermis and the inner body wall using catgut (plain 3/0, 26 nm cutting, 75 cm long, W250, Ethicon, Edinburgh, UK). Thereafter, toads was transferred to an isolated tank with 2–3 mm distilled water to allow recovery. Toads were returned to their main tanks once full movement had returned.

To prepare the oocytes, the ovary lobes were peeled apart to give small clumps of about 5–10 oocytes. The follicular cell layer surrounding the oocytes was enzymatically removed in a Barth's solution containing 2 mg/ml collagenase plus 1 mg/ml trypsin inhibitor, while agitating on an orbital shaker (0.5 strokes/sec) for 1 h at 20 C. This treatment was finished by washing the oocytes several times with Barth's solution. Finally the oocytes were released by manually teasing apart the remaining follicular layer.

It was important to select for the surviving oocytes that were not damaged. Fully grown, immature oocytes of stage V–VI were used for expression experiments. Healthy oocytes have distinct animal (dark) and vegetal (light) polar hemispheres and a sharp equatorial band. Oocytes with light spots or mottled appearance on the animal pole were discarded. Oocytes were handled with a pasteur pipette cut off so as to produce an aperture of about 3–4 mm which was made blunt in a flame.

Injection of the Selected Oocytes

Selected oocytes, stage V–VI (diameter of 1.2 mm), were injected with RNA at a concentration of 1 µg/µl. Injections were carried out 24 h after the surgery with a micropipette made from a glass capillary tube with a wall thickness of 0.3 mm and a cross-sectional diameter of 1.8 mm (Kimax-5 1, Kimble Products, USA). The capillary was pulled to an approximately 1 cm long shank with a horizontal puller (P-D5, Narashige Scientific Instruments. Japan). The tip of the micropipette was broken to give an opening of ~10 µm tip diameter. The micropipette was mounted on a micromanipulator and connected to a pneumatic picopump (World Precision Instruments, Sarasota, USA) which is driven by inert $N_2$ gas. This pump can regulate the hold pressure, so that the solution in the micropipette does not flow by capillary forces. It can also regulate the eject pressure, controlled by a foot switch, and the injection volume is determined by the combination of settings for inject pressure and the time of the pulse during injections.

The injection volume was set by pre-calibrating the injection pipette with 1 µl DEPC treated $H_2O$ on a piece of parafilm. The solution was sucked up in the pipette by capillary force, by eliminating the hold pressure. The pipette was subsequently calibrated to release the same volume with 15–20 ejection pulses, as the oocytes can be injected with a maximum of 75 nl. Subsequently 1 µl RNA solution was applied on the surface of the paraflim and loaded into the pipette by capillary force, with the hold pressure off. 20 oocytes were arranged into a row against a microscope slide on the lid of a petri dish with a minimum of Barth's buffer to prevent the cells from drying out. The RNA was injected in each oocyte individually by inserting the pipette into the cell followed by one ejection pulse. After injection the oocytes were transferred immediately into a new petri dish filled with plenty of fresh Barth's solution. Oocytes were incubated for two days at 20 C with daily changes of Barth's solution.

EXAMPLE 3

Voltage Clamp Method

Experimental Set Up

All voltage clamp experiments were performed in a Faraday cage was to guarantee electrical isolation (FIG. 13A). Measurements were carried out holding the oocyte in a specially designed chamber, permitting access with microelectrodes and continuous buffer flow. For electrical measurements, two microelectrodes were used to impale the cell and measure current and voltage. Microelectrodes were electrically connected by Ag/AgCl halfcells to a pair of high-impedance amplifier (µP12 system, WyeScience, Wye Kent). A computer (Compuadd, C466D, Austin, Tex., USA) running the µLab programme (WyeScience, Wye, Kent, UK) was used to generate a command voltage, while simultaneously recording membrane current and voltage during voltage clamp measurements. Voltage clamp measurements were carried out via a conventional two electrode circuit where the voltage signal was conditioned by one amplifier and subsequently compared to the command voltage by another, high gain, differential amplifier (WyeScience, Wye, Kent, UK) before being returned to the cell as a current. All signals were monitored on an oscilloscope (Oscilloscope (DSO) 400, Gould Electronics Ltd, Ilford, Essex, UK ) and membrane voltage was also recorded on a chart recorder (type BD112, Kipp & Zonen, Holland). This current signal was filtered with a six-pole Bessel filter (fc=0.3 or 1 kHz) and both current and voltage signals were digitised at 2 kHz (WyeScience, Wye, Kent, UK) and stored as binary code on a disk.

Chamber Design and Superfusion

Chambers were made from a 2 mm thick perspex circle by drilling through the centre 3 interconnected slots and closing at the bottom with a cover slip (FIG. 13B). Single oocytes were put in the middle gap so that both microelectrodes could be impaled from one side without moving the cell. The chamber was filled and a permanent flow of Ringer's buffer was maintained from a syringe needle placed at the first hole with excess solution removed from the third using a pasteur pipette connected via a vacuum flask to a pump. Aspirator bottles containing the solutions used during the experiments were installed into an enclosure above the Faraday cage and perfusion flow was achieved by gravity feed. Each aspirator bottle was connected with a PTFE tube to a sixway stopcock and then to a fourway stopcock leading towards either the chamber or a waste beaker. Efficient solution changeover was obtained with a minimum time for the new solution to reach the chamber and the cell. Solution changeover in the bath was measured by recording the change in tip potential. Measurements with the electrode placed in the central well showed a 40 to 45 s lag from solution changeover before the new solution reached the chamber and an exchange halftime of 5–6 s.

Microelectrodes and Halfcells

Microelectrodes were made from round thin walled glass tubes (cross-sectional diameter: 1.5 mm, wall thickness: 0.3 mm) with an inner filament (GC150TF-10, Clark electromedical instruments, Reading, UK). A tip with a diameter of 5 µm was pulled using a vertical puller (PP83, Narishige, Japan) and the electrode was filled with 3M KCl using a 2 ml syringe and needle.

Halfcells were constructed of silver wire (1 mm diameter) which was soldered to a standard 2 mm jack plug, pushed through a piece (3–5 $mm^2$) of silicon rubber and inserted into a plastic pipette section. The silver wire was coated with AgCl by filling the pipette with fresh hypochlorite overnight. The halfcell was then rinsed several times and filled with 3 M KCl. This overnight coating procedure was repeated every day during the measurements. Microelectrodes were fixed with dental wax (Kerr soft green impression compound. Kerr Manufacturers, USA) after inserting the shaft into the pipette end of the halfcell. Two microelectrodes and halfcells were used in impalements for voltage clamping. A third electrode was used as reference and was connected to the circuit ground. Contact to the bath in this case was via a glass capillary (cross sectional diameter: 1.5 mm, Clark electromedical instruments, Reading, UK) bent with a hook of 45 and filled with 3 M KCl in 2% agarose which was attached to a halfcell as before.

Voltage Clamp Measurements

Whole-cell voltage clamping was performed on individual (un)injected oocytes in order to record the current $I_m$ needed to bring the membrane potential $V_m$ under experimental control. A two electrode clamp was used. Therefore two separate electrodes were impaled into the cytoplasm of the cell. One electrode, the voltage-recording electrode, was used to monitor the membrane potential $V_m$. The current $I_m$, necessary to keep the potential constant, even when the membrane electrical conductance was changing, was injected via the second, current-passing electrode. FIG. 14 shows a simplified voltage clamp circuit. The membrane potential $V_m$ was recorded by one amplifier and subsequently compared with the command voltage generated by computer via a clamp amplifier. The difference between the two voltage signals was inverted, amplified and a proportional current $I_m$ was returned to the cell via a second amplifier and the current-passing microelectrode. In this way, membrane voltage was brought under experimental control.

A factor that has to be considered when voltage clamping, is the bath error potential. The bathing solution is grounded by a grounding electrode as described before. All measurements are made relative to this ground, on the assumption that the bath is uniformly at ground. This assumption may not be true when the clamp current is sufficiently large (10 μA) to cause a significant voltage drop across the resistance of the bath solution. This means that the voltage measured by the voltage-recording electrode is actually the sum of the membrane potential $V_m$ and the bath potential. In the experiments presented here, the error is maximum 7 mV at 3.5 μA which is negligible.

With an apparent surface area on the order of 106 m 2, the membrane capacitance of oocytes is high and there is an enormous amount of membrane that must be charged in order to clamp the cell. A fast response time of a voltage clamp is necessary to analyse the kinetics of voltage-gated channels. A fast clamping time (<5 ms to voltage stabilisation) in this case was achieved by minimising the resistance of the current injecting microelectrode (~1 M).

EXAMPLE 4

The Xenopus Oocyte Outward Cl⁻ Currents are Ca²⁺-dependent

Endogenous Outward Rectifying Currents in Oocytes

In a first experiment currents in uninjected oocytes were examined under voltage clamped to identify and characterize the endogenous Ca²⁺ dependent Cl⁻ channels. Very low conductance was observed in most cells while clamping the membrane voltage in normal Ringer's solution. Current activity was correlated with the toad. Some toads produced very 'tight' oocytes, without visible time-dependent currents and very low background in normal Ringer's solution ($g_m$ ranges between 0.01 μS and 0.05 μS) Oocytes from other Xenopus could not be used for expression analysis as they showed too much variation in their background current amplitude or the background conductance was high (>0.4 μS). Oocytes that showed fluctuating currents were used to characterize the endogenous currents with the new voltage clamp set up in the lab.

As shown in FIG. 15A outward rectifying currents were detectable in normal Ringer (87.5 mM Cl⁻). The voltage clamp protocol applied was standard: a holding potential of −60 mV, to set a standard level for comparison, followed by 1 of 8 voltage test pulses ranging from −180 mV to +40 mV, each 1000 ms long, to return to the holding potential at −60 mV. To simplify the figure, traces are displayed by overlapping the currents of the different cycles. A strongly outward rectifying current was activated upon depolarization of the membrane from the holding potential (−60 mV) to voltages more positive than −10 mV. The current exhibit two components, an instantaneous increase followed by a slowly developing outward current with a $t_{1/2}$ of approximately 300 ms at +40 mV. The outward component of the current was greatly reduced when the Cl⁻ concentration in the bath was decreased to 30 mM Cl⁻ (Cl⁻ was replaced by $SO_4^{2-}$) consistent with the shift in driving force for Cl⁻ across the membrane. This effect was reversible as the outward currents recovered when the chamber was refilled with normal Ringer (87.5 mM Cl⁻). This was the first indication that the outward current is carried by Cl⁻ ion influx into the cell [1].

[1] Outward rectifying current underlies efflux of positively charged cations or influx of negatively charged anions. Inward-going current is caused by influx of cations or efflux of anions.

Reversal Potential of the Cl⁻ Current

To ascertain the ion by which the current is carried, the reversal potential was experimentally determined and compared with the theoretically calculated equilibrium potential for that particular ion. The equilibrium potential is the potential where the electrical force balances the diffusional force which is dependent upon the concentration of the ion on either site of the membrane. For a simple diffusion regime and assuming activity coefficients of unity, the equilibrium potential of an ion S is defined by the Nernst equation with the inside $[S]_i$ and outside $[S]_o$ ion concentrations as variables:

$$E_s = RT/z_s F \ln([S_o]/[S]_i) \tag{I}$$

With R being the gas constant, T the temperature, $z_s$ the charge of the ion and F the Faraday constant. At 25 C RT/F is 25.69 mV. The $[Cl^-]_i$ of oocytes is ~30 mM, and the $[Cl^-]_o$ in the normal Ringer's solution is 87.5 mV. Thus from equation (I), the equilibrium potential of Cl⁻, $E_{Cl}$, equals −28 mV.

In order to determine the experimental reversal potential, the cell was clamped at a prepulse of +50 mV for 500 ms to activate the current. Subsequently the membrane was stepped to voltages ranging from −160 mV to +30 mV. At voltages from +60 mV to −3 mV the currents relaxed (tailed) negative-going and at voltages from −34 mV to −160 mV the currents relaxed positive-going. Because these relaxations are the consequence of deactivation of the activated current, no change in recorded current is expected at its equilibrium potential. At voltages positive and negative of this potential, the sign of the relaxation should be opposite. The reversal potential is the potential at which the current reversed direction and was determined to lie between −10 mV and −30 mV consistent with the predicted $E_{Cl}$ (−28 mV). The current was likely carried by Cl⁻ ions (FIG. 15B, arrow). Another observation in correlation with the experiments on uninjected oocytes was that the Cl⁻ currents run down in time. In any one batch of oocytes that showed spontanous Cl⁻ currents, these often became gradually 'silent' over the days after operation.

Ca²⁺-dependency of the Cl⁻ Currents

The last panel in FIG. 15C) shows the influence of external $[Ca^{2+}]_o$ on these outward Cl⁻ currents. In this experiment, the oocyte did not show much current when clamped in the normal Ringer's buffer with a Ca²⁺ concentration of 1 mM. When, however, the Ca²⁺ concentration was increased to 10 mM—while keeping the $[Cl^-]_o$ at 87.5 mM—a current activation upon depolarization was recorded after a time delay of 4 min taking into account the time of solution change in the chamber. The response was transient and decayed to the background current level within 5 min after the 14S maximum peak current. This induced current was also carried by Cl⁻, as demonstrated by tail current analysis (not shown). The 4 min time delay in the response was probably due to the fact that the Ca²⁺ ions have to enter the cell first via Ca²⁺ channels, because these Cl⁻ channels are dependent on the intracellular $[Ca^{2+}]_i$ concentrations.

EXAMPLE 5

ABA Response at Oocytes Injected with Tobacco Purified mRNA

Purification of Poly(A)⁺ RNA of *Nicotiana tabacum*.

Of vegetative tissues, the leaves are one of the major targets of abscisic acid. The leave organs were used as starting material for the ABA receptor cloning project. *Nicotiana tabacum* SR1 was chosen as prototype plant.

The poly(A)⁺ RNA was isolated directly from the plant tissue pooled from different plants, with phenol and chloroform extractions followed by isolation using oligo-dT cellulose. The poly(A)⁺ RNA was purified with an additional step (ethanol precipitation) and, after determining the concentration by spottogram, was dissolved in DEPC treated H$_2$O to give a final 1 µg/µl solution.

ABA Response of a Typical mRNA Injected Oocyte.

Oocytes were injected with 50–75 µl of the 1 µg/µl Poly(A)⁺ RNA suspension and after 2 days of transcript expression, voltage clamp measurements were performed on individual cells. FIG. 16 shows the electrical response to ABA of a typical mRNA injected cell. The standard voltage protocol for Cl⁻ current analysis was used: the membrane was stepped from a holding potential at −120 mV after a condition period of 500 ms to different test voltages ranging between −180 mV and +60 mV for 1 s and then was returned to the holding potential. This cycle was repeated 8 times for potentials evenly spread between −180 mV and +60 mV. The currents of the different voltage cycles are shown overlaid in FIG. 16A. In normal Ringer's buffer, no significant time-dependent currents were recorded at any voltages. When ABA (20 µM) was added to the normal Ringer's solution in the bath, time-dependent outward-rectifying currents were detected on stepping from the holding potential of −120 mV to voltages more positive than −10 mV. These currents rose with a $t_{1/2}$ of 200 ms at 25 mV and deactivated in a roughly mono-exponential fashion ($t_{1/2}$ 100 ms) on repolarization to −120 mV (FIG. 16A centre). The stimulation by ABA was transient and current decayed completely within 5 minutes (FIG. 16A right). A depolarization in the free running membrane potential was also observed that coincided with the current increase.

FIG. 16B shows the whole-cell steady-state current as recorded before, and at two time points during ABA exposure (20 s and 5 min). In this case, the steady-state current was taken from currents at the end of each test pulse and is displayed as a function of the clamp voltage. It is evident that ABA evoked a current that activated at voltages around −160 mV. An increase of more then 3 µA is clearly visible at +60 mV.

The reversal potential of the ABA-evoked current was determined as described above (The reversal potential of the Cl⁻ currents). A conditioning pulse was applied at +20 mV, to activate the current, followed by 1 of 8 test pulses between −180 mV and +20 mV. The current relaxations imposed by the test pulses were negative-going for voltages higher then −10 mV and positive-going for potentials lower then −35 mV. The reversal potential which is the voltage at which the current inverts (between −15 mV and −35 mV) corresponded with $E_{Cl}$ (FIG. 16C).

This ABA response was recorded in 3 cells of a total of 5 cells tested. In 2 of the 3 ABA responsive cells, ABA was applied a second time. In neither case, a second response was detected. From this particular mRNA preparation, the ABA-evoked currents were similar to the ones observed in uninjected oocytes when 10 mM external Ca²⁺ was applied (FIG. 15C).

Statistical Analysis of the ABA Response

The mean of the induced steady-state current of the 3 positive cells is shown in FIG. 17. The steady-state of the ABA induced current was calculated by subtracting the oocyte background current recorded before ABA was added, from the current activated by ABA. The induced steady-state current is plotted as a function of the clamped membrane voltage.

The plants used for the mRNA purification were well-watered. In contrast, in another experiment, plants were either drought stressed or treated with a 20 µM ABA solution for one hour (by spraying the solution on the leaves, see chapter 8 for more details). When mRNA purified from these last plants was expressed in oocytes, the ABA response was recovered in all the cells tested (n=3 when mRNA from drought stressed plants was used and n=1 for mRNA of the ABA treated plants). Addittionaly, the oocyte batches were submitted to variability, because when the positive mRNA sample from the drought stressed plants was injected in another batch of oocytes, the ABA response could not be reproduced (n=3).

Negative Controls Confirm ABA Specificity.

Negative controls demonstrated that the signal was specific to ABA and mRNA injected oocytes. Water injected oocytes did not respond to the plant hormone. No difference in free membrane potential or current during voltage clamp was observed before and after ABA addition (n=8 distributed over different oocyte batches). Moreover, specificity for particular transcripts and not RNA in general was also confirmed by the 20 different RNA pools injected during the course of the project ($n_{total}$=78, see below).

Consideration was also given to weak acid effects. Abscisic acid is a weak acid (pK$_a$ 4.8), and at pH 7.5 (pH of the Ringer's buffer) will be predominantly in the ionized ABA⁻ form, but some protonated ABAH will be present. As this molecule is not longer charged it will distribute across the oocyte plasma membrane. However, little as no weak acid trapping is expected because the extracellular and intracellular pH are roughly equivalent (pH 7.5), so the intracellular pH will not vary significantly. Nonetheless, the increase in the buffer capacity introduced by the weak acid ABA might effect changes in pH and hence also in [Ca²⁺]$_i$. To reassure that it was not the increase in the oocyte intracellular buffer capacity that promoted the activity of the outward Cl⁻ currents, negative controls were also performed substituting ABA with 20 µM potassium acetate (pK$_a$ 4.8) in these separate experiments. In every case, no response was observed when potassium acetate was added. Therefore, it may be concluded that ABA was recognised specifically by the oocytes, but only when they were injected with plant mRNA and that this recognition resulted in an induction of the endogenous, outward-rectifying Ca²⁺-dependent Cl⁻ channels.

EXAMPLE 6

Sucrose Gradient Fractionation mRNA fractionation was carried out using a sucrose gradient. To manufacture the sucrose gradient, 2 stock solutions were prepared: one contained 30% sucrose in 10 mM Tris.HCl (pH 7.5), 1 mM EDTA (pH 8) and 0.1% LDS (lithium dodecyl sulphate), and the other one consisted of the same components apart from the sucrose which was absent. These 2 buffers were mixed in different ratios to give solutions with sucrose percentages of 30%, 26%, 22%, 18%, 14% and 10%. Polystyrene tubes with a volume of 4 ml, were cleaned with DEPC and rinsed thoroughly as they are non-autoclavable. The tubes fit in a swinging bucket ultracentrifuge rotor TST60 (Solvay). The RNAse free centrifugation tubes were filled first with 650 µl of the 30% sucrose mixture—making sure all liquid was assembled in the bottom of the tube—and set at −70 C for 20 min. When frozen, 650 µl of the 26% solution was added and frozen again the same way. This was repeated for the 22%, 18% and 14% sucrose blend. Subsequently the sucrose gradient was stored at 4 C and overlayed with 650 µl of the 10% sucrose solution just before use.

A continuous gradient was formed by incubation at 4 C for at least 12–14 h. The mRNA (dissolved in a final concentration of 1 µg/µl) was denatured at 65 C for 5 min and cooled on ice. 50 µl mRNA solution was carefully loaded on top of the sucrose gradient and the gradient was centrifuged for 15 h. at 34.000 rpm in the TST60 rotor (Solvay). 400 µl fractions were taken from the top by pipette and transferred to an eppendorf on ice. To get rid of the sucrose, the RNA was purified by ethanol precipitation: 1/10 volume of NaOAc (3 M) and 2.5 volumes ethanol were added and the mixture was incubated overnight at −20 C, centrifuged for 15 min at maximum speed in a table-top eppendorf centrifuge, washed with 70% ice cold ethanol, dried on ice and dissolved in $H_2O$.

EXAMPLE 7

Complementary DNA Expression Library Preparation

A cDNA library was made using the Gibco BRL Superscript plasmid system (for an overview see FIG. 4A).

Double Strand cDNA Synthesis

A first cDNA strand was formed starting with mRNA (between 1–5 µg) as template. The primer used in this reaction was a NotI primer—adapter containing 15 dT residues. Primer (1 µg) and mRNA were mixed and heated to 70 C for 10 min and quick-chilled on ice. The buffer (50 mM Tris.HCl (pH 8.3), 75 mM KCl, 3 mM $MgCl_2$, 10 mM DTT), with dNTP mix (final concentration of 0.5 mM of each dATP, dCTP, dGTP, dTTP) were added together with the reverse transcriptase, Superscript II RT (200–1000 units depending on the amount of RNA) and 0.05 µCi of ($-^{32}P$) dCTP as a reporter to trace the cDNA through the procedure. This reaction mix was incubated at 37 C for 1 h. Second strand synthesis was catalysed by *Escherichia coil* DNA polymerase I in combination with *E. coli* RNase H and DNA ligase. Final composition of the reaction was 20 µl of first strand reaction mix plus 25 mM Tris.HCl (pH 7.5), 100 mM KCl, 5 mM $MgCl_2$, 10 mM $(NH_4)_2SO_4$, 0.15 mM $-NAD^+$. 250 µM of each dNTP (dATP, dCTP, dGTP, dTTP), 1.2 mM DTT, 65 U/ml DNA ligase, 250 U/ml DNA polymerase I, 13 U/mi RNase H in a final volume of 150 µl. The reaction was incubated at 16 C for 2 h. Then polymerase 4 was added for a further 5 min at the same temperature. At this point the reaction was stopped with 10 µl of 0.5 M EDTA and extracted with 150 µl of a phenol and chloroform (50/50 v/v) solution. The cDNA was precipitated by adding 70 µl of a 7.5 M $NH_4OAc$ plus 0.5 ml pre-chilled (−20 C) ethanol to the aqueous solution and the mixture was centrifuged for 20 min. The pellet was washed in 70% ethanol, centrifuged for 2 min and finally, after evaporation of the remaining ethanol, dissolved in 25 µl $H_2O$. Adapters were added onto the double stranded cDNA by blunt end ligation in a reaction containing 50 mM Tris.HCl (pH 7.6), 10 mM $MgCl_2$, 1 mM ATP, 5% (w/v) PEG 8000, 1 mM DTT, 200 µg/ml SalI adapters and 100 U/ml T4 DNA ligase. The free terminus of the adapters included a 4 base 5' extension, corresponding to the termini produced by a SalI restriction endonuclease. After digestion with NotI (50 mM Tris.HCl (pH 8.0), 10 mM $MgCl_2$, 100 mM NaCl and 1200 U/ml NotI), the DNA was purified as before with phenol-chloroform extraction and ethanol precipitation.

Column Purification of the Inserts

The DNA was dissolved in 100 µl TEN buffer: 10 mM Tris.HCl (pH 7.5), 0.1 mM EDTA, 25 mM NaCl. A preset column was provided with the system to separate out the cDNA. The column was first prepared with 4 washes of 0.8 ml TEN buffer. The cDNA and an additional wash of 100 µl TEN buffer was drained through the column. The next 100 µl TEN buffer was added and single drop (approximately 35 µl) elutes were collected into separate eppendorfs, this was continued for 3 more 100 µl TEN aliquots. Fractions containing DNA were detected by measuring the radioactive label in a scintillation counter, 3 µl of these were run on a gel to determine the size. The double stranded cDNA of the fraction yielded a broad band consistent with the size of the original mRNA.

Ligation of the Inserts

The cDNA was ligated into the pSPORT1 expression vector which was linearized with NotI-SalI (see below and FIG. 4B). The ligation mix consisted of 50 mM Tris.HCl (pH 7.6), 10 mM $MgCl_2$, 1 mM ATP, 5% (w/v) PEG 8000, 1 mM DTT, 2.5 µg/ml Plasmid pSPORT1, NotI-SalI-cut, 0.5 µg/ml cDNA and 50 U/ml T4 DNA ligase. This mix was added to the cDNA. The ligation mixture was incubated for 3 h at room temperature. To electroporate the DNA into bacterial cells, the ligation mixture had to be desalted by precipitation with ethanol. To the 20 µl of ligation mix; 5 µl yeast tRNA (1 µg/µl), 12.5 µl $NH_4OAc$ (7.5 M), and 70 µl absolute ethanol (−20 C) were added. The mixture was vortexed and immediately centrifuged at 14000 g for 2 min. The supernatant was discarded and the pellet was dried at 37 C for 10 min. The cDNA was dissolved into 6 µl $H_2O$, and 4 electroporation reactions were performed. Each time 1.5 µl ligation mix was added to 40 µl of electroporation cells (ElectroMAX DH10B cells, BRL), incubated on ice for 1–3 min, and transferred to an electropation cuvette (BioRad). The electroporation was carried out with a pulse controller (BioRad) at 200 and a Gene Pulser (BioRad) set to 25 µF and 2,5 V. 1 ml SOC medium was added and cells were incubated for 1 h at 37 C. Part of the library was plated onto LB amp (ampicillin) containing petri dishes (10 times 2000 transformants), the other part of the library was stored in liquid LB or SOC medium as 40% (v/v) glycerol stocks at −70 C.

To test the percentage of selfligants, a fraction of the tranformants was plated out on a LB, amp plate containing X-gal (5-bromo-4-chloro-3-indolyl N-acetyl--D-galactosamidine 40 µg/ml, Sigma) and IPTG (isopropylthio- -galactoside, 40 µg/ml, Sigma). After overnight incubation at 37 C, the colonies containing recombinant clones were white due to inactivation of the -galactosidase gene in the plasmid (see next paragraph). The colonies containing re-circularised vector were blue.

Characteristics of the pSPORT1 Vector

The pSPORT1 vector (FIG. 4B) comprises 4109 base pairs and contains a lacP promoter at one end of the multiple cloning site (MCS). The other lac operon elements (lacO and the -element of the lacZ gene (lacz)) are interrupted by the MCS. The vector also features a laqI repressor gene, so transcription of cDNA inserts by the promoter is effectively repressed, unless 1 mM IPTG is added to the growth medium. Libraries are not plated under inducing conditions unless expression is specifically desired. The SP6 and T7 RNA polymerase promoters can be used to synthesize RNA in vitro from purified plasmid DNA using either SP6 or T7 RNA polymerase. These promoters oppose each other and bracket the MCS so that either strand of the cDNA can be copied into cRNA (see in vitro transcription paragraph, below). The f1 intergenic region (IG) on the plasmid can be used to synthesize the single-stranded form of the plasmid. The plasmid origin site of replication (ori) belongs to the colE1 family. The vector contains an ampicillin resistance gene to select for strains containing pSPORT1.

EXAMPLE 8

DNA and RNA Manipulations and In Vitro Transcription

Plasmid Preparation and DNA Digestion

Plasmid DNA from E. coli colonies was prepared with the Quiaprep spin plasmid kit from Quiagen, which contains columns and buffers needed. The bacteria of a 5 ml prep from an overnight LB culture or cells directly collected from an agar containing LB plate were pelleted by centrifugation at 4500 g for 10 min in a table-top BR401 centrifuge (Denley). The bacterial pellet was dissolved in 250 µl of buffer P1 plus 100 µg/ml RNase, subsequently 250 µl buffer P2 was added, the solution was mixed prior to addition of 350 µl N3. The mix was centrifuged at 10000 g (13000 rpm in a table-top centrifuge) for 10 min. The supernatant was decanted onto a Qiaprep column, and centrifuged at the same speed for 1 min. The column was washed with 750 µl buffer PE and centrifuged again for 1 min. To elute the DNA, 50 µl Tris.HCl (10 mM, pH=8.5) was added onto the column and incubated at room temperature for 1 min followed by a 1 min centrifugation as above collecting the elute into a fresh tube. The DNA was stored at −20 C.

For restriction digests and modifications of DNA, the NEB enzyme system from New England Biolabs was used. All NEB buffers and reaction conditions provided by the company were applied.

DNA agarose gel electrophoresis was used to separate and analyse a fraction of DNA. 0.8–1% agarose was dissolved in 1×TAE (40 mM Tris-acetate. 1 mM EDTA. The gel system and power supply (model 1000/500) from BioRad were used for the electrophoresis. Samples were loaded in a 1×loading buffer (10×loading buffer stock: 0.4% bromophenol blue, 0.4% xylene cyanol FF, 25% Ficoll, Type 400). Once run, the gels were stained in 0.5–1% ethidium bromide solution for 30 min, rinsed with water and DNA was visualized on a UV transilluminator. As a standard, the 1 Kb DNA ladder of Gibco BRL was used. DNA size and concentrations were estimated in comparison with this standard run on the same gel.

DNA purification after digestion was performed by phenol-chloroform (50/50, v/v) extraction(s) followed by a precipitation. Therefore, 1/10 NaOAc (3 M) and 2 volumes of pre-chilled ethanol were added and the mixture was cooled at −20 C for at least 15 min before the DNA was spun down by centrifugation at highest speed possible. After washing with 70% ethanol, the DNA pellet was dried and dissolved in an appropriate amount of water.

In Vitro Transcription

The transcription reaction in vitro, was carried out using the T7 Cap-Scribe pack of Boehringer Mannheim which includes a T7 RNA polymerase and a 10 times concentrated buffer. The buffer contains optimized concentrations of ribonucleoside triphospates and cap-nucleotide mGpppG which ensure that capped mRNA is synthesized.

The reaction was performed with 0.5 Mg linearized DNA as template and was incubated with 1×buffer and 40 units of T7 polymerase for 1 h at 37 C. The reaction was followed by a DNase treatment with 1 unit RNase-free DNase (Promega) for 15 min. A typical yield starting from 0.5 µg DNA template was 10 µg cRNA.

RNA Gel Electrophoresis 1.2 g agarose was melted in 80 ml $H_2O$, in a microwave oven and cooled down to 65 C. 10 ml of a 10 times MOPS stock buffer was added (10×MOPS buffer, 0.4 M MOPS. 6 mM EDTA (pH 8), 50 mM NaAc, final pH 7), and 17.5 ml formaldehyde. This blend was well mixed and pored in gel former (BioRad), cooling to polymerise the agarose and form a gel. The loading mix for the RNA samples consisted of 100 µl 10×MOPS, 350 µl formaldehyde, 1 ml formamide, 200 µl loading dye (50 mg Bromophenol blue and 5 g ficoll mixed in 20 ml water). The RNA sample was dissolved in a volume between 1 and 8 µl, mixed with 16.5 µl loading mix and 2 µl EtBr (0.5 mg/ml) and heated at 65 C for 10 min, then chilled on ice and loaded on the =i gel. The gel was run at 100–150 V in a 1×MOPS buffer for 4 to 5 hours. RNA was visualized onto a UV transilluminator. The size of the RNA fragments was estimated by comparison with the standards of the 0.24 to 9.5 Kb RNA ladder (Gibco BRL).

EXAMPLE 9

Enriching of the RNA for Responsible Transcript by Size Fractionation

In order to narrow down the number of transcripts, the total representation of tobacco leaf mRNA was divided into fractions segregated by size on a continuous sucrose gradient. 100 µg denatured mRNA of the ABA responding sample, was loaded on two gradients and centrifuged for 15 h. 10 fractions of each around 10 µg RNA were recovered starting with the fraction containing the smallest fragments at the top of the gradient. One tenth of each fraction was analysed using a formaldehyde containing agarose gel stained with ethidium bromide to visualize the RNA (FIG. 18). The fractionation by size was clearly seen by the RNA smears on the gel whose size increased with the different fractions. RNA concentrations of the fractions were determined by spottogram, see Example 1, and each fraction was brought to a final concentration of 1 µg/µl after purification by phenol/chloroform and ethanol precipitation.

It was considered that fractions 1 to 3 contained RNA that was too small to be coding for a receptor type protein, and fraction 10 did not contain a sufficient amount of RNA to be injected. Fractions 4 to 9 were injected in Xenopus oocytes (at +50 ng per oocyte). After 2 days of protein synthesis the oocytes were tested for their sensitivity to ABA. Voltage clamp measurements were carried out as described in chapter 3 for total mRNA. Oocytes injected with mRNA from fractions 4,5,7,8 and 9 failed to give a detectable change in current in response to ABA.(average of 3 or more oocytes per fraction, Table 2). Oocytes expressing transcripts of fraction number 6 showed a distinctive signal upon addition of ABA in 3 out of 5 cells. A rise in outward-rectifying current was detected upon depolarisation of the membrane from a holding potential at −120 mV to voltages higher then −10 mV, and the current decayed several minutes (5 min) after the ABA application to the original current level. The transient ABA response for the oocytes injected with mRNA from fraction 6 was similar to the $Ca^{2+}$-dependent outward $Cl^-$ channels recorded for the total mRNA injected oocytes (see paragraph 3.4.2).

The mean of the induced ABA current at +60 mV for each injected fraction is displayed in FIG. 19. The steady-state current as registered during ABA exposure was recorded at the end of the voltage test pulse at +60 mV and was adjusted by subtracting the steady-state current at the same clamp voltage recorded before adding the ABA. A significant increase in current amplitude in response to ABA was detected in the 3 positive cells injected with RNA from fraction number 6. By comparison, the mean induced current for other sucrose gradient fractions fluctuated around zero. The mean of the negative fractions was calculated from all the measured cells (fraction 4, n=6; fraction 5, 7 and 9, n=4; and fraction 8, n=3).

The mRNA fraction giving rise to this positive ABA signal had a bulk smear between 1.5 and 2 kb as seen on an agarose gel (FIG. 18) and it was used for further cloning and sib-selection.

EXAMPLE 10 cDNA Library Cloning

The mRNA fraction number 6 which evoked an ABA response in the oocytes, was used as template to construct a cDNA expression library. The BRL Superscript Plasmid System for cDNA synthesis and plasmid cloning was implemented (for an overview see FIG. 4). 4 μg mRNA was used in the reaction to prepare the first strand cDNA. The primer-adapter used in this reaction consisted of 15 dT residues, which can hybridize the poly(A)$^+$ tail of mRNAs and was attached to a NotI restriction recognition site. The reaction was performed with a reverse transcriptase enzyme (Superscript II RT) which is a derivative of the Moloney Murine Leukemia Virus (M-MLV) and lacks the RNase H activity to increase the yield of full length cDNA.

The primary sequence of the mRNA was recreated as second strand DNA W using the first strand cDNA as a template. The system used nick translation replacement of the mRNA to synthesize the second strand cDNA. Second strand synthesis was catalysed by E. coli DNA polymerase 1 in combination with E. coli RNase H to make the nicks in the mRNA and DNA ligase. This combination has been shown to improve cloning of double-stranded cDNA synthesized from longer mRNAs (±2 kb) (Gibco BRL). The products of second strand synthesis were treated with T4 polymerase to ensure the cDNA strands contained blunt ends.

Directionality in cloning was obtained by introducing asymmetry at the ends of the cDNA, typically by introducing two different restriction endonuclease sites at the termini (FIG. 4). To maximize ligation efficiency into the vector, the blunt ends of the cDNAs were converted to a terminus that contains a 5' extension by adding adapters to the inserts. The used adapters were short, duplex oligomers with one blunt end and with a 4-base, 5' extension at the other end, corresponding to the termini produced by the SalI restriction endonuclease. The blunt end ligation of the adapters was driven by adapter excess. The asymmetric element needed to obtain directional clones was the NotI restriction site introduced into the cDNA by the primer-adapter during the first cDNA strand synthesis. After the ligation of the SalI adapters, the cDNA was digested with NotI. The resulting NotI terminus identified the end of the cDNA corresponding to the 3' end of the mRNA, the other terminus, SalI corresponds to the 5' end of the mRNA.

Before the actual ligation into the vector, the cDNA was fractionated by size on a column provided with the kit. This is important because the residual adapters were present in large molar excess and can impede vector ligation to cDNA by ligating to the SalI terminus of the predigested vector. Additionally, the fragments released from the cDNA by NotI digestion have SalI termini at one end and NotI termini at the other, and could contaminate the library with apparently 'empty' clones, which increases the screening burden. Size fractionation also reduced the tendency of smaller inserts containing incomplete cDNAs to predominate the library.

Finally 13 ng column purified cDNA of the right size (between 1.3–3 kb as verified on agarose gel) was ligated into 50 ng of predigested (NotI-SalI) pSPORT1 expression vector, so that the genes were cloned downstream the T7 RNA polymerase promoter. Transformation of the strain was achieved via electroporation using the ElectroMAX DH10B cells from BRL. A total yield of $4 \times 10^5$ clones was obtained, from which 10% were self ligands. For storage, the transformants were diluted in liquid LB medium ($1 \times 10^4$ cells/ml LB) with glycerol to a final concentration of 40%, and kept at −70 C.

EXAMPLE 11

Sib Selection

70000 Colonies, a Representation of the Library

About 20000 colonies were grown evenly spread onto 10 LB petri dishes containing ampicillin in the LB medium to select for pSPORT1 transformed colonies. Each plate with 2000 colonies was twice replicated onto another plate, using sterilized filter paper. The sib selection is outlined in Table 2. The bacterial colonies of one of the duplicates were scraped of the medium with a glass pipette and dissolved in 10 ml H$_2$O for each plate separately and the pools were numbered from 1 to 10. Cells were collected by centrifugation for 10 min at 4500 g in a table-top centrifige BR401 (Denley). Plasmid DNA was prepared and linearized by NotI restriction digestion. After in vitro transcription the cRNA was pooled into 3 pools, 2 containing around 6000 transcripts (pool 1+2+3 and pool 4+5+6), and the third one about 8000 colonies (pool 7+8+9+10). As control, a representation of cRNA from pool number 1 containing 2000 clones is shown in FIG. 11.

The 3 pools were injected into Xenopus oocytes and, after 2 days of expression, voltage clamp measurements were performed and the response to ABA was tested. The voltage clamp protocol was standard and used through the sib selection. The conditional potential to set a minimum baseline of Cl$^-$ channel activity before the test pulse was set at −120 mV, the 8 test pulses extended from −180 mV to +60 mV and they were followed by a postpulse at −120 mV. One pool of 6000 clones (1+2+3) showed, reaction upon addition of external ABA in 2 of the 4 cells tested. When the membrane voltage was clamped from a holding potential of −120 mV to a pulse of +60 mV a time-dependent current arose in the presence of ABA. The transient ABA induced current amplitude however was very small, in the range of 100 nA (see Table 2). To a first approximation the currents were consistent with the Cl$^-$ current described for the mRNA injected oocytes.

By contrast, oocytes injected with cRNA from the other pools, pool 6000 (4+5+6) and pool 8000 (7+8+9+10), did not show any change in clamp current upon ABA addition (number of cells tested: n=4 /pool) (see Table 2).

Subdivision of the 20000 Library Representation into Subsequent 2000 and 200 Fractions The clone(s) responsible for the ABA sensitivity were isolated by reducing the pool of unique transcripts. The cRNA of 3 pools of 2000 colonies (1, 2 and 3) which were sections of the active pool of 6000 clones (1+2+3) were separately injected into the oocytes. The ABA assay yielded a signal with one (pool number 1) of the 2000-clone pools. Oocytes injected with pool number 1, showed an ABA evoked current increase of −20–50 nA at high positive voltages (+60 mV) when the standard voltage clamp protocol was used (Table 2, FIG. 20). Three cells were tested and all three showed the ABA induced current, indicating the high reproducibility of this small but significant signal. Pools number 2 and 3 when expressed in oocytes did not gave a signal in response to ABA (pool 2, n=5; pool 3, n=6).

An additional sib-selection step was carried out by dividing the active 2000 pool of clones into 8 pools of approximately 200–250 clones. This was performed by cutting up the medium of a replica LB plate containing the 2000 colonies of pool number 1 into 8 pieces. The colonies of each piece were scraped off the medium and dissolved in 10 ml H$_2$O. DNA was prepared and linearized using a NotI restriction enzyme and cRNA was synthesized in vitro, and was injected in oocytes. One pool of 200 clones showed a signal in response to ABA, although it was less persistent in some oocyte batches: 1 positive cell out of 5 was obtained on one occasion and 1 cell out of 3 with another oocyte batch on the second occasion. This pool however revealed very convincing increasing transient current traces in response to ABA in a third oocyte batch, in 3 of the 5 cells tested. ABA induced the current with an amplitude of 300 nA when the membrane was clamped from a prepulse of −120 mV to +60 mV during the application of the standard voltage clamp protocol. The increase in current amplitude with ABA was at least double the size in comparison to the response seen in any previous cRNA injected oocytes (FIG. 20, FIG. 21). Therefore it was thought that an enrichment for the transcript(s) necessary for a functional ABA signal pathway in oocytes was accomplished. All other 7 subpools derived from the positive 2000 pool were negative (Table 2, 3–4 cells tested per pool).

Before continuing, at this stage measurements were repeated to avoid possible complications arising from variations in difference of oocyte batches. All the positive pools were injected separately into a single batch of oocytes. ABA assays tested here confirmed the transient outward current that was small but significant for the positively selected pools all through the sib-selection process (FIG. 20). Table 2 summarizes the cells tested. The pool of 20000 clones gave 2 positive cells out of 2 cells tested with an average induced current of 150 nA; the pool of 2000 clones gave one ABA responsive cell out of the 3 injected oocytes, yielding an induced current of 150 nA. The 200 pool gave 2 positive cells out of 4, yielding an induced current of 200 nA. Another pool of 6×1 transcripts derived from the original cDNA library did not respond to ABA, confirming the specificity of the signal for these particular transcripts (n=3).

20 Difficult Growing Candidates

Individual colonies of the active 200 pool were picked (with sterile toothpicks) and replicated onto a new LB petri dish. Three separate attempts were made to subdivide and assay for a positive ABA response. At first none of the 4 subpools of 50 transcripts gave oocytes responsive to ABA following injections. Only on the third attempt, when a particular subset of 20 colonies was collected and when their cRNA was expressed in oocytes was the signal recovered (FIG. 20 and Table 2). This pool combined all *E. coli* transformants that grew slowly after the replication.

Two independent batches of oocytes were injected with the 20 pool and on one occasion 4 of the 5 cells, on the other 1 out of 2 cells showed a positive ABA response. However, the oocytes did not react upon addition of ABA when injected with the three other 200-pool-derived subpools (n=3–4 /pool of 60 clones). The ABA-induced current amplitude of the 20 pool was also enhanced in comparison with previous detected ABA signals of oocytes injected with 2000 or 20000 transcripts. In one cell an ABA-evoked current of 500 nA was reached at 60 mV, indicating an enhancement of the signal amplitude over oocytes injected with cRNA of the positive 200 pool (FIG. 20, Table 2). On average the amplitude of the ABA assay was increased in the 20 pool (270 nA) over the 200 pool (140 nA).

Fewer Possible Candidates, Greater Conductance

The chord conductance (g) was calculated for the positive cells of each pool (20000-6000-2000-200-20) inducing response to ABA in oocytes. The chord conductance represents the slope of the line fitted through the equilibrium potential for $Cl^-$ $E_{Cl}$ and the ABA induced current at +60 mV. The induced current is the current induced by ABA adjusted by subtraction of the background current present in the oocyte before ABA was added. The mean ±SE of the chord conductance is plotted in a semi-logarithmic scale against the amount of transcripts in the representative pools. The procession of the curve showed an inversely proportional increase in conductance in the ABA response to the number of dissimilar transcripts in the pools. This indicates an enrichment for the ABA perception messenger(s).

TABLE 2

Overview of injected oocytes tested for ABA transient increase in the outward currents during the cloning strategy and sib selection. Highlighted pools were positive and were used for further sib-selection.

| Pool nr | Number of transcripts | Toad nr | Date | $I_{ABA}{}^a$ (nA) | Pos[b] | n[b] |
|---|---|---|---|---|---|---|
| 1 | pos pool 6000 | 1 | 30-4/1-5-95 | 50, 100 | 2 | 4 |
| 2 | neg pool 6000 | 1 | 30-4/1-5-95 | 0 | 0 | 4 |
| 3 | neg pool 8000 | 5 | 15/17-5-95 | 0 | 0 | 4 |
| 1 | neg pool 2000 | 5 | 15/17-5-95 | 0 | 0 | 5 |
| 2 | neg pool 2000 | 5 | 15/17-5-95 | 0 | 0 | 6 |
| 3 | pos pool 2000 | 5 | 15/17-5-95 | 30, 40 | 2 | 2 |
| 1 | pos pool 200 | 6 | 12/13-6-95 | 100 | 1 | 5 |
| 1 | pos pool 200 | 5 | 20/22-12-95 | 250, 200, 150, 120 | 4 | 5 |
| 1 | pos pool 200 | 5 | 27/28-2-96 | 100 | 1 | 3 |
| 2 | neg pool 250 | 6 | 12/13-6-95 | 0 | 0 | 4 |
| 3 | neg pool 250 | 6 | 12/13-6-95 | 0 | 0 | 4 |
| 4 | neg pool 250 | 6 | 12/13-6-95 | 0 | 0 | 3 |
| 5 | neg pool 250 | 6 | 12/13-6-95 | 0 | 0 | 4 |
| 6 | neg pool 250 | 6 | 12/13-6-95 | 0 | 0 | 3 |
| 7 | neg pool 250 | 6 | 12/13-6-95 | 0 | 0 | 3 |
| 8 | neg pool 250 | 6 | 12/13-6-95 | 0 | 0 | 4 |
| — | neg pool 6 × 10[4] | 5 | 28/30-8-95 | 0 | 0 | 3 |
| — | pos pool 20000 | 5 | 28/30-8-95 | 100, 20 | 2 | 2 |
| 3 | pos pool 2000 | 5 | 28/30-8-95 | 150 | 1 | 3 |
| 1 | pos pool 200 | 5 | 28/30-8-95 | 100, 100 | 2 | 4 |
| 1 | pos pool 20 | 6 | 12/14-3-96 | 500, 300, 150, 150 | 4 | 5 |
| 1 | pos pool 20 | 7 | 3/4-6-96 | 250 | 1 | 3 |
| 2 | neg pool 60 | 6 | 12/14-3-96 | 0 | 0 | 3 |
| 3 | neg pool 60 | 6 | 12/14-3-96 | 0 | 0 | 4 |
| 4 | neg pool 60 | 6 | 12/14-3-96 | 0 | 0 | 3 |

[a]$I_{ABA}$ is the ABA induced current at +60 mV as measured for each cell individual.
[b]The number of oocytes responding to ABA (Pos) out of the total number (n) of injected cells tested by voltage clamp.

All procedures used below concerning DNA and RNA manipulations as well as the expression analysis in *Xenopus leavis* oocytes were performed as described before.

EXAMPLE 12

DNA Sequencing

In order to sequence DNA, an ABI PRISM™ 310 Genetic Analyzer (Applied Biosystems, Perkin Elmer. Foster City, Calif.) was used. The 'dye terminator' procedure was followed which makes use of ddNTP's (dideoxi-ribonucleotide triphosphates) labelled with fluorescent label. ddNTP's prevent the DNA polymerase from extending the DNA replication. The ddNTP's were used in a proper ratio with normal dNTP's so that they were incorporated at random positions into copies of the template DNA and resulted in DNA strands of different lengths each labelled at its terminus by a fluorescent ddNTP. The reaction was loaded on a column consisting of a 2 μl gel in a capillary (75 μm diameter). ddNTP's were detected by a laser beam and each ddNTP (ddATP, ddCTP, ddGTP or ddTTP) was read at a different wavelength.

The template DNA was plasmid DNA prepared using the Quiaprep spin plasmid kit from Quiagen. To prepare the samples, a PCR reaction was performed using Taq polymerase. The reaction mixture contained 4.0 μl Terminator Reaction Mix, 0.5 μg template double stranded plasmid DNA, 3.0 pmol primer and was supplemented with water to give a total volume of 10 µl. The template was amplified under the following conditions in a Gene Amp PCR System 2400 (Perkin Elmer, Foster City, Calif.):
1. rapid thermal ramp to 96 C.
2. 96 C for 10 s.
3. rapid thermal ramp to 50 C.
4. 50 C for 5 s.
5. rapid thermal ramp to 60 C.
6. 60 C for 2 min.
7. 1 to 6 was repeated for 25 cycles.
8. rapid thermal ramp to 4 C.

The reaction was purified before loading onto the column. Purification was necessary to remove all excess label. Each tube was supplemented with 10 µl NaOAc (3 M) and 80 µl H2O. The solution was transferred to a 0.5 ml eppendorf containing 250 µl 95% ethanol. The solution was placed on ice for 10 min and then centrifuged in a lab top microcentrifuge at maximum speed for 20 min. All ethanol was carefully removed and the pellet was rinsed with 250 µl ethanol (70%). All ethanol was again removed. The pellet was resuspended in 12.5 µl template suppression reagents (Perkin Elmer, Foster City, Calif.) by thoroughly vortexing the tube, heating the reaction for 2 min at 95 C and vortexing again. After the solution was spun down briefly, the reaction in the tube was ready to be loaded onto the column of the Genetic Analyzer.

Primers

The T7 primer is a 20 mer: 5'-TAATACGACTCACTATAGGG-3' (SEQ ID NO:41) M13(f) is a sequence primer (7 mer): 5'-GTAAAACGACGGCCAGT-3' (SEQ ID NO:42)

EXAMPLE 13

Sequencing Analysis

The Lasergene software from DNA* (Madison, USA) in parallel with ABIView v 1.0 (Perkin Elmer, Foster City, Calif., Copyright David H. Klatte, 1996) was applied to analyse the sequences. ABIView is a program that displays the unedited traces of the sequences directly recorded from the Genetic Analyzer. The plain sequence was copied in EDITSEQ, a subprogram of Lasergene where sequences were edited and translated. Once the sequence was stored as a EDITSEQ file, access to all the following subprograms of Lasergene was available. SEQMAN was used to make a contig from overlapping sequences. MAPDRAW was used to determine open reading frames and to register restriction endonuclease sites. MEGALLIGN was used to allign different known sequences at nucleotide and amino-acid level and calculate the percentage similarity between them. Similarity was calculated from the amount of identical amino acid residues in relation to the total length of two protein sequences. PROTEAN was used to analyse the predicted protein sequence at structural level, including hydrophobicity plots and, at the sequencing level, including identification of possible conserved functional domains.

Sequence homology searches were performed at the BLAST sequence similarity service, provided by NCBI (National Centre for Biotechnology Information, described in detail previously herein).

EXAMPLE 14

ABA Signal was Lost Beyond the Pool of 20 Clones

Plasmid DNA was prepared from all the 20 single colonies. Five pools of each four clones were formed by pooling equal amounts of DNA together, and cRNA was synthesised in vitro. The cRNA samples were injected in oocytes. After expression, the oocytes were tested for ABA response as described above. No significant ABA response could be found in a total of 9 cells spread over four of the five pools. One pool was correlated with some fluctuation in outward-rectifying current (less than 50 nA) in 2 of the 3 cells tested from this pool, but ABA specificity was not clear. To test the significance of these currents, the 4 single cRNA's of this last pool of clones were injected in oocytes. Again, no ABA response was detected (n=2 cells per clone). One of the cRNA samples, however, yielded significant currents, although not dependent on ABA.

EXAMPLE 16

Combinations of Clones could not Rescue the Signal

A cRNA combination of smG-Nt (the small G-protein-like) (SEQ ID NO: 14) and the cal-Nt (the calreticulin-like) (SEQ ID NO:20) together with the syr syntaxin-like clone (SEQ ID NO: 1) in a relative concentration of 1 (smG-Nt): 1 (cal-Nt): 0.1 (syr), was expressed in oocytes. Some current fluctuation associated with to the syntaxin-like clone was detected but no measurable response to ABA was recorded. This was tested twice in different oocyte batches with $n_{total}=7$. Also when the three unknown membrane proteins of clones number 2, 8 and 12, together with the syntaxin-like protein were coexpressed with a ratio of (1(2):1(8):1(12) :0.1(syr)) in oocytes, no ABA signal was recovered. This was also tested on two separate occasions with $n_{total}=4$.

All experimental procedures concerning electrophysiological recordings and DNA sequencing used in this chapter were described before.

EXAMPLE 17

Subcloning

Ligations

DNA manipulations were used as described above. After running the agarose gel, the fragment and vector were purified using the 'Agarose gel DNA extraction kit' from Boehringer mannheim which makes use of a specially treated silica matrix which binds nucleic acids, contamination was washed away, and finally, elution of DNA was obtained in 50 µl of a 10 mM Tris.Cl (pH 8) solution. T4 DNA Ligase (Boehringer Mannheim) was used to ligate DNA fragments into plasmids. The ligation buffer contained 50 mM Tris.Cl (pH 7.5), 10 mM $MgCl_2$, 10 mM DTT, 1 mM ATP and 25 µg/ml BSA. The reactions containing 5× the molarity of insert versus vector were incubated overnight at 17 C.

Transformations

The ligation mixtures were transformed into E. coli electrocompetent cells. The electrocompetent cells were prepared from the E. coli strain DH12S. One single colony was picked and incubated in a 10 ml SOB-Mg at 37 C overnight. 500 ml SOB-Mg was inoculated with 5 ml of the overnight culture and bacteria were grown at 37 C until the $OD_{550}$ reached 0.75. The cells were spun down in a GSA rotor centrifige (SORVAL), at 4000 g. The pellet was washed twice in 400 ml ice cold 10% glycerol and resuspended in 2 ml 10% glycerol. The highly concentrated solution was stored in 100 µl aliquots in eppendorfs at −70 C after quick chilling the tubes in liquid nitrogen.

In order to electroporate in E. coli cells, the ligation mixture had to be depleted from salts. A little column was prepared using a 0.7 ml tube with a hole pierced into the bottom. The bottom of the tube was filled with glass beads (equilibrated in water) and the rest of the tube was filled with Sepharose CL6B (equilibrated in water). The tube was placed in a bottomless 1.5 ml eppendorf and centrifuged for 700 g (2000 K in a lab top centrifuge Denley BR401the tubes were placed in a 10 ml tube for support) for 2 min. The bottomless tube was replaced with a fresh tube and the ligation mixture was carefully applied on top of the sepharose. The tubes were spun for 2 min as before. The effluent contains the purified DNA.

Half the volume of the ligation mixture was added to 40 μl of electrocompetent *E. coli* cells, incubated on ice for 1–3 min, and transferred to an electropation cuvette (BioRad). The electroporation was carried out with a pulse controller (BioRad) at 200 and a Gene Pulser (BioRad) set to 25 μF and 2,5 V. 1 ml SOC medium was added and cells were incubated for 1 h at 37 C. The suspension was plated onto LB medium containing the appropriate antibiotic. In case of the pBLUESCRIPT vector, the test for selfligants was performed by plating the transformants out on LB medium containing X-gal (5-bromo4-chloro-3-indolyl N-acetyl--D-galactosamidine 40 μg/ml, Sigma) and IPTG (isopropylthio- -galactoside. 40 μg/ml, Sigma). After overnight incubation at 37 C, the colonies containing recombinant clones were white due to inactivation of the -galactosidase gene in the plasmid. The colonies containing re-circularised vector were blue.

Vectors and Primers

Constructs used

| | Characteristics | Reference |
|---|---|---|
| Vector | | |
| pBluescripts | SK(+), amp$^r$, colE1 origin, f1(+) | Stratagene |
| psyr | Library clone in pSPORT1 (NotI-SalI) | this work |
| psyrbb | psyr BglII-BamHI | this work |
| psyrse | psyr SacI-EcoRI | this work |
| psyr2 | BglII-SacI fragment of psyr cloned into pBluescript | this work |
| Primers | | |
| M13(f) | 5'-GTAAAACGACGGCCAGT-3' | Stratagene |
| M13(r) | 5'-GGAAACAGCTATGACCATG-3' | Stratagene |

EXAMPLE 18

A Second Screen was Applied in Xenopus Oocytes
Primer M13(f)=SEQ ID NO:42; Primer M13(r)=SEQ ID NO:43

As mentioned above, one of the single clones, psyr, yielded a current when its protein was expressed into oocytes. An important difference between this psyr current and the one seen when mRNA of tobacco leaves or cRNA of the positive 20 pool was injected, was the independence of the presence of ABA in the normal Ringer solution. The oocytes, injected with 50 ng cRNA and expressing the SYR protein were impaled with two micro-electrodes. Voltage clamp cycles were recorded with approximately 5 min intervals. The voltage clamp protocol consisted of a pre and post potential of −120 mV for 500 ms and 8 test pulses of 1500 ms ranging between −160 mV and +60 mV. Slowly after impalement, an outward-rectifying current was recorded when the membrane was clamped to voltages higher then −50 mV. The currents measured during the first voltage clamp cycle were minimal, but the current increased over time as recorded by following voltage clamp cycles. This increase in outward-rectifying current was best noticed when the membrane was clamped at +60 mV and was recorded in all the cells tested (n=10 using 3 different batches of oocytes). The current at +60 mV over time after impalement for one oocyte is illustrated in FIG. 22. The increase in current showed an estimated half time of 20 min on average and the highest maximum value recorded was 3 VA. The current seem to exist of two components, a time dependent ($t_{1/2}$ of approximately 200 ms at +60 mV) and an instantaneous component. Both components are rising in time after impalement.

The ABA dependency was not clear as these currents did fluctuate and sometimes the currents were stable for some minutes and then started rising again. Therefore it was impossible to conclude whether these currents were ABA dependent. To circumvent this problem, a dilution was made of the syr cRNA and injected in oocytes. The cRNA (1 μg/μl) was 10 times diluted to inject an amount of approximately 5 ng into oocytes. Voltage clamp analysis of these oocytes showed still the same current as when 50 ng was injected, but the rise in outward rectifying current was slower ($t_{1/2}$ was never determined as the currents were still increasing when finishing the experiment) and the highest maximum recorded was 1.5 μA at +60 mV ($n_{total}$=4). The fluctuations of the currents were still too high to record conclusive data about ABA dependency. Further dilution (1/100) of the syr cRNA was also injected (approximately 0.5 ng), but again, the current was visible although the maximum did not exceed 1 μA at +60 mV ($n_{total}$ =5). No ABA dependency was detected.

To investigate whether the SYR protein was interacting with another protein of the 20 pool, several coinjections were performed. Two combinations were described above. On one hand, cRNA of syr (1/10) with cRNA of the smG-Nt and the cal-Nt were coinjected on the other hand cRNA of syr (1/10) was combined with three unidentified proteins. Both coexpression experiments did not reveal conclusive data for ABA dependency, mainly because of the background currents as typically seen for syr injected oocytes. A last combination was tried with subpools of all 20 candidates from the last ABA responsive pool. Five subpools of the 20 positive pool of clones, were injected each in combination with cRNA of the syr gene. Assays for an ABA dependent signal were tested on at least 3 cells for each subpool, but again fluctuations caused by the SYR protein expression made the results ambiguous.

EXAMPLE 18

Current Characterization Shows Activation of Endogenous K$^+$ Channels in SYR Expressing Oocytes In order to unravel the nature of the increasing current seen when oocytes were expressing the SYR protein, two different strategies were used. Initially the equilibrium potential was analysed for changing external ion concentration, and additionally toxins were used inhibiting specific ion channels.

Reversal Potential and Sensitivity on External K$^+$ Concentration

The first strategy implies the dependency of the current and reversal potential on changes of external ion concentrations. Oocyte expressing the SYR protein were impaled with two electrodes while the chamber was filed with normal Ringer buffer. 30 min after impalement, the currents became more stable and fluctuations in the currents smaller. At that point a standard voltage clamp cycle was applied (pre and post potential at −120 mV for 1 s, and 8 test pulses ranging between −160 mV and +60 mV for 3 s). FIG. 23A displays the current traces when the standard voltage clamp cycle was performed in normal ringer with a potassium concentration $[K^+]_o$ of 2.5 mM. Subsequently the $[K]_o$ in the bath solution was raised 10 fold to 25 mM. The current traces according with the standard voltage clamp protocol are also displayed in FIG. 23A. The currents were sensitive to the changes in external $[K^+]_o$. The time-dependent current did not change significantly, but the instantaneous component increased dramatically, more then two fold at +60 mV. This is best obsserved when the Iv-curves of the total steady state currents were displayed (FIG. 23B). This current increase was reversible. When the bath solution was changed back to normal Ringer, the current decreased back to its original level.

To ascertain the ion by which the current is carried, the reversal potential was experimentally determined and compared with the theoretically calculated equilibrium potential for $K^+$. The equilibrium potential of $K^+$ as measured with the Nernst equation (formula 3.1) for oocytes in normal Ringer solution is −95 mV. When the external bath concentration of $K^+$ is 25 mM. $E_K$ equals −35 mV. An initial indication for a shift in $E_K$ when $[K^+]_o$ is changed from 2.5 mM to 25 mM is illustrated in FIG. 23B. The fitted IV-curve through representative current values at fixed voltages crosses the X-axes at the equilibrium potential. The fitted IV-curve for the data points in normal Ringer conditions crosses the X-axes at approximately −90 mV. The fitted curve of the data points in 25 mM $K^+$ has shifted so the crossing with the X-axes now lies at about −40 mV. These values are consistent with the respective $E_K$ calculated for similar conditions.

In order to determine more accurately the experimental reversal potential, the oocytes expressing the SYR protein was clamped at a prepulse of +50 mV for 1 s to activate the current. Subsequently the membrane was stepped to voltages ranging from −160 mV to +30 mV. In normal Ringer conditions (2.5 mM $K^+$) the current relaxed negative-going at voltage from +30 mV to −65 mV and the current relaxed (tailed) positive going at voltages from −97 mV to −160 mV. The current reversed direction at the reversal potential (see paragraph 3.3.1) and is determined to lie here between −80 mV and −97 mV (FIG. 24), consistent with the predicted $E_K$; (−95 mV). The same voltage clamp protocol was repeated this time with $[K^+]_o$ at 25 mM. The current tailed negative-going at voltages from +30 mV to −3 mV and the current tailed positive-going at voltages −65 mV to −160 mV. At a voltage of −35 mV, no clear relaxation was observed, therefore the reversal potential was determined around −35 mV (FIG. 24), consistent with the predicted shift and $E_K$ (−35 mV). The current yielded by expression the SYR protein in oocytes was mainly carried by potassium.

EXAMPLE 19

Toxins that Inhibit Currents

One of the methods applied to analyse unknown currents in oocytes implies the use of toxins which inhibit currents specifically dependent on the ion by which the current is carried. The toxins used together with their active concentrations are outlined in Table 3.

TABLE 3

Channel inhibitors

| Toxin | Specificity | Active conc | Supply |
|---|---|---|---|
| TEA | very specific $K^+$ channel blocker | 30 mM | Sigma |
| $Ba^{2+}$ | $K^+$ channel blocker with possible side effects as it can substitute for $Ca^{2+}$ | 1 mM | $BaCl_3$; Sigma |
| Niflumic acid | Anion channel blocker, fairly unspecific, can partially block $K^+$ channels | 1 mM | Sigma |
| ω-Conotoxin | $Ca^{2+}$ (type N) channel blocker | 1 mg/ml | Alomone Labs (Jeruzalem, Isreal) |

Pharmacological data support the previous observations that the current detected in SYR expressing oocytes is mainly carried by $K^+$. Several toxins with each distinct specificity were added to the Ringer solution in the bath while clamping the membrane of the oocyte using the standard voltage clamp cycle as in the previous paragraph. Changes in the current traces were recorded and are displayed in FIG. 25.

(1) Initially 30 mM of tetraethyl ammonium (TEA) was added to the Ringer solution by changing only the $Na^+$ concentration. TEA is a toxin that specifically inhibit the $K^+$ channels. Both the time-dependent and instantaneous components are reduced by 50%. The TEA effect was reversible.

(2) $Ba^{2+}$ is also a typical $K^+$ channel blocker, but it may have some complications as it also influences the characteristics of $Ca^{2+}$ channels by substituting for $Ca^{2+}$+. The effect of $Ba^{2+}$ resulted in a conversion of the instantaneous component into the time-dependent component. Full recovery was detected when the $Ba^{2+}$ was washed away. A similar phenomenon has been described before for the $K^+$ channel TOK1 from S. cereviciae. When expressed in Xenopus oocytes, the Tok1 current rectified strongly outward, and this current consisted of two kinetic components. When $Ba^{2+}$ was applied, the instantaneous component was inhibited in favour of the time-dependent component.

(3) Another toxin applied was niflumic acid. This toxin is rather non-specific, it inhibits anion channels as well as $K^+$ channels. The currents detected with the SYR expressing oocytes were also abolished by this toxin, almost 100%. The reduction was fully recovered when the niflumic acid was washed away.

(4) The last toxin used in this experiment was ω-conotoxin, a specific $Ca^{2+}$ channel blocker. It is previously shown that the SYNTAXIN proteins of mammalian cells are associated with $Ca^{2+}$ channels type N. Therefore, we tested whether this current can be abolished with a typical N-type $Ca^{2+}$ channel blocker. However, no effect was detected, the current recorded was not related with $Ca^{2+}$ channels, indicating different regulation of the SYNTAXIN proteins of mammalian cells with the SYR gene of *Nicotiana tabacum*.

Water Injected Oocytes

To test whether the uninjected oocyte is capable of displaying this current, a 25 mM $K^+$ concentration was applied in the bath. The currents that arose were instantaneous, no time-dependent component was seen. The currents were abolished by niflumic acid. $Ba^{2+}$ had a similar effect as described before, elimination of the i, instantaneous current and a time-dependent one arose. The effect of TEA was invisible as the current was too small. These small but significant effects of the change in potassium concentration and toxins indicate that at least the instantaneous component is a current endogenous to the oocytes. The time-dependent component on the other hand seem to be specific for the SYR injected oocytes. It appears that the SYR protein by its association to the endogenous $K^+$ channel not only increases the magnitude of the current but also alters the kinetics.

EXAMPLE 20

Depletion

To circumvent the problem of the loss of ABA response, the involvement of SYR was tested in another way. The idea behind the following depletion experiment was to get a loss of ABA response when the SYR gene was eliminated from a pool of transcripts that originally gave a positive ABA response when expressed in oocytes. The last pool of 20 clones was reconstructed by mixing plasmid DNA of the 18 clones (Table 1, number 10 and 17 were omitted). In a separate preparation, DNA of 17 clones was mixed, which were the same clones as before except for the syr gene. From both newly formed groups, called 18+S and 17–S respectively, cRNA was synthesized in vitro and injected into oocytes. After expression, voltage clamp analysis was performed to test for ABA response. The oocytes expressing the 17–S did not show current or membrane voltage fluctuations, neither without or with ABA in the bath solution. The oocytes expressing the 18+S did not show an ABA triggered signal as seen before. The current fluctuations caused by SYR were seen again, this time faint and delayed for several minutes and not detected in 100% of the cells, but in only 2 of the 4 cells measured. Three of the 4 cells showed some response to ABA. The response was not seen in the current traces during the voltage clamp cycles, but in a slight depolarization of the free running membrane potential. This depolarization ranged between 0.5–2 mV, which is small but it was reproducible and specific for the 18+S pool. Therefore it seems that the SYR protein is necessary for the transmission of the ABA signal.

EXAMPLE 21

Guard Cell Voltage Clamping

The basics behind the voltage clamp technique for guard cells is the same as for Xenopus oocyte voltage clamping (above). The major technical differences on chamber and microelectrodes are outlined below.

Mounting Tissue on a Specially Designed Chamber

The plants used for the guard cell voltage clamp experiment, were either *V. faba* or *N. benthamiana*. Growth conditions were 18 C for *V. faba* and they were grown on vermiculite with a 12:12 day-night cycle. The *N. benthamiana* plants were grown at 20 C with a 12:12 day-night cycle, on soil under a plastic hood to maintain high humidity.

The younger leaves of 4–6 weeks old plants were used to prepare epidermal strips. Strips were taken from the abaxial surface of the leaves and mounted onto the chamber which was coated with pressure-sensitive silicon adhesive (No. 355 medical adhesive, Dow Coming, Midland, Mich., USA). The glue was allowed to dry for approximately 15 min, the epidermal strip was stuck, external face down on the chamber bottom. The chamber bottom consisted of a piece of microscope slide (approximately 0.5 mm thick by 7 mm wide by 40 mm long) with two stainless steel blocks glued at either end. The strip was immediately covered with 0.1 mM KCl in 5 mM $Ca^{2+}$ MES and a coverslip was mounted on top of the solution supported by the two steel blocks. Solution flow accession and suction was obtained by pasteur pipettes drawn to a fine point. Standard solution used was 5 mM $Ca^{2+}$ MES and 10 mM KCl. An agar (2%) salt (1 M KCl) bridge in a tube was applied via a hole through one of I; the steel blocks and serves as the bath electrode. The microscope used was a Zeiss IM inverted microscope (Zeiss, Oberochen, FRG).

The Microelectrode

Electrodes were pulled from triangular cross-section capillary borosilicate glass with a wall thickness of 0.25 mm and an overall cross-sectional diameter of 1.2 mm (Dial Glass Works, Stourbridge, West Midlands, UK). The electrodes were pulled using a horizontal puller (Narashige Scientific Instrument Lab, Tokyo, Japan). The two capillaries were softened by heating for approximately 30 s, then they could be twisted through 360 C. To pull the fused capillaries, an initial weak sensing pull was applied until the capillary had stretched to a pre-determined length, when a second stronger final pull was initiated. Current supply to the heating coil was switched off at this time, allowing the glass to cool as it was pulled out. Current-passing and voltage-recording barrels of the electrodes were filled with 200 mM $K^+$- acetate (pH 7.5). Similar halfcells as for the oocyte voltage clamp were used but they were filled with 1 M KCl.

Botulinuin Toxinis Type C and D

In order to test the effect of botulinum toxin C, the guard cells were loaded intracellularly with the toxin (BotN/C or BotN/D as control) endopeptidases (Sigma). The toxins were included in the filling solution of the current-injecting electrode, and allowed ti diffuse into the cell for 20 min after impalement. Thereafter, the cell was tested for its ABA response while clamping the membrane at different voltages. A standard concentration of 100 nM for BotN/C and 100 nM BotN/D was used.

EXAMPLE 22

Southern Hybridisation

DNA Preparation

DNA was prepared from *N. tabacum* which were grown as outlined before, *N. Benthamiana* grown on soil at 20 C with 12:12 day-night and from *A. thaliana* grown on soil at 22 C with 16:8 day-night cycle.

DNA preparations from plants were performed on 5 g fresh tissue weight which was ground thoroughly with a mortar and pestle while frozen in liquid nitrogen. The powdered tissue was transferred into a 30 ml polypropylene tube containing 15 ml Extraction buffer (100 mM Tris.Cl pH 8.0, 50 mM EDTA pH 8.0, 500 mM NaCl, 10 mM mercaptoethanol). 1.2 ml of 20% SDS was added and after thoroughly mixing, the tubes were placed at 65 C for 10 min. 5 ml of 5M potassium, acetate was added and the tube was shaken gently and incubated on ice for 20 min. Most proteins and polysaccharides were removed as a complex with the insoluble potassium dodecyl precipitate. The tubes were spun for 10,000 rpm in a SS34 rotor (12000 g, Sorvall) and the supernatant was filtered with a Mirecloth filter. To the clear supernatant, in a fresh tube (50 ml), 10 ml isopropanol was added. The DNA which was precipitated could be spooled out with a flamed pasteur pipette. The DNA was dried whilst on the pasteur pipette and the pellet was dissolved in 3 ml water. After adding 20 µl RNAse (10 mg/ml), the DNA was incubated at 37 C for 30 min. The DNA was further purified by extracting with 1.5 ml phenol and 1.5 ml chloroform. After centrifugation for 15 min at 5000 g, the aqueous phase was removed and extracted with 3 ml chloroform as before. The DNA was precipitated with 0.8 volumes of isopropanol and 0.2 volumes of 3 M NaOac. The DNA was spooled again on a pasteur pipette, washed in 70% ethanol, dried and dissolved in 100 µl. DNA concentration was determined by diluting at a rate of 10 µl in 990 µl water and by measuring the OD at 260 nm. The concentration was calculated using the conversion factor where $A_{260}$ of 1.0=50 µg/ml DNA.

Blotting of the DNA onto a Filter

The DNA that was to be probed, was digested with the appropriate restriction endonucleases and separated by electrophoresis on an agarose gel. Once the gel was photographed on the UV transilluminator, the excess gel was trimmed away to blot the DNA onto a membrane. The gel was oriented by cutting off the bottom left hand corner. The DNA in the agarose gel was first depurinated by treating it in 0.25 M HCl for 15 min and rinsed in water. The blotting set up consisted of a bath with 200 ml of 0.4 M NaOH, covered with a glass plate. Two pre-wetted 3 MM filter papers (Whatmann) were cut and hung over the edges of the plate into the solution and were functional as wicks. The gel was placed (upside down) onto the wicks making sure no air bubbles slipt in, because they would prevent DNA transfer. A piece of nylon membrane (blotting membrane, BDH), the size of the gel, was laid on the surface of the gel, and air bubbles removed by rolling with a glass pipette. The areas of the wicks which were not covered by the gel were sealed with plastic foil. Two pre-soaked and 3MM papers were cut to gel size and laid on top of the filter, followed by a 5–10 cm high wad of absorbent paper towels, a glass plate and a 500 g weight. The transfer was left overnight. The dehydrated gel and filter were carefully turned over and laid, gel side up, to mark the positions of the slots onto the filter with a pencil. The filter was washed with 2×SSC (1×SSC=0.15 M NaCl, 0.015 M trisodium citrate) and air dried for 1 h on 3 MM paper. The filter was then wrapped in plastic foil, and the DNA cross-linked to the membrane by placing the filter on a UV-transilluminator, DNA side down, for 2–3 min.

Probe Labelling

The DNA fragment used as a template was purified from agarose gel with the Boehringer mannheim 'Agarose gel DNA extraction kit' (chapter 6). 50 ng fragment was dissolved in 34 µl water, and denatured by boiling for 5 minutes and quick chilling on ice. To the DNA 10 µl reagent mix (Pharmacia Oligo labelling kit), 1 µl of Klenow enzyme (Pharmacia Oligo labelling kit) and 5 µl $^{32}P$ dCTP (Amersham) were added. This reaction mix was incubated at 37 C for 1 h. Then the probe was purified from free label with a little column that was prepared using a 0.7 ml tube with a hole pierced into the bottom. The bottom of the tube was filled with glass beads (equilibrated in water) and the rest of the tube was filled with Sepharose CL6B (Pharmacia) also equilibrated in water. The tube was placed in a bottomless 1.5 ml eppendorf and centrifuged for 700 g (2000 rpm in a lab top centrifuge Denley BR401, the tubes were placed in a 10 ml tube for support) for 2 min. The bottomless tube was replaced with a fresh tube and the probe mixture was carefully applied on top of the sepharose. The tubes were spun for 2 min as before. The effluent contained the purified DNA probe. The probe was then denatured by boiling for 5 min at quick chilling on ice.

Hybridization

The filter to be hybridised was first prehybridised for 2 h at 65 C (or different when indicated). The prehybridization buffer consists of 6×SSC, 5×Denhardt's (acts as blocking agents) and 0.1% SDS plus 100 µg/ml denatured sperm DNA. After the prehybridization, the buffer was discarded and new hybridization buffer was added: 6×SSC, 0.1% SDS, 5×Denhardt's plus the denatured probe. Hybridization was carried out for at least 16 h and at 65 C unless otherwise indicated. The filters were then washed to get rid of background label. Washing occurred twice for 10 min with 2×SSC and 0.1% SDS at 65 C (unless otherwise indicated).

The filter was then exposed to a X-ray film (Kodak XAR-5; IB 165-1678) in a cassette containing intensifying screens (DUPONT Cronex lighting plus, or Fuji High Speed X) at −70 C. The exposure time was dependent on the intensity of the radioactivity measured on the filter with a minimonitor. After the estimated time, usually between 12 hours or 5 days, the X-ray film was developed.

EXAMPLE 23

Northern Hybridisation

The RNA used for Northern blotting was either mRNA, purified as before or total RNA, purified as follows. All aqueous solutions used were pretreated with DEPC (0.001%) which was added to the solution, incubated overnight at room temperature, and autoclaved for 20 min at 120 C and 1 bar. Tris solutions which can not be DEPC treated were prepared with DEPC treated $H_2O$ and autoclaved as above. All plastic material used was direct from the manufacturer and handled with disposable gloves only. 5 g of fresh tissue was grinded thoroughly with a mortar and pestle and kept frozen in liquid nitrogen. The powder was transferred to a fresh 50 ml disposable tube containing 15 ml extraction buffer (100 mM Tris.Cl pH 9.0, 200 mM NaCl, 5 mM DTT, 1% sarkosyl, 20 mM EDTA) and shaken until the powder was thawed and suspended. 7 ml phenol and 7 ml chloroform was added to the mixture, the tube was inverted a few times and centrifuged at 3000 rpm (4000 g) for 10 min in a bench top centrifuged (Denley BR401). The aqueous phase was transferred to a clean tube and the extraction repeated twice with 15 ml chloroform. The volume of the aqueous phase was measured and LiCl was added to a final concentration of 2 M (stock 10 M LiCl). The solution was mixed and incubated at 4 C overnight in corex tubes covered with parafilm. The tubes were then centrifuged at 4 C for 10 min at 10000 rpm (12000 g) in a SS34 rotor (Sorvall). The supernatant was removed and the pellet was washed twice with 2 ml of 2 M LiCl and centrifuged as above. The RNA was finally dissolved in 1 ml RNase free water. RNA concentration was determined by diluting at a rate of 10 µl in 990 µl water and by measuring the OD at 260 nm. The concentration was calculated using the conversion factor where $A_{260}$ of 1.0=40 µg/ml RNA.

RNA Transfer from a Formaldehyde Gel to a Filter

The RNA to be probed was loaded onto a formaldehyde-containing gel. The gel was prepared from 1.2 g agarose that was melted in 75 ml water in a microwave. When the solution was cooled down to approximately 50 C, 10 ml of 10×MOPS (10×MOPS: 0.4 M MOPS, 0.5 M EDTA pH 8, 50 mM NaOac) and 15 ml formaldehyde was added. The mix was swirled and poured into a gel tray. Meanwhile the samples were prepared for loading: 16 μl of loading dye (100 μl MOPS, 350 μl formaldehyde, 1 ml formamide, 200 μl loading mix (loading mix: 50 mg bromophenol blue, 5 g ficoll 400 in 20 ml) was added to 2 μg of mRNA and 15 μg of total RNA and the RNA was denatured at 65 C for 10 min. The samples were then cooled on ice and loaded on the gel. After electrophoresis, the gel was prepared for blotting by photographing the gel on a UV transilluminator and trimming off the spare tracks together with the left bottom corner. The gel was rinsed in 2×SSC and the set up for RNA transfer to nylon membrane (blotting membrane BDH) was the same as for the southern blot, except the transfer buffer which was 10×SSC for a Northern blotting (RNA). After the overnight transfer, the filter was rinsed in 2×SSC and air dried for 1 h on 3 MM paper. The filter was then wrapped in plastic foil, and the RNA cross-linked to the membrane by placing the filter on a UV-transilluminator, RNA side down, for 2–3 min.

The filter was ready for hybridization. The labelling of the probe and the hybridization conditions were identical to the ones for the southern hybridizations.

EXAMPLE 24

Western Hybridization

Choice of Peptides

The first peptide, SP1 consisted of a 13 amino acid long antigenic stretch of the SYR amino acid sequence (SEQ ID NO:2). Because of the small size of the peptide, it was conjugated to a keyhole limpet haemocyanin (KLH). KLH is routinely used as peptide-carrier protein and is hardly antigenic. The peptide conjugate was ordered from Pacemaker (Exeter, UK). Peptide: KLH-CGPGSSSDRTRTS (SEQ ID NO:44)

To purify the second peptide, SP2, the Qiaexpress system of Quiagen was selected. The peptide purification mechanism consist of three major steps: (1) cloning a nucleotide sequence stretch into the expression vector, (2) expressing the peptide and (3) purifying the peptide.

(1) The hydrophilic part of SYR was purified by PCR. Two primers were created. The first one, STX1 was specifically designed to anneal the antisense strand of the SYR at the transcription site and was preceded by a BamHI restriction digest recognition site. The second one, STX2 was specially designed to anneal to the sense strand of the SYR sequence at the C-terminal region of the hydrophilic part of the SYR sequence and was followed by a stop codon TAA and a EcoRI recognition site. The PCR conditions were standard: the PCR reaction buffer: 5 mM $MgCl_2$, 100 mM NaCl, 10 mM Tris.Cl (pH8.4) (Biolabs), supplemented with 20 μM of each primer, 0.25 mM of each dNTP, and 2 units of TaqI (Biolabs). The template used was 1 ng/μl psyr (plasmid prep). The reaction conditions: 30 s at 96 C, 30 cycles of 30 s at 96 C, 30 s at 55 C and 1.5 min at 72 C followed by a final step at 72 C for 5 min. The PCR fragment was gel purified (Boehringer Mannheim 'Agarose gel DNA extraction kit') and digested with BamHI and EcoRI to create sticky ends. After purifying the fragments on a sepharose CL6B column (same as for probe purification), the fragments were ready for ligation into the expression vector pQE-30 (ampicilin resistant) which was pre-digested with BamHI and EcoRI (ligation and transformation were performed as described above) resulting in the new construct pQES (FIG. 7.1). Thus, the pQES vector contained in front of the SYR fragment and in frame, the codons for 6 histidine residues. Upstream of the cloned fragment was a T5 promoter localised, which is inducible by IPTG. Also present were two lac operator sequences which increase lac repressor binding and ensure efficient repression of the T5 promoter in the absence of IPTG. Downstream the cloned fragment were translation stop codons introduced and two strong transcriptional terminators $t_o$ and $T_1$ to prevent read-through transcription and ensure stability of the expression construct. The E. coli strain M15[pREP4] was used to transform the constructs in. This strain contained a plasmid pREP4 (kanamicin resistant) with the lac repressor, to regulate and repress the T5 promoter. The E. coli M15 strain was selected to permit high levels of protein expression.

(2) To express the protein, 10 ml LB Amp (100 μg/ml), Km (25 μg/ml) was inoculated with M15[Rep4][pQES] and incubated overnight at 37 C. 10 ml was diluted into a preheated culture of 500 ml LB Amp Km, and after 4 h of incubation at 37 C, 2 mM IPTG was added. The cells were harvested 4 h later by centrifugation.

(3) For purification of the peptide, the cells were first lysed, then the soluble fraction was run over a $Ni^{2+}$ column to isolate the peptide. The pellet was dissolved in 14 ml (4 ml/gram wet weight) sonication buffer (50 mM $NaH_2PO_4$, 300 mM NaCl, pH 8). The sample was frozen overnight at –20 C. After the sample was thawed in cold water, it was sonicated with a SONIPREP 150 (MSE, Leicestershire, UK) on ice for 5 times one min at 20 amplitude microns until the cells were lysed. To reduce the viscosity of the solution, the RNA and DNA was broken by flushing the solution up and down through a needle. The suspension was centrifuged at 9500 rpm (10000 g) in a SS34 rotor (Sorvall), for 20 min at 4 C. The supernatant was collected in a fresh tube. Meanwhile the $Ni^{2+}$-resin was equilibrated with sonication buffer. 4 ml of $Ni^{2+}$ resin was collected by centrifugation in a lab top centrifuge (Denley BR401) for 1–2 min at 500–600 rpm. The supernatant was decanted and washed 3×with 4 ml water and 3×with 4 ml sonication buffer. The equilibrated resin in 4 ml sonication buffer was added to the lysate and gently shaken for 1 h on ice. The Ni2+ resin with the bound peptide was collected and extensively washed with approximately a total of 100 ml wash buffer (50 mM $NaH_2PO_4$, 300 mM NaCl, 10% glycerol, pH 8), until $A_{280}$ was less then 0.01. The resin was poured into a column (1 cm diameter, 5 ml polypropylene disposable colunn, Qiagen) and the peptide eluded with a gradient elution buffer: wash buffer with a pH 6 to pH 4.25. 1 ml fractions were collected and tested on SDS-PAGE (polyacryl amide gel electrophoresis).

Both, the purchased (SP1) and the purified (SP2) peptides were injected, each into two rabbits at the UKC animal facilities (University of Kent, Canterbury). Blood sera were taken after four weeks and the rabbits were injected a second time, After a second bleed two to three weeks later, the rabbits were injected a third time and killed while collecting blood from the heart two weeks later. SDS—PAGE and Western Blotting SDS-PAGE was used to analyse proteins. The gel was made with the Mini-protean II electrophoresis cell (BioRad, Hertfordshire, UK). Instruction were provided with the system. The gel consisting of two parts, the separating and stacking gel, was prepared between two glass plates split by 1 mm thick spacers. The separating gel (12% acryl amide, 0.375 M Tris.Cl (pH 8.8), 0.1% SDS, 0.1% APS (ammonium persulphate) and 0.04% TEMED) was poured and when set, the stacking gel (5% acryl amide, 0.125 M Tris.Cl (pH 6.8), 0.1% SDS, 0.1% APS (ammonium persulphate) and 0.1% TEMED) was poured on top with a comb to make the slots. The samples were dissolved in 50 μl SDS gel loading dye (50 mM Tris.Cl (pH 6.8), 2% -mercaptoethanol, 1% SDS, 0.05% bromophenol blue, 5% glycerol) boiled for 5 min and loaded. Electrophoresis was performed in running buffer (25 mM Tris.Cl, 250 mM glycine and 0.1% SDS) at a constant voltage of 100 V for approximately 45 min. When the gel was not used for western hybridization, the proteins were fixed stained with coomassie blue staining solution (0.1% coomassie blue R-250 (BioRad) in 40% methanol and 10% acetic acid) for 30 min. The protein bands became visible after destaining with 40% methanol and 10% acetic acid. The gel was dried between two cellophane sheets which were first equilibrated in 10% glycerol together with the gel and tightened into a frame.

To blot the proteins from the gel onto a nitrocellulose membrane for western hybridization, after electrophoresis, the gel was soaked in the transfer buffer (25 mM Tris, 192 mM glycine and 20% methanol) for 15 min together with the membrane, and two sheets of 3 MM filter paper, cut to the size of the gel. The blotting was done using the Mini trans-blot electrophoretic transfer cell (BioRad). The gel was squeezed into a cassette holder with the presoaked membrane next to it, and a sheet of 3 MM filter on each side finished with a presoaked fiber pad on the outside. The proteins were transferred by electrophoresis from the gel onto the membrane with a voltage of 100 V for 1 h. The protein blot was tested by staining the membrane with Ponceau red (BioRad) which stained the proteins. The blot was washed with tap water.

Western Hybridization

Prior to hybridization with an antibody, the membrane was blocked with 1×TBS (0.15 M NaCl, 3 mM KCl, 25 mM Tris pH 7.4) and 5% Marvel (milk powder) for 1 h. Antibody hybridization occurred in the same buffer (1×TBS, 5% Marvel) plus 0.1% Tween and 0.1% azide overnight with a rabbit generated antibody with an estimated concentration of 1 ng/$\mu$l. The antibody solution was then poured off and stored in the fridge until needed again. The membrane was washed three times with 1×TBS and 0.1% Tween solution. The second antibody (anti-rabbit goat antibody conjugated to alkaline phosphatase (Sigma) was applied to hybridize to the first one. This second hybridization occurred in 1×TBS, 5% Marvel, and 0.1% Tween for 2 h. The antibody solution was poured off and the membrane 3 times washed with 1×TBS and 0.1% Tween. The second antibody was visualized by staining the membrane in a developing solution (10 mM Tris.Cl$^-$ pH 9, 25 mM MgCl$_2$, 2 mM NaCl, 200 $\mu$g/ml NBT (nitro blue tetrazolium) and 200 $\mu$g/ml BCIP (5-bromo-4-chloro-3-indolyl). Developing was performed until bands appeared, then the membrane was thoroughly washed with water.

EXAMPLE 25

Yeast Transformation

Yeast transformation was performed using known techniques. 0.5 ml medium was grown overnight at 28 C and the cells spun down for 10 s in an eppendorf. The supernatant was decanted and 1 $\mu$g of transforming DNA added to the pellet. The mixture was vortexed, 0.5 ml PEGALi-acetate/TE (40% PEG 4000, 0.1 M Li-acetate, 10 mM Tris.Cl$^-$ pH 7.5, 1 mM EDTA) was added and vortexed again. This mixture was incubated overnight at room temperature, and 50 $\mu$l was spread directly on a selective plate.

The media used for yeast was YPG (1% yeast extract, 2% peptone and 2% galactose), YPD (1% yeast extract, 2% peptone and 2% dextrose) and SG (synthetic minimal medium with galactose: 0.67% yeast nitrogen base, 2% galactose) with or without uracil (20 $\mu$g/ml), adenine (20 $\mu$g/ml), tryptophan (20 $\mu$g/ml), histidine (20 $\mu$g/ml) or leucine (30 $\mu$g/ml).

The vector used was pMAT1, which is a high copy yeast expressing plasmid containing the promoter, PGK1 (phosphoglycerate kinase), and contains LEU2 selection gene.

EXAMPLE 26

Membrane Protein Extraction from Yeast

The *Saccharomyces cerevisiae* yeast strains were inoculated in 2 ml rich YPG medium and incubated overnight at 28 C. A 200 $\mu$l aliquot of this culture was diluted into 100 ml YPG and incubated again at 28 C for at least 20 h. The cells were then spun down for 5 s at 1000 g (2500 rpm Denley labtop centrifuge) and the pellet dissolved in protein extraction buffer (10 mM EDTA, 100 mM Tris (pH 8), 400 $\mu$M PMSF) and put on ice. The same volume of glass beats (diameter of 0.5 mm) was added and the the mixture was vortexed for 3 times one minute with 1 minute intervals. After the cells were lysed the viscous solution was diluted with 10 ml of GTED20 (20% glycerol, 1 mM EDTA, 1 mM DTT, 10 mM Tris (pH 7.6)). The glass beats and cell debris were centrifuged down for 10 min at 1000 g (2500 rpm in Denley labtop centrifuge) at 4 C. The supernatant was carefully decanted and the membranes were spun down by centrifugation at 4 C for 30 min at 16000 rpm (30000 g in SS-34, Sorvall). After disposal of the supernatant, the membrane pellet was dissolved in 0.5 ml GTED20 ensuing an estimate protein concentration of 5 $\mu$g/$\mu$l. Protein extractions were stored at −20 C.

EXAMPLE 27

Botulinum C Reduces the ABA Signal in Guard Cells

To test the involvement of the syntaxin related proteins with the ABA signal response pathway in plants, the botulinum toxin type C (BotN/C) was used to knock out these proteins. The BotN/C cleavage site is very much conserved among the syntaxin 1 proteins, it exist of a sequence of 5 amino acids close to the hydrophobic C-terminus (FIG. 27). BotN/C recognizes the syntaxin proteins by two other domains, X1 and X2, located more upstream in the amino acid sequence. The X1 and X2 motifs consist of 9 amino acids forming a -helix confirmations generating a face with three negative charges contiguous to a face formed by hydrophobic residues (FIG. 27). The botulinum C is likely to cut into the SYR protein because of the preservation of the X1, X2 and partial preservation of the cleavage site together with the overall conserved tertiary structure (FIG. 27). BotN/D which digests in the VAMP and not in syntaxin 1A type molecules was used as control.

Guard cells close upon addition of ABA and amongst other processes, closure is mediated by increase in anion efflux and influx inhibition of potassium ions. These two characteristics were investigated for their modified reaction in the presence of ABA with or without BotN/C and BotN/D. Membrane voltage clamp was used to analyse the effect of both BotN/C and BotN/D. This experiment was performed on the guard cells of *N. benthamiana* and the attenuation of the ABA effect on the inward-rectifying K$^+$ was also checked in *Vicia faba*.

The Anion Current in *N. benthamiana* is not Enhanced by ABA When BotN/C is Implemented The guard cells of *N. benthamiana* were impaled to analyse the ABA response. To measure the anion currents, the K$^+$ currents were eliminated chemically with 15 mM TEA-Cl and 15 mM CsCl in the Ca-MES buffer. FIG. 28 shows current traces recorded while voltage clamping the guard cell membrane at voltages ranging from −230 mV to +30 mV for 7 s. The test pulses were preceded by a conditioning pulse of 5 s at +30 mV (not shown on the figure). The untreated (control) cell showed a large increase in the instantaneous anion current in ABA. The steady state of these currents was also changed, however more difficult to assess in this figure (FIG. 28). The effect of ABA was absent when BotN/C was injected into the cell, no changes in the anion current traces were recorded during at least 6 min of ABA treatment (FIG. 28). The increase of the instantaneous current by ABA was however detected when the cell was injected with BotN/D (FIG. 28).

The IV curves displayed in FIG. 29, compare the effect of ABA on either the instantaneous points (left) or the steady state points (right) of the anion current when the cells were treated with the botulinun toxin or not. The instantaneous IV curves were derived from the points at the beginning of the test pulses in FIG. 28. The effect of ABA on the instantaneous IV curve of a control cell changed towards a four-fold increase in current at −170 mV (FIG. 29A left). The current points chosen to create the IV curve of the steady state anion current, were picked at the end of the 7 s long test pulses from FIG. 28. The control cell showed a current increasing effect in ABA (FIG. 29A right). The slope conductance of the current measured at voltages around and above 0 mV had increased. At voltages below −50 mV currents were rather variable among the different cells. This ABA effect of the steady state current corroborates with the ABA induced instantaneous. In contrast to the non treated cell, the BotN/C treated cells did not allow any ABA effect on the instantaneous or the steady state anion currents (FIG. 29B). The BotN/D treated cell did show an ABA effect on the instantaneous anion current, a fourfold increase in current at −170 mV, comparable to the control cells (FIG. 29C left). The effect of ABA on BotN/D treated cells was also visible in the steady state phase of the anion current. Increase of the slope conductance was recorded at voltages around and above 0 mV (FIG. 29 right).

Statistical analysis shows that the reduction in ABA effect on the guard cells by injection of BotN/C, but not by BotN/D is general. The values of the instantaneous current at −170 mV were chosen for analysis. The maximum values after the ABA induced increase in current were normalized for the current values measured with the voltage clamp cycle before adding ABA. This maximum increase of the mean of the cells measured is displayed in FIG. 30. When the cells were not treated with the botulinum toxin, the ABA induced current increase was 3.5 fold (n=3). The BotN/C abolishes the increase of the instantaneous anion current, resulting in no (1-fold) increase (n=6). When the guard cells were injected with BotN/D, the increase was comparable (3-fold) with the control cells (n=2).

The ABA Mediated Inhibition of $I_{K.in}$ is Abolished by BotN/C in *N. benthamiana*

Guard cells of *N. benthamiana* were impaled with a double-barrelled electrode to voltage clamp the membrane in standard buffer (5 mM $Ca^{2+}$ MES and 10 mM KCl). To measure the inward-rectifying potassium currents, the voltage clamp protocol consisted of a 1 s pre-pulse of -100 mV, and eight 4 s test pulses ranging between −230 mV and +30 mV. FIG. 31 displays the current traces for the four lowest test voltages of this protocol. The inward-rectifying $K^+$ current, recorded at voltages more negative then −120 mV was inhibited by ABA in the non-treated control cells. When BotN/C was injected in the cell however, no difference in the inward-rectifier was noticed in reaction to ABA for at least 6 min. When BotN/D was applied however, the inward rectifier responded normally to ABA, resulting in inhibition of the current.

The steady state currents of the inward-rectifier were analysed and displayed in FIG. 32. The steady state current was selected at the end of the test pulses and was adjusted for the leak by subtracting the instantaneous current recorded at the immediate beginning of the step pulses. In a normal control cell, the inward time- and voltage-dependent $K^+$ current was inhibited by about 40% at −230 mV in response to ABA (FIG. 32A). The BotN/C treated cell however, failed to respond to the addition of ABA, the IV curve of the 11i, was virtually identical in the absence and presence of ABA (FIG. 32B). The IV curves of the cells treated with BotN/D showed a similar inhibition pattern as the IV curves for the control cells. When ABA was applied, an inhibition of $I_{K.in}$ was recorded of approximately 30% at −230 mV (FIG. 32C).

Statistical analysis of the maximum inhibition of $I_{K.in}$ is displayed in FIG. 33. The figure presents the mean ±SE of the ABA induced values of inward-rectifying $K^+$ current at −200 mV normalized for the $I_{K.in}$ before ABA was added. The mean $I_{K.in}$ inhibition by ABA in non treated cells values 46% of the original current (n=5). The inhibition is not significant (95%) for BotN/C treated cells (n=7). The current inhibition is identical within the standard error (45%) for the BotN/D treated cells (n=3) as for the control cells.

The ABA Mediated Inhibition of $I_{K.in}$ is Abolished by BotN/C in *V. faba*.

Measurements of BotN/C action on the ABA-sensitivity of 1 sin were repeated on *V. faba*. The membrane of the guard cells was voltage clamped with the same protocol as above to measure the inward-rectifying $K^+$ currents: prepulse of −100 mV for 1 s and eight 4 s test pulses ranging between −230 mV and +30 mV. The steady state current values at −200 mV were adjusted for the leak current by subtracting the instantaneous current of the test pulses. Currents in ABA were normalized with the steady state current of the same voltage before adding ABA. The normalized values were plotted versus time after adding ABA in FIG. 34 together with data from one control cell (see also Blatt, 1990 and Thiel, 1992). The control cell showed an approximate inhibition of 80% after 300 s. The mean of 3 BotN/C treated cells showed no significant change after addition of ABA. These results suggest that BotN/C acts universally in all plants.

EXAMPLE 28

Antibodies

In order to test whether the BotN/C toxin effect on guard cell membranes is caused by BotN/C cleaving the SYR protein, antibodies had to be generated to detect the SYR on a Western Blot. Antibodies were originally generated by two peptides (as described above).

Western Blot with the Synthetic Peptide SP1

The first peptide, SP1 consisted of a 13 amino acid long antigenic stretch of the SYR amino acid sequence (SEQ ID NO:2). Because of the small size of the peptide, it was conjugated to a keyhole limpet haemocyanin (KLH). KLH is routinely used as peptide-carrier protein and is hardly antigenic. The peptide conjugate was ordered from Pacemaker (Exeter, UK). Peptide: KLH-CGPGSSSDRTRTS (SEQ ID NO:44)

The peptide SP 1 was chosen from amino acid 115 to 127 of the SYR protein; (SEQ ID NO:2). This region was predicted highly antigenic and hydrophilic and had a high surface probability, as predicted by the PROTEAN program from Lasergene (DNA*). A conjugate of this SP1 with the KHL protein (SEQ ID NO: 44) was injected into 2 rabbits (Kent University, Canterbury (UKC)). The blood sera, sampled two to three weeks after a first, second and third SP1-KHL injection from either rabbit was tested for its recognition of the peptide SP1-KHL and of the SYR protein expressed in yeast (see below). No reaction was detected neither with SP1-KHL and SYR. Therefore, antibodies were generated against a second peptide.

Purification of the SP2

The DNA sequence coding for the entire hydrophilic part of the SYR protein was amplified by PCR. Hereby, two endonuclease recognition sites, BamHI and EcoRI were created at the end of the fragment so that it could be cloned into the expression vector pQE-30 (Quiagen) behind a strong IPTG inducible promoter (T5) resulting in pQES which was transformed into the E. coli strain M15[pREP4] (FIG. 26). The SYR peptide SP2 expressed by IPTG when grown in a liquid LB culture contained 6 histidine residues in front of the peptide, which allowed the peptide to bind to the $Ni^{2+}$ resin used to purify the peptide (Quiagen) by washing all other proteins away. The purified SP2 was eluded from the resin. Samples from all the different fractions during expression and purification were loaded onto an SDS PAGE and stained with coomassie blue stain (FIG. 35A). The sample containing SP2 still contained some contaminant E. coli proteins (faint blue bands in FIG. 35A) against which antibodies might be generated, but as the antibody mixture was to be used for yeast such antibodies would be unlikely to interfere. The SP2 sample was injected into the two rabbits at UKC.

Western Blot of the SP2

Two concentrations (5 ng and 50 ng) of the peptide SP2 were repeatedly denatured on a SDS PAGE and blotted on a nitrocellulose filters. The filters were then hybridized with the pre-immune serun, the first bleed, the second bleed and final bleed of the two rabbits. The pre-immune serum never showed any cross-reaction with the peptide SP2 (FIG. 35B). All the bleeds after the first injection of SP2 into both rabbits did cross-react with the peptide. FIG. 10B shows the bands visible when SP2 was hybridized with the second bleed of one of the rabbits. The intensity of the band is correlated with the concentration of the peptide SP2, at 50 ng hybridization is higher then at 5 ng, indicating specificity of the antibody.

EXAMPLE 29

BotN/C does not Digest SYR In Vitro

To test whether the BotN/C cleaves the SYR protein, a biochemical reaction was set up. A WT *Saccharomyces cerevisiae* yeast strain (W303-1A) overexpressing SYR, was used to prepare membrane protein extracts (Rothstein, 1983). Before the actual cleavage reaction, the Botulinum toxins were reduced in 10 mM DTT for 30 min at 37 C, this step is necessary to uncouple the two chains. The large chain, which is responsible to penetrate the cell is of no importance in this in vitro experiment. It is the release of the now active small chain which renders the toxin usable for syntaxin cleavage. If the BotN/C toxin digest the SYR protein in vitro, a shift of the SYR band from 34 kD to 30 kD should be seen on western blot. The reaction conditions were prepared in analogy with previous reported in vitro BotN/C experiments. The conditions were 15mM NaCl, 5 mM $MgCl_2$, 5M $ZnSO_4$, 1 mM DTT, 1 mM EDTA and 10 mM Tris pH 7.6 and 100 nM of the toxin BotN/C and BotN/D. The reaction was incubated for 4 h at 37 C. Around 20 μg protein was separated on a SDS PAGE, blotted onto a filter and hybridized with the anti-SYR antibody. FIG. 36B illustrates this western blot. Instead of the expected one protein SYR band, 4 bands were detected when SYR was expressed in the yeast strain W303-1A. All 4 bands however were related with SYR because none of them was present in protein membrane extract of the same strain without the SYR expressing plasmid or none were recognized by the pre-immune serum, as illustrated in panel A of this figure (FIG. 36A). The smallest of the 4 bands corroborates with the predicted size of the SYR protein (34 kD). The other, larger bands probably carry some modifications. It is shown in FIG. 36B that the BotN/C, under the conditions used, was not able to cleave SYR because no shift in either of the 4 bands was detected. BotN/D, as expected, did also not digest the SYR protein.

EXAMPLE 30

SYR is also Present in the N. Benthamiana

Because the guard cell voltage clamp experiments with the botulinum toxins were performed with N. *benthamiana* plants, the presence of the N. *tabacum* SYR gene in these plants was checked. Southern hybridisation was performed to identify the presence of identical or highly homologous genes. DNA was prepared from N. *tabacum* and N. *benthaniana*. 20 μg DNA was digested overnight with EcoRI or HindIII, the DNA fragments were separated on an agarose gel and blotted onto a membrane. The template for the probe comprised the full SYR cDNA insert, isolated from the psyr with EcoRI and NotI and purified by gel electrophoresis. The SYR cDNA was labelled with radioactivity and hybridised on the DNA filter at 65 C, overnight in hybridisation buffer. The filter was washed twice with 2xSSC and 0.1% SDS at 65 C. An X-ray film was exposed to the membrane for 96 h. Developing the film revealed some bands corresponding with SYR homologous sequences (FIG. 37). In the diploid species N. *benthamiana*, two major bands of about 12 kb and 4.7 kb and one minor band (10 kb) were detected in the lane with the EcoRI digested DNA. HindIII digestion of the DNA did only reveal one strong band (10 kb), and one faint band (approximately 20 kb). The pattern indicated the presence of an identical SYR gene in N. *benthamiana* and possibly also another less homologous gene. The pattern in N. *tabacum* is more difficult to interpret because N. *tabacum* is tetraploid. Two major bands of 8 kb and 6 kb are detected in the EcoRI digested lane, from which one seemed to be a duplicate. Additionally there was a faint band detected around 3 kb. The HindIII pattern is more complex, 4 stronger bands could be detected at 12 kb, 1 kb, and two close to each other at 5 kb. In the same lane there were also 3 fainter bands to be seen.

The same southern hybridization was performed by lower stringency conditions: in the same hybridisation buffer but at 52 C overnight and followed by only one wash with 2xSSC and 0.1% SDS. The result was the same as for 65 C, no additional bands appeared.

EXAMPLE 31

Expression Analysis

To analyse the expression pattern of SYR, Northern analysis was carried out. RNA was prepared from N. *tabacum* leaves or stems under different conditions. The probe used in these Northern experiments, was always the same and derived from the SYR cDNA insert. Hybridisation conditions were standard: 65 C overnight in a hybridisation buffer (6×SSC, 5×Denhardt's, and 0.1% SDS). Washing conditions consisted of 1 or 2 filter washes with 2×SSC, 0.1% SDS buffer.

SYR Expressed in Leaves and Stems

A first experiment implied the isolation of mRNA for leaves and stems of N. tabacum when grown under 2 different conditions. mRNA was isolated from leaves and stems separately either grown in approximately 100% humidity or grown under greenhouse conditions (approximately 60% humidity). 2.5 µg mRNA was loaded on a formaldehyde containing agarose gel and blotted on a membrane. Hybridization results with the SYR probe of this membrane are shown in FIG. 12A. Different SYR expression patterns were identified for leaves versus stems. In 100% humidity conditions transcripts of the SYR gene was present in the stems but seemed lacking in the leaves. However, when the growth conditions of the plants were drier (greenhouse conditions), the SYR transcripts were present both in leaves and stems. In conclusion, the SYR transcript is not restricted to the leaves, and is present under either wet or dry conditions in the stems, but is absent in the leaves when the plants is growing in very humid environment.

Stress or ABA Induced SYR Expression mRNA was isolated from leaves of N. tabacum. The plants were grown under very highly humid conditions, in a covered tray. The 6 weeks old plants were treated with 20 µM ABA in tap water, by spraying the leaves and by watering the soil. Leaves were collected for mRNA preparation before (as a control), or after 1 h, 24 h or 48 h ABA treatment. Some plants were drought stressed by removing them from the humid conditions and subjecting them to ambient air conditions, without water supply. Leaves were collected for mRNA preparation after 72 h when the leaves started to wilt. The radiogram of the hybridisation with a SYR probe of a blot containing 2.5 µg mRNA per lane, are displayed in FIG. 12B. The transcript level of SYR increased when leaves were treated with ABA, or when the plant was subject to drought stress. The increase after the beginning of the ABA treatment was rapidly induced (1 h), the level enhanced until 24 h after the offset, and reduced slightly after 48 h. The transcript induction seemed slowly transient.

To verify these results, they were reproduced with other N. tabacum plants grown in highly humid conditions in a plastic chamber. The 6 week old plants were treated with ABA as above, and leaves were collected after 30 min, 1 h, 3 h, 6 h, 12 h, 24 h, 48 h. Total RNA was prepared from the leaves and 15 µg RNA was organised by electrophoresis on an agarose gel and blotted on a membrane. An X-ray film with the results from the hybridisation with a SYR probe are shown in FIG. 12C (left). A transient induction of the SYR transcript was demonstrated. In this experiment however, the timing was different then in the above mentioned experiment. The amount of transcript was highest 30 min after the beginning of the ABA treatment and was reduced after this approaching the original control level at 3 h and rising slowly again after 24 h. In addition, a 30 min auxin (IAA) treatment of N. tabacum plants was also tested for induction of SYR. Even though northern analysis showed again the induction of SYR after 30 min of ABA treatment of the plants, no increase in transcription level of SYR was detected after 30 min of IAA treatment (FIG. 12C right). Equal amounts of RNA were loaded on each gel, as shown by a photo of the ethidium bromide stained ribosomal RNA bands (FIG. 12D).

EXAMPLE 32

Yeast Complementation

The yeast strain Saccharomyces cerevisiae contains two syntaxin genes SSO1 and SSO2 which are closely related to each other and are functionally interchangeable. They were cloned as suppressors for a yeast mutation which was deficient in its secretory pathway. Disruption of both genes in the yeast is lethal. A strain H440 was created from which both genes. SSO1 and SSO2 were deleted from the wild type yeast strain W303-1A but the strain survived because it contained a plasmid with the SSO1 gene under the control of a galactose inducible promoter (GAL1). As a result, H440 can only grow on a medium containing galactose.

The SYR gene from N. tabacum was cloned into a yeast expression vector under the control of a strong promoter. This construct was transformed into the yeast H440 strain resulting in H440(SYR) and grown both on a glucose medium and on a galactose medium. The strain H440 as well as H440(SYR) grew well on the galactose containing medium as expected, because the SSO1 gene was expressed (FIG. 38A). When H440 was inoculated on a medium without galactose, no growth was observed as the SSO1 expression was eliminated. The SYR gene could not suppress this mutation. When the H440(SYR) strain was grown on the galactose deficient medium, the strain did not recover (FIG. 38B). As a control the wild type S. cerevisiae strain was also inoculated, and grew well on either medium.

SYR Expression in H440(SYR)

The presence of SYR protein in the newly constructed strain H440(SYR) was tested with the newly made anti-SYR antibodies. Protein extracts of membranes were prepared of the yeast strains H440 and H440(SYR). They were separated on a gel by electrophoresis and blotted onto a filter. The anti-SYR antibody recognized a protein in the extract of the SYR expressing strain but not in the H440 itself (FIG. 38C). Specificity was confirmed by the lack of hybridization of this protein to the pre-immune sample of the same rabbit. This shows that expression of SYR was accomplished, so failure of complementation of the SSO1 and SSO2 mutation was not due to deficient translation of SYR.

EXAMPLE 33

EST and Southern Arabidopsis

Because Arabidopsis thaliana is used as a model system in molecular biology and many of its genes are at least partially sequenced, a search was performed towards the A. thaliana gene 'identical' to the N. tabacum SYR gene. The BLASTN search was accomplished at the NCBI net site with the dbEST bank. EST's are expressed sequence tags, partial sequences of cDNA clones from Arabidopsis thaliana. Apart from the KNOLLE sequence, one novel sequence was picked out by this search. The EST, P16862 showed 70% identity at nucleotide level and 62.6% identity at amino acid level.

To check whether this or other sequences corresponded with SYR, a southern blot was performed using Arabidopsis thaliana DNA which was digested with the EcoRI restriction endonucleases and botted on a nylon membrane after electrophoresis on a agarose gel. The hydridization conditions were standard, 65 C overnight in hybridization solution followed by two washes at 65 C with 2×SSC and 1% SDS. FIG. 39B shows the autoradiogram of this experiment. The lane on the right shows the results when the SYR probe was hybridized, and the left lane when the EST, P16862 was used. In each case one single band was detected in either lane but of a different size. The SYR probe recognize a DNA band of 4.7 kb and the EST, P16862 probe recognizes a band of 3.8 kb. This indicates that there exists a gene in *Arabidopsis thaliana* with high similarity to SYR but that this gene is not represented by the EST.

EXAMPLE 34

Expression of syr

The gene syr was cloned into the pG3.3 vector. The pG3.3 (14.92 kb) vector contains the reporter gene uidA encoding for β-glucuronidase (GUS) behind a 35S promoter between the borders of the T-DNA. The T-DNA also contains the kanamicin (Km) resistance gene. The vector carried a second 35S promoter, followed by some unique restriction sites, to clone foreign genes under the control of this 35S promoter. The 35S promoter is originated from the Cauliflower Mosaic virus and is constitutively expressed in *Nicotiana tabacum*.

The syr gene was inserted in the pG3.3 vector behind the 35S promoter in two different directions. Two new constructs were obtained: pGSS (with the syr gene inserted in the sense direction behind the 35S promoter) and pGSA with the syr gene inserted in the antisense direction behind the 35S promoter.

The three constructs pG3.3, pGSS and pGSA were transformed to the *Agrobacterium tumefaciens* strain LBA4404 which is used for transformation of *N. tabacum* and contains the rifampicin (Rif) resistance gene. Transferring the vectors from *E. coli* to *A. tumefaciens* was achieved via triparental mating using the pRK2013 as a helper plasmid.

In preparation for the transient transformation, the Agrobacterium strains containing either the pG3.3, pGSS or pGSA constructs were grown for 2 nights at 28 C in 20 ml LB containing Km (20 µg/ml) and Rif (25 µg/l). The bacterial culture is then pelleted by centrifugation and resuspended in 200 ml induction medium plus Km (20 µg/ml). Induction medium contains 10.5 g/l $K_2HPO_4$, 4.5 g/l $KH_2PO_4$, 1 g/l $(NH_4)_2SO_4$, 0.5 g/l $NaCitrate.2H_2O$, 1 mM $MgSO_4.H_2O$, 0.2% glucose, 0.5% glycerol, 50 µM 3',5'-Dimethoxy-4'-hydroxyacetophenone (Aldrich) and 10 mM N-morpholino-ethanesulfonic acid (MES), pH 5.6. After overnight incubation at 28 C bacteria were pelleted by centrifugation and washed with Murashige and Skoog's medium (MS, Sigma) with 10 mM MES pH 5.6, and resuspended in 100 ml MS-MES medium with 150 µM 3',5'-Dimethoxy-4'-hydroxyacetophenone (Aldrich) and 0.05% Silwet (Vac-in-Stuff, Lehle seeds, Round Rock, Tex., USA). The bacterial suspensions were then ready for transformation.

*Nicotiana tabacum* plants of 4–6 weeks old were used for the transient expression. The last 3 days before the transformation, plants were transferred to 100% humidity. For the infiltration, the whole plant with the soil was transferred to a vacuum chamber, while the soil was sealed off with plastic foil. A young but fully expanded leaf was gently inserted in a beaker which is filled with the bacterial suspension of *A. tumefaciens*. Vacuum was applied using a vacuum pump until the atmosphere in the chamber was less than 0.1 mbar for several minutes until the bacterial solution was thoroughly boiling, then the vacuum was released promptly. The infiltration of the solution was visible in the young leaf, starting at the tip spreading over about ⅔ of the entire leaf. The plants were incubated at 100% humidity for 72 h at 23 C and 12 h light/12 h dark cycle.

Gene expression was controlled by testing the infiltrated plant leaf for GUS activity, which can be easily tested by hystochemical staining. The tissue was incubated at 37 C overnight in a GUS staining solution: 50 mM $NaPO_4$ buffer pH 7, 0.5 mM Sodium ferro/ferri cyanide, 0.05% Triton X-100 and 0.5 mg/ml 5-bromo-4-chloro-3-indoxyl--D-glucuronic acid, 0.1 mg/ml chloramphenicol. After staining the tissue was washed with several washes of EtOH.

Originally three leaves of three different plants were infiltrated with pGSA, the construct containing the antisense cDNA of syr (FIG. 40; SEQ ID NO:3) under the control of the 35S promoter. After three days of incubation at 23 C and 100% humidity, the plants were tested for different wilty phenotype in the leaves. The plants with soil were transferred from their 100% humidity environment to a dry place 30 cm under 180 W lamps. The leaves transformed with the: pGSA seem to start wilting sooner than the control non-infiltrated leaves. This means that after approximately 5 min, the tip and edges (where the pGSA was infiltrated) of the transformed leaf were starting to hang down and being wilty, whereas the other leaves only started to dry out at approximately 10 min after the transfer. This was recorded for two of the three plants. The two transformed leaves were tested for GUS activity. Blue stains as result of the GUS activity were detected in approximately 10% of the cells in the infiltrated area, indicating gene expression via the 35S promoter was occurring in the plant cells. No GUS activity was detected in two control leaves tested.

The wilting phenotype was even better recorded when the third plant was transferred from 100% humidity to ambient air conditions with still well-watered soil. 16 hours (overnight) later, the infiltrated leaf showed a double appearance. The base of the leaf was standing up, as normal (wild type) but the Agrobacterium infiltrated part of the leaf towards the tip hung down and had a wilty appearance. All other leaves looked healthy. At this time the infiltrated leaf was used to measure the stomatal apertures. Stomatal closure is regulated by the loss in turgor pressure, caused by ABA in the guard cells surrounding the stoma. Stoma should close when in dry conditions to prevent transpirational loss of water. If a signal transduction component was missing, the guard cells could not respond to ABA anymore and the stoma remain therefore open, even in dry conditions. Epidermal strips were taken from the two different areas of the leaf, the wilty and the healthy area. The mean of the aperture of the stoma was measured of 20 different stoma. It appeared that the aperture of the witty area was more open (3.2 µM±0.32) than the stomatal aperture of the healthy area (1.6 µM±0.17).

EXAMPLE 35

Transformation of Plants to Overexpress the SYR Protein

The SYR gene was cloned behind a 35S promoter (see transient transformation protocol) into the transformation vector pSLJ75516, resulting in pTSS. pTSS which is Tetracyclin (Tc) resistant contains the SYR gene in a sense orientation behind the strong constitutive 35S promoter which is followed by the terminator, nos. The tDNA of pTSS also contains the BASTA resistance gene generating resistance against phosphothricin (PPT) which allows selection of the tDNA transformed tobacco plants. The plasmid pTSS was transformed into the Agrobacterium tumefaciens strain LBA4404 which is rifampicin (rif) resistant and which is suited for transformation of *Nicotiana tabacum*. Transformation occurred by triparental transformation using the pRK2013 as a helper plasmid. Seeds of *Nicotiana tabacum* were sterilized, by treatment for 1 min in 70% ethanol, followed by a 1 min wash in sterile water and 3 min incubation in 50% household bleach containing 0.1% (v/v) tween again followed by 5 washes of 5 min in sterile water. The seeds were germinated on a germination media:1×MS (Murashige and Skoog) salts, 20 g/l sucrose and 0.05% (w/v) MES buffer pH 5.7 (adjusted with 1 M KOH), bring the media to boil and then add 0.3% (w/v) phytogel. The plates containing the seeds were incubated at 25° C. with 16 h light and 8 h dark cycle. The Agrobacterium strain containing pTTS was grown overnight with selection (Tc (10 mg/l and rif (25 mg/l)). The Agrobacterium cells were collected by centrifugation (3000 rpm in lab top centrifuge DenleyBR401) for 20 min and resuspended in 0.85% (w/v) NaCl. After 3–4 weeks a mature but fully green and healthy leave of the tobacco plants was selected and a square of approximately 1 cm$^2$ was cut out for transformation. The tissue was wounded and placed upside down onto a plant regeneration medium containing plate (1×MS salts, 20 g/l sucrose, 0.05% (w/v) MES buffer pH 5.7 (adjusted with 1 M KOH), 0.3% photogel, and after autoclaving the medium, the phytohormones were added from a 1000 times stock: 0.2 mg/l Naphtalene acetic acid (NAA) and 2 mg/l benzyl aminopurine (BA)). The leaf pieces were dipped into the Agrobacterium solution (while avoiding excessive soaking), and then blotted on filter paper and transferred back onto the regeneration media with the selection: 2 mg/l phosphothricin (PPT, to select for transformants containing the TDNA of pTTS) and 100 mg/l augmentin (to kill the Agrobacterium). The tissues were at this stage incubated at 25° C. with a 16 h light and 8 h dark cycle until the shoots were produced. The shoots were then transferred onto root inducing media (1×MS salts, 0.05% (w/v), 10 g/l sucrose, MES pH 5.7 (adjusted with 1 M KOH) and 1 mg/l PPT, to avoid escapes from the shoot regeneration stage to get roots) and again incubated at 25° C. and 16 h light and 8 h dark cycle. When roots were visible (about 1 cm), the little plants were transferred to soil as soon as possible and grown under high humidity in greenhouse conditions.

Media:

Germination media: 1×MS (Murashige and Skoog) salts 20 g/l sucrose 0.05% (w/v) MES buffer pH 5.7 (adjusted with 1 M KOH) bring the media to boil and then add 0.3% (w/v) phytogel Regeneration medium:

1×MS salts 20 g/l sucrose 0.05% (w/v) MES buffer pH 5.7 (adjusted with 1 M KOH)

0.3% photogel after autoclaving the medium, the phytohormones were added from a 1000 times stock: 0.2 mg/l Naphtalene acetic acid (NAA) 2 mg/i benzyl aminopurine (BA)

Root inducing:

1×MS salt 10 g/l sucrose 0.05% (w/v) MES pH 5.7 (adjusted with 1 M KOH) 1 mg/l PPT Transformed Plants The level of Nt-SYR in the overexpressing sense plants were enhanced as shown on Western blot analysis. Overexpression increases sensitivity to ABA (allowing protection against short-term stress such as snap frost or periodic drought stress). Preferably the is targetted.

The antisense plants showed a pleotropic phenotype, observed in about 10% of the transformants. Because of the high success in transformation with the sense constructs (over two dozen independent transformants isolated) compared with the antisense transformants (>20 plants, but all derived from only 2 independent transformation events), we suspect that most antisense transformations are lethals and only the least severe (and/or unstable) forms survive.

The identified phenotype of the antisense plants is characterised at a macroscopic level by gross distortion of leaf morphology, including thickening of the tissues overall and severe reduction in expansion of the lamina, dwarfing and sterility of the plant. At the extreme, the leaves look like dark green sticks with a central vein and no lateral expansion of the leaf. At the microscopic level the mesophyll show poor differentiation with abnormal expansion in some areas and hypertrophy in others. Within the epidermis the guard cells and epidermal cells show aborted development at various stages. There are frequent occurances of guard cells appearing singly, rather than in pairs (as is normal around the stomatal pore). Many guard cells show abnormal expansion and, of the quasi-normal guard cells, these are roughly 50% larger than in the wild-type. Electrical analysis of the ion channels in these cells has shown varying degrees of loss in sensitivity to ABA (approx. 40% normal response to complete loss of sensitivity). Because of the alterations in morphological pattern, however, we cannot be sure at this time whether these latter effects are a consequence of abberant developmental programming rather than a physiological change. From the BotN/C and Sp2 experiments we suspect a direct physiological action, and we hope to confirm this through work with the inducible promoter transformants now in preparation (below). The inducible approach should also give us a handle on the effects of overexpression.

Localisation via Immunogold Labelling

The localisation of Nt-SYR is also analysed at the electron-microscopy level using the polyclonal antiserum against Nt-SYR (generated in rabbit against the Sp2 peptide), and a purified antibody (purification was obtained with a Sp2-affinity column). In the control experiments a pre-immune serum (serum taken before Sp2 injection in the rabbit) of the same rabbit was used. Another control experiment comprised the pre-absorbence of the antiserum or antibody by the antigen (Sp2) prior to labelling. That way, the specific antibody-antigen interaction is titrated away from the tissue section.

The leaves of the wild type and overexpressing tobacco plants were fixed and embedded using in either LR White or Epoxy resin. With both resins, a similar picture was seen however less background and more detail analysis could be detected with epoxy resin. Most After ultra-thin section were cut with a microtome on golden grids, the grids were used for preybridisation (2% BSA) for 30 min, hybridisation with $\frac{1}{200}$ of serum or $\frac{1}{5}$ of purified antibody overnight at 4 C. A second hybridisation was performed with a commercial available antibody conjugated to a gold particle (10 nm) against anti-rabbit serum. The electron dense dots from the gold particles can be detected using an electron microscope. The final results showed association of the antibody with the plasma membrane because the dots disappeared upon pre-absorption of the antiserum or antibody with the antigen. In the samples hybridised with preinmmune serun, much less dots were counted in the plasma membrane region even though other areas such as the cytosol and the chloroplasts still contained some labelling. The sections derived from the sense plants showed a high increase over the wild type in the amount of label everywhere: in plasma membrane, in cytosol and chloroplasts. The plasma membrane has an estimate of double the amount of the dots in the plasma membrane in the wild type sections.

Inducible Transformants

Constructs are prepared using three systems. Two inducible promoters are based on the mammalian dexamethasone-sensitive promoter which is activated on exposure to dexamethasone. One of these we obtained from N.-H. Chua (Plant J. (1997) 11:605). The second includes multiple tetracycline repressor elements behind the dexamethasone promoter, thus enabling the promoter to be turned of by tetracycline after being turned on. This construct we obtained from Christiane Gatz (Goettingen; Plant J. (1992) 2:397). A further promoter was obtained from Andy Greenland (Zeneca) which is activated by ethanol (Nature Biotechnology (1998) 16:177). The constructs are all designed to express one of the following: (1) the truncated protein Sp2, (2) the antisense sequence, and (3) the complete Nt-Syr protein. (1) and (2) give a controlled elimination of Nt-Syr function. Obviously, (3) results in controlled over expression.

What is claimed is:

1. An isolated protein capable of affecting an absicisic acid (ABA) response and comprising:
   (i) a hydrophobic C-terminus;
   (ii) at least one coiled coil region;
   (iii) an EF-hand consensus sequence;
   (iv) a nucleotide binding site; and optionally
   (v) a hydrophilic N-terminus;
   wherein said protein participates in ABA signalling as measured by its ability to participate in ABA-mediated control of ion channels.

2. An isolated protein according to claim 1 which is capable of being cleaved by the toxin botulinum C.

3. An isolated protein according to claim 1 wherein the hydrophobic C-terminus comprises the sequence from position 282 to position 296 of the amino acid sequence shown in SEQ ID NO:2.

4. An isolated protein according to claim 1 wherein the hydrophobic C-terminus comprises the sequence from position 280 to position 294 of the amino acid sequence shown in SEQ ID NO:2.

5. An isolated protein according to claim 1 wherein there are three coiled coil regions.

6. An isolated protein according to claim 1 wherein said at least one coiled coil region comprises the sequence from position 210 to position 247 of the amino acid sequence shown in SEQ ID NO:2.

7. An isolated protein according to claim 1 wherein said at least one coiled coil regions comprises the sequence from position 216 to position 240 of the amino acid sequence shown in SEQ ID NO:2.

8. An isolated protein according to claim 1 wherein said at least one coiled coil region corresponds to an epimorphin pattern.

9. An isolated protein according to claim 6 wherein said at least one coiled coil region corresponds to an epimorphin pattern.

10. An isolated protein according to claim 1 wherein said hydrophilic N-terminus comprises the sequence from position 1 to position 280 of the amino acid sequence shown in SEQ ID NO:2.

11. An isolated protein according to claim 1 wherein the hydrophilic N-terminus comprises the sequence from position 1 to position 279 of the amino acid sequence shown in SEQ ID NO:2.

12. An isolated protein according to claim 1 wherein said nucleotide binding site comprises the sequence of positions 114 to 119 of the amino acid sequence shown in SEQ ID NO:2.

13. An isolated protein according to claim 1 wherein the nucleotide binding site comprises the sequence of positions 116, 118 and 120 of the amino acid sequence shown in SEQ ID NO:2.

14. An isolated protein according to claim 1 wherein said EF-hand consensus sequence comprises the sequence from position 16 to 28 of the amino acid sequence shown in SEQ ID NO:2.

15. An isolated protein according to claim 1 wherein said hydrophobic C-terminus comprises a membrane spanning region.

16. An isolated protein according to claim 1 that is derived from a plant.

17. An isolated protein according to claim 1, wherein said protein affects ABA-mediated control of guard cell $K^+$ and $Cl^-$ channels.

18. An isolated protein according to claim 1, wherein said protein affects ABA-mediated stoma closure regulation in a plant.

19. The isolated protein according to claim 1, wherein the protein, when overexpressed in a host cell, augments ABA signalling as measured by its ability to participate in ABA-mediated control of ion channels.

20. An isolated protein comprising the amino acid sequence shown in SEQ ID NO:2, or a biologically active fragment thereof, wherein said protein, or said biologically active fragment thereof participates in absicisic acid (ABA) signalling as measured by its ability to participate in ABA-mediated control of ion channels.

21. An isolated protein comprising amino acids 1–279 of SEQ ID NO:2, or a biologically active fragment thereof, wherein said protein or said biologically active fragment thereof inhibits an absicisic acid (ABA) response.

22. The isolated protein according to claim 21, wherein the protein or biologically active fragment thereof inhibits an ABA response as measured by the ability to inhibit ABA-mediated control of ion channels.

23. The isolated protein according to claim 21, wherein the protein comprises amino acids 1–279 of SEQ ID NO:2.

24. An isolated protein which affects an absicisic acid (ABA) response and comprises an amino acid sequence having at least 50% identity to the amino acid sequence shown in SEQ ID NO:2, wherein said protein participates in ABA signalling as measured by its ability to participate in ABA-mediated control of ion channels.

25. An isolated protein which affects an absicisic acid (ABA) response and comprises an amino acid sequence having at least 75% identity to the amino acid sequence shown in SEQ ID NO:2, wherein said protein participates in ABA signalling as measured by its ability to participate in ABA-mediated control of ion channels.

26. An isolated protein which affects an absicisic acid (ABA) response and comprises an amino acid sequence having at least 85% identity to the amino acid sequence shown in SEQ ID NO:2, wherein said protein participates in ABA signalling as measured by its ability to participate in ABA-mediated control of ion channels.

27. An isolated protein which affects an absicisic acid (ABA) response and comprises an amino acid sequence having at least 95% identity to the amino acid sequence shown in SEQ ID NO:2, wherein said protein participates in ABA signalling as measured by its ability to participate in ABA-mediated control of ion channels.

28. An isolated protein which comprises the amino acid sequence shown in SEQ ID NO:2, wherein said protein or fragment thereof participates in ABA signalling as measured by its ability to participate in ABA-mediated control of ion channels.

29. An isolated protein according to any one of claims 24–27, wherein said protein is capable of being cleaved by the toxin botulinum C.

30. A method of screening for protein-protein interaction comprising:

a) contacting a protein according to any one of claims 1–20 with an expressed candidate absicisic acid (ABA) signalling component; and b) detecting interaction between said protein and said ABA signalling component.

* * * * *

SEQUENCE LISTING

<160> NUMBER OF SEQ ID NOS: 44

<210> SEQ ID NO 1
<211> LENGTH: 1205
<212> TYPE: DNA
<213> ORGANISM: Nicotiana tabacum
<220> FEATURE:
<221> NAME/KEY: CDS
<222> LOCATION: (18)..(917)

<400> SEQUENCE: 1

```
ccaaatccca tctcaaa atg aat gat cta ttt tca gga tct ttc tct cgt         50
                   Met Asn Asp Leu Phe Ser Gly Ser Phe Ser Arg
                    1               5                  10 ttc aga gct gac gat caa tcg gac tct cac gcc ata gaa atg gga gac         98
Phe Arg Ala Asp Asp Gln Ser Asp Ser His Ala Ile Glu Met Gly Asp
             15                  20                  25 att act ggc gga gtc aat ctc gac aaa ttc ttc gaa gat gtt gaa gcc        146
Ile Thr Gly Gly Val Asn Leu Asp Lys Phe Phe Glu Asp Val Glu Ala
         30                  35                  40 att aaa gac gaa ctc aaa ggc ctc gag aaa atc tat tcc caa ctc caa        194
Ile Lys Asp Glu Leu Lys Gly Leu Glu Lys Ile Tyr Ser Gln Leu Gln
     45                  50                  55 tct tcc cat gaa aaa agc aag act ctt cac aac gct aaa gcc gtt aaa        242
Ser Ser His Glu Lys Ser Lys Thr Leu His Asn Ala Lys Ala Val Lys
 60                  65                  70                  75 gat cta aga tcc aac atg gat aat gac gtt tcc atg gca ttg aag aaa        290
Asp Leu Arg Ser Asn Met Asp Asn Asp Val Ser Met Ala Leu Lys Lys
                 80                  85                  90 gcc aaa ttc atc aaa gtt cgt ctc gaa gcc tta gac aga tca aat gca        338
Ala Lys Phe Ile Lys Val Arg Leu Glu Ala Leu Asp Arg Ser Asn Ala
             95                 100                 105 gcg aat cga agc ctc cct gga tgt gga ccc gga agt tca tct gac agg        386
Ala Asn Arg Ser Leu Pro Gly Cys Gly Pro Gly Ser Ser Ser Asp Arg
         110                 115                 120 acg aga act tca gtt gtg aac gga tta agg aag aaa ctt caa gag tca        434
Thr Arg Thr Ser Val Val Asn Gly Leu Arg Lys Lys Leu Gln Glu Ser
     125                 130                 135 atg aat cag ttc aac gag cta agg caa aag atg gca tct gaa tat agg        482
Met Asn Gln Phe Asn Glu Leu Arg Gln Lys Met Ala Ser Glu Tyr Arg
140                 145                 150                 155 gaa aca gtt caa cga cga tat tat acc gtc aca gga gaa aat cct gat        530
Glu Thr Val Gln Arg Arg Tyr Tyr Thr Val Thr Gly Glu Asn Pro Asp
                 160                 165                 170 gaa gca gtt ctt gat aca ctc ata tct aca ggt caa agt gag acg ttc        578
Glu Ala Val Leu Asp Thr Leu Ile Ser Thr Gly Gln Ser Glu Thr Phe
             175                 180                 185 ttg caa aag gca att caa gag caa ggg aga gga caa gtg atg gat aca        626
```

-continued

```
Leu Gln Lys Ala Ile Gln Glu Gln Gly Arg Gly Gln Val Met Asp Thr
            190                 195                 200 gtt atg gaa att caa gaa agg cat gaa gct gtg aag gaa ttg gag agg      674
Val Met Glu Ile Gln Glu Arg His Glu Ala Val Lys Glu Leu Glu Arg
        205                 210                 215 aat ttg aaa gaa ttg cat caa gta ttc ttg gac atg gct gtt ttg gtt      722
Asn Leu Lys Glu Leu His Gln Val Phe Leu Asp Met Ala Val Leu Val
220                 225                 230                 235 gaa agt caa gga gct caa ctt gat gat att gag agc caa gtg aat agg      770
Glu Ser Gln Gly Ala Gln Leu Asp Asp Ile Glu Ser Gln Val Asn Arg
                240                 245                 250 gct aat tcc ttc gtt aga ggg ggt gct cag caa ctg caa gtg gca agg      818
Ala Asn Ser Phe Val Arg Gly Gly Ala Gln Gln Leu Gln Val Ala Arg
            255                 260                 265 aag cac cag aag aac act aga aaa tgg act tgt ttt gct att att ctt      866
Lys His Gln Lys Asn Thr Arg Lys Trp Thr Cys Phe Ala Ile Ile Leu
        270                 275                 280 ctg ctt atc atc att ttg gtg gtg gtt ctt tct att cag cca tgg aaa      914
Leu Leu Ile Ile Ile Leu Val Val Val Leu Ser Ile Gln Pro Trp Lys
285                 290                 295 aaa tgagaatttg tctatggtca aggtcttct ggtggacccc ttcaatgttt            967
Lys
300 tgaatattct aaattttat attttattat tttagccatg cttattattt tgtgttattt      1027 tggattttt ttttgttttt aatgtgggga agagtaaact ggatgggggt ccatgtgcta     1087 tttagagaaa tacttgggag ttctcttttt gtaattattg ctgtatttag agtataattc    1147 tttttctata ttgttggcag gttaatttgt ttgtttgatt atattctcat ttagattt      1205

<210> SEQ ID NO 2
<211> LENGTH: 300
<212> TYPE: PRT
<213> ORGANISM: Nicotiana tabacum

<400> SEQUENCE: 2

Met Asn Asp Leu Phe Ser Gly Ser Phe Ser Arg Phe Arg Ala Asp Asp
1               5                   10                  15

Gln Ser Asp Ser His Ala Ile Glu Met Gly Asp Ile Thr Gly Gly Val
                20                  25                  30

Asn Leu Asp Lys Phe Phe Glu Asp Val Glu Ala Ile Lys Asp Glu Leu
            35                  40                  45

Lys Gly Leu Glu Lys Ile Tyr Ser Gln Leu Gln Ser Ser His Glu Lys
        50                  55                  60

Ser Lys Thr Leu His Asn Ala Lys Ala Val Lys Asp Leu Arg Ser Asn
65                  70                  75                  80

Met Asp Asn Asp Val Ser Met Ala Leu Lys Lys Ala Lys Phe Ile Lys
                85                  90                  95

Val Arg Leu Glu Ala Leu Asp Arg Ser Asn Ala Ala Asn Arg Ser Leu
                100                 105                 110

Pro Gly Cys Gly Pro Gly Ser Ser Ser Asp Arg Thr Arg Thr Ser Val
            115                 120                 125

Val Asn Gly Leu Arg Lys Lys Leu Gln Glu Ser Met Asn Gln Phe Asn
        130                 135                 140

Glu Leu Arg Gln Lys Met Ala Ser Glu Tyr Arg Glu Thr Val Gln Arg
145                 150                 155                 160

Arg Tyr Tyr Thr Val Thr Gly Glu Asn Pro Asp Glu Ala Val Leu Asp
                165                 170                 175
```

```
Thr Leu Ile Ser Thr Gly Gln Ser Glu Thr Phe Leu Gln Lys Ala Ile
            180                 185                 190

Gln Glu Gln Gly Arg Gly Gln Val Met Asp Thr Val Met Glu Ile Gln
        195                 200                 205

Glu Arg His Glu Ala Val Lys Glu Leu Glu Arg Asn Leu Lys Glu Leu
    210                 215                 220

His Gln Val Phe Leu Asp Met Ala Val Leu Val Glu Ser Gln Gly Ala
225                 230                 235                 240

Gln Leu Asp Asp Ile Glu Ser Gln Val Asn Arg Ala Asn Ser Phe Val
            245                 250                 255

Arg Gly Gly Ala Gln Gln Leu Gln Val Ala Arg Lys His Gln Lys Asn
        260                 265                 270

Thr Arg Lys Trp Thr Cys Phe Ala Ile Ile Leu Leu Leu Ile Ile Ile
    275                 280                 285

Leu Val Val Leu Ser Ile Gln Pro Trp Lys Lys
290                 295                 300

<210> SEQ ID NO 3
<211> LENGTH: 1334
<212> TYPE: DNA
<213> ORGANISM: Arabidopsis thaliana
<220> FEATURE:
<221> NAME/KEY: CDS
<222> LOCATION: (77)..(991)

<400> SEQUENCE: 3
gaattcctcg agctacgtca gggattcatt ccgatctgaa atctctctct agatttctct      60 attttcgaa tttaa atg aac gat ttg ttt tcc agc tca ttc tct cgc ttc      112
              Met Asn Asp Leu Phe Ser Ser Ser Phe Ser Arg Phe
                1               5                  10 cgc agc gga gaa cca tcc cct cgc cga gac gtt gcc ggc ggt ggc gac      160
Arg Ser Gly Glu Pro Ser Pro Arg Arg Asp Val Ala Gly Gly Gly Asp
         15                  20                  25 gga gtt cag atg gcg aat ccc gcg gga tca acc ggt ggt gtg aac ctc      208
Gly Val Gln Met Ala Asn Pro Ala Gly Ser Thr Gly Gly Val Asn Leu
     30                  35                  40 gac aag ttc ttc gaa gat gtt gaa tct gtg aaa gaa gag cta aag gag      256
Asp Lys Phe Phe Glu Asp Val Glu Ser Val Lys Glu Glu Leu Lys Glu
45                  50                  55                  60 cta gat cgg ctc aac gaa aca ctc tct tca tgt cac gag cag agc aag      304
Leu Asp Arg Leu Asn Glu Thr Leu Ser Ser Cys His Glu Gln Ser Lys
                 65                  70                  75 acg ctt cac aat gct aaa gcc gtt aaa gat ctc cgg tct aaa atg gac      352
Thr Leu His Asn Ala Lys Ala Val Lys Asp Leu Arg Ser Lys Met Asp
             80                  85                  90 ggt gac gtt gga gtc gcg ttg aag aag gcg aag atg att aaa gtt aaa      400
Gly Asp Val Gly Val Ala Leu Lys Lys Ala Lys Met Ile Lys Val Lys
         95                 100                 105 ctc gag gcg cta gat cgt gcc aat gct gct aat cgg agt ctc cct ggc      448
Leu Glu Ala Leu Asp Arg Ala Asn Ala Ala Asn Arg Ser Leu Pro Gly
    110                 115                 120 tgt gga cct ggt tct tcc tcc gat cga acc agg acc tct gtc ctc aat      496
Cys Gly Pro Gly Ser Ser Ser Asp Arg Thr Arg Thr Ser Val Leu Asn
125                 130                 135                 140 ggt ctc agg aag aaa ttg atg gac tct atg gat agt ttc aac cga ttg      544
Gly Leu Arg Lys Lys Leu Met Asp Ser Met Asp Ser Phe Asn Arg Leu
                145                 150                 155 agg gag ctt atc tcg tcc gag tat aga gaa act gta cag agg agg tac      592
```

-continued

```
Arg Glu Leu Ile Ser Ser Glu Tyr Arg Glu Thr Val Gln Arg Arg Tyr
            160                 165                 170 ttc acc gtc acc ggc gag aat ccg gat gaa cga acc cta gat cga ctg      640
Phe Thr Val Thr Gly Glu Asn Pro Asp Glu Arg Thr Leu Asp Arg Leu
        175                 180                 185 att tcc act gga gag agt gag aga ttc ttg cag aaa gca ata caa gaa      688
Ile Ser Thr Gly Glu Ser Glu Arg Phe Leu Gln Lys Ala Ile Gln Glu
    190                 195                 200 caa gga aga gga agg gtg tta gac acc att aac gag att caa gaa agg      736
Gln Gly Arg Gly Arg Val Leu Asp Thr Ile Asn Glu Ile Gln Glu Arg
205                 210                 215                 220 cat gat cgc gtt aaa gac att gag aag aat ctc agg gag ctt cac cag      784
His Asp Arg Val Lys Asp Ile Glu Lys Asn Leu Arg Glu Leu His Gln
                225                 230                 235 gtg ttt cta gac atg gcc gtg ctg gta gag cac cag gga gct cag ctt      832
Val Phe Leu Asp Met Ala Val Leu Val Glu His Gln Gly Ala Gln Leu
            240                 245                 250 gat gac atc gag agt cat gtg ggt cga gct agc tcc ttt atc aga ggc      880
Asp Asp Ile Glu Ser His Val Gly Arg Ala Ser Ser Phe Ile Arg Gly
        255                 260                 265 gga act gac cag cta caa acc gct cgg gtt tac cag aag aac acg cga      928
Gly Thr Asp Gln Leu Gln Thr Ala Arg Val Tyr Gln Lys Asn Thr Arg
    270                 275                 280 aaa tgg aca tgt att gcc att att att ctc atc atc atc ata act gtt      976
Lys Trp Thr Cys Ile Ala Ile Ile Ile Leu Ile Ile Ile Ile Thr Val
285                 290                 295                 300 gtg gtt ctt gct gtt ttaaaaccgt ggaacaacag cagtggcggc ggcggcggtg     1031
Val Val Leu Ala Val
            305 gtggtggtgg gggtaccact ggaggaagtc aaccaaattc agggacacca ccaaatcctc   1091 ctcaggcaag gcgtctattg cgttgaagtt gaagttgaag ttgagtttcg ttatttgcat   1151 atatattctt tctttgaaaa accttattat caaaccagct tgtgttact actttctact    1211 gctggtttgt tgttaatctc ccgtttattt ggttttttgtg aaagaattta aaatgtgggt  1271 tagatgagaa aattagtaca acattctctt gtatctatgt ttgctaccct gacgtagctc  1331 gag                                                                 1334

<210> SEQ ID NO 4
<211> LENGTH: 305
<212> TYPE: PRT
<213> ORGANISM: Arabidopsis thaliana

<400> SEQUENCE: 4

Met Asn Asp Leu Phe Ser Ser Phe Ser Arg Phe Arg Ser Gly Glu
1               5                   10                  15

Pro Ser Pro Arg Arg Asp Val Ala Gly Gly Gly Asp Gly Val Gln Met
                20                  25                  30

Ala Asn Pro Ala Gly Ser Thr Gly Gly Val Asn Leu Asp Lys Phe Phe
            35                  40                  45

Glu Asp Val Glu Ser Val Lys Glu Glu Leu Lys Glu Leu Asp Arg Leu
        50                  55                  60

Asn Glu Thr Leu Ser Ser Cys His Glu Gln Ser Lys Thr Leu His Asn
65                  70                  75                  80

Ala Lys Ala Val Lys Asp Leu Arg Ser Lys Met Asp Gly Asp Val Gly
                85                  90                  95

Val Ala Leu Lys Lys Ala Lys Met Ile Lys Val Lys Leu Glu Ala Leu
            100                 105                 110
```

Asp Arg Ala Asn Ala Ala Asn Arg Ser Leu Pro Gly Cys Gly Pro Gly
        115                 120                 125

Ser Ser Ser Asp Arg Thr Arg Thr Ser Val Leu Asn Gly Leu Arg Lys
    130                 135                 140

Lys Leu Met Asp Ser Met Asp Ser Phe Asn Arg Leu Arg Glu Leu Ile
145                 150                 155                 160

Ser Ser Glu Tyr Arg Glu Thr Val Gln Arg Arg Tyr Phe Thr Val Thr
                165                 170                 175

Gly Glu Asn Pro Asp Glu Arg Thr Leu Asp Arg Leu Ile Ser Thr Gly
            180                 185                 190

Glu Ser Glu Arg Phe Leu Gln Lys Ala Ile Gln Glu Gln Gly Arg Gly
        195                 200                 205

Arg Val Leu Asp Thr Ile Asn Glu Ile Gln Glu Arg His Asp Arg Val
    210                 215                 220

Lys Asp Ile Glu Lys Asn Leu Arg Glu Leu His Gln Val Phe Leu Asp
225                 230                 235                 240

Met Ala Val Leu Val Glu His Gln Gly Ala Gln Leu Asp Asp Ile Glu
                245                 250                 255

Ser His Val Gly Arg Ala Ser Ser Phe Ile Arg Gly Gly Thr Asp Gln
            260                 265                 270

Leu Gln Thr Ala Arg Val Tyr Gln Lys Asn Thr Arg Lys Trp Thr Cys
        275                 280                 285

Ile Ala Ile Ile Ile Leu Ile Ile Ile Thr Val Val Leu Ala
    290                 295                 300

Val
305

<210> SEQ ID NO 5
<211> LENGTH: 1205
<212> TYPE: DNA
<213> ORGANISM: Nicotiana tabacum

<400> SEQUENCE: 5
tttagattta ctcttatatt agtttgtttg tttaattgga cggttgttat atcttttct       60 taatatgaga tttatgtcgt tattaatgtt tttctcttga gggttcataa agagattat     120 cgtgtacctg ggggtaggtc aaatgagaag gggtgtaatt tttgtttttt ttttaggttt   180
tattgtgttt tattattcgt accgatttta ttatttata ttttaaatc ttataagttt     240 tgtaacttcc ccaggtggtc ttctggaaac tggtatctgt ttaagagtaa aaaaggtacc   300
gacttatctt tcttggtggt ggttttacta ctattcgtct tcttattatc gttttgttca   360
ggtaaaagat cacaagaaga ccacgaagga acgtgaacg tcaacgactc gtggggaga    420 ttgcttcctt aatcgggata agtgaaccga gagttatagt agttcaactc gaggaactga   480
aagttggttt tgtcggtaca ggttcttatg aactacgtta agaaagttta aggagaggtt   540
aaggaagtgt cgaagtacgg aaagaactta aggtattga cataggtagt gaacaggaga    600
gggaacgaga acttaacgga aaacgttctt gcagagtgaa actggacatc tatactcaca   660
tagttcttga cgaagtagtc ctaaaagagg acactgccat attatagcag caacttgaca   720
aagggatata agtctacggt agaaaacgga atcgagcaac ttgactaagt aactgagaac   780
ttcaaagaag gaattaggca agtgttgact tcaagagcag gacagtctac ttgaaggccc   840
aggtgtaggc ccctccgaag ctaagcgacg taaactagac agattccgaa gctctgcttg   900
aaactactta aaccgaaaga agttacggta cctttgcagt aataggtaca acctagaatc   960

-continued

```
tagaaattgc cgaaatcgca acacttctca gaacgaaaaa agtacccttc taacctcaac      1020
ccttatctaa aagagctccg gaaactcaag cagaaattac cgaagttgta gaagcttctt      1080
aaacagctct aactgaggcg gtcattacag agggtaaaga taccgcactc tcaggctaac      1140
tagcagtcga gactttgctc tctttctagg acttttatct agtaagtaaa actctaccct      1200
aaacc                                                                 1205
```

<210> SEQ ID NO 6
<211> LENGTH: 80
<212> TYPE: PRT
<213> ORGANISM: Nicotiana tabacum

<400> SEQUENCE: 6

```
Ser Asn Pro Glu Glu Lys Glu Phe Leu Asp Trp Ser Lys Arg Val Ile
1               5                   10                  15

Ile Ile Glu Gly Ile Gly Arg Gly Leu Leu Tyr Leu His Arg Asp Ser
            20                  25                  30

Arg Leu Arg Ile Ile His Arg Asp Leu Lys Ala Ser Asn Ile Leu Leu
        35                  40                  45

Asp Glu Gln Leu Asn Pro Lys Ile Ser Asp Phe Gly Met Ala Arg Ile
    50                  55                  60

Phe Pro Gly Ser Gln Asp Gln Ala Asn Thr Glu Arg Val Val Gly Thr
65                  70                  75                  80
```

<210> SEQ ID NO 7
<211> LENGTH: 77
<212> TYPE: PRT
<213> ORGANISM: Ipomoea trifida

<400> SEQUENCE: 7

```
Asn Lys Gln Arg Ser Ser Leu Leu Asn Trp Gln Thr Arg Phe Asn Ile
1               5                   10                  15

Ile Cys Gly Ile Ala Arg Gly Leu Leu Tyr Leu His Gln Asp Ser Arg
            20                  25                  30

Phe Arg Ile Ile His Arg Asp Leu Lys Ala Ser Asn Ile Leu Leu Asp
        35                  40                  45

Lys Glu Met Asn Pro Lys Ile Ser Asp Phe Gly Met Ala Arg Ile Phe
    50                  55                  60

Gly Gly Asp Glu Thr Asp Ala Asn Asn Thr Lys Arg Val
65                  70                  75
```

<210> SEQ ID NO 8
<211> LENGTH: 72
<212> TYPE: PRT
<213> ORGANISM: brassica campestris

<400> SEQUENCE: 8

```
Leu Asn Trp Lys Asp Arg Phe Ala Ile Thr Asn Gly Val Ala Arg Gly
1               5                   10                  15

Leu Leu Tyr Leu His Gln Asp Ser Arg Phe Arg Ile Ile His Arg Asp
            20                  25                  30

Leu Lys Pro Gly Asn Ile Leu Leu Asp Lys Tyr Met Ile Pro Lys Ile
        35                  40                  45

Ser Asp Phe Gly Met Ala Arg Ile Phe Ala Arg Asp Glu Ile Gln Ala
    50                  55                  60

Arg Thr Asp Asn Ala Val Gly Thr
65                  70
```

<210> SEQ ID NO 9
<211> LENGTH: 72
<212> TYPE: PRT
<213> ORGANISM: Brassica oleracea

<400> SEQUENCE: 9

```
Lys Lys Arg Ser Ser Asn Leu Asn Trp Lys Asp Arg Phe Ala Ile Ile
1               5                   10                  15

Asn Gly Val Ala Arg Gly Leu Leu Tyr Leu His Gln Asp Ser Arg Phe
            20                  25                  30

Arg Ile Ile His Arg Asp Met Lys Pro Ser Asn Ile Leu Leu Asp Lys
        35                  40                  45

Tyr Met Ile Pro Lys Ile Ser Asp Phe Gly Met Ala Arg Ile Phe Ala
    50                  55                  60

Arg Asp Glu Thr Glu Ala Asn Thr
65                  70
```

<210> SEQ ID NO 10
<211> LENGTH: 66
<212> TYPE: PRT
<213> ORGANISM: Nicotiana tabacum

<400> SEQUENCE: 10

```
Gly Leu Leu Cys Val Gln Glu Tyr Ala Glu Asp Arg Pro Asn Val Ser
1               5                   10                  15

Val Val Leu Ser Met Leu Thr Ser Glu Ile Ser Asp Leu Pro Ser Pro
            20                  25                  30

Lys Gln Pro Ala Phe Thr Thr Arg Pro Ser Cys Ser Glu Lys Glu Ser
        35                  40                  45

Ser Lys Thr Gln Gly Ser Val Asn Thr Val Ser Ile Thr Ile Met Glu
    50                  55                  60

Gly Arg
65
```

<210> SEQ ID NO 11
<211> LENGTH: 70
<212> TYPE: PRT
<213> ORGANISM: Ipomoea trifida

<400> SEQUENCE: 11

```
Gly Leu Leu Cys Val Gln Glu Gln Ala Glu Asp Arg Pro Asn Met Ala
1               5                   10                  15

Thr Val Val Leu Met Leu Gly Ser Glu Ser Ala Thr Leu Pro Gln Pro
            20                  25                  30

Lys His Pro Gly Phe Cys Leu Gly Ser Arg Pro Ala Asp Met Asp Ser
        35                  40                  45

Ser Thr Ser Asn Cys Asp Glu Ser Cys Thr Val Asn Gln Val Thr Val
    50                  55                  60

Thr Met Leu Asp Gly Arg
65                  70
```

<210> SEQ ID NO 12
<211> LENGTH: 73
<212> TYPE: PRT
<213> ORGANISM: brassica campestris

<400> SEQUENCE: 12

```
Gly Leu Leu Cys Ile Gln Glu Arg Ala Glu His Arg Pro Thr Met Ser
```

```
                 1               5                  10                  15
Ser Val Val Trp Met Leu Gly Ser Glu Ala Thr Glu Ile Pro Gln Pro
                20                  25                  30

Lys Pro Pro Val Tyr Cys Leu Ile Ala Ser Tyr Ala Asn Asn Pro
                35                  40                  45

Ser Ser Ser Arg Gln Phe Asp Asp Glu Ser Trp Thr Val Asp Lys
        50                  55                  60

Tyr Thr Trp Ser Val Ile Asp Ala Arg
 65                  70
```

<210> SEQ ID NO 13
<211> LENGTH: 73
<212> TYPE: PRT
<213> ORGANISM: Brassica oleracea

<400> SEQUENCE: 13

```
Gly Leu Leu Cys Ile Gln Glu Arg Ala Glu Asp Arg Pro Thr Met Ser
 1               5                  10                  15

Ser Val Val Trp Met Leu Gly Ser Glu Ala Thr Asp Ile Pro Gln Pro
                20                  25                  30

Lys Pro Pro Ile Tyr Cys Leu Ile Thr Ser Tyr Tyr Ala Asn Asn Pro
                35                  40                  45

Ser Ser Ser Arg Gln Phe Glu Asp Asp Glu Ser Trp Thr Val Asn Lys
        50                  55                  60

Tyr Thr Cys Ser Val Ile Asp Ala Arg
 65                  70
```

<210> SEQ ID NO 14
<211> LENGTH: 124
<212> TYPE: PRT
<213> ORGANISM: Nicotiana tabacum

<400> SEQUENCE: 14

```
Arg Phe Arg Ala Val Thr Ser Ala Tyr Tyr Arg Ser Ala Val Gly Ala
 1               5                  10                  15

Leu Leu Val Tyr Asp Ile Ser Arg Lys Thr Thr Phe Glu Asn Ile Gln
                20                  25                  30

Cys Trp Leu Asp Glu Leu His Thr His Cys Asp Thr Thr Val Ala Arg
                35                  40                  45

Met Leu Val Gly Asn Lys Cys Asp Leu Glu Asn Ile Arg Asp Val Ser
        50                  55                  60

Ile Tyr Glu Gly Lys Asn Leu Ala Glu Glu Gly Leu Phe Phe Ile
 65                  70                  75                  80

Glu Thr Ser Ala Leu Asp Ser Thr Asn Val Lys Gln Pro Leu Lys Leu
                85                  90                  95

Ser Ser Ala Gln Ile Tyr Gln Asn Leu Ser Arg Lys Val Leu His Ser
            100                 105                 110

Asp Ser Tyr Lys Thr Glu Leu Ser Val His Pro Val
            115                 120
```

<210> SEQ ID NO 15
<211> LENGTH: 124
<212> TYPE: PRT
<213> ORGANISM: Glycine max

<400> SEQUENCE: 15

```
Arg Phe Arg Ala Val Thr Ser Ala Tyr Tyr Arg Gly Ala Val Gly Ala
 1               5                  10                  15
```

-continued

Leu Ile Val Tyr Asp Ile Ser Arg Arg Thr Thr Phe Asp Ser Val Gly
              20                  25                  30

Arg Trp Leu Asp Glu Leu Lys Thr His Cys Asp Thr Thr Val Ala Met
         35                  40                  45

Met Leu Val Gly Asn Lys Cys Asp Leu Glu Asn Ile Arg Ala Val Ser
     50                  55                  60

Ile Asp Glu Gly Lys Ser Leu Ala Glu Ala Gly Leu Phe Phe Met
65                  70                  75                  80

Glu Thr Ser Ala Leu Asp Ser Thr Asn Val Lys Met Ala Phe Glu Met
                 85                  90                  95

Val Ile Arg Glu Ile Tyr Asn Asn Val Ser Arg Lys Val Leu Asn Ser
             100                 105                 110

Glu Thr Tyr Lys Ala Glu Leu Ser Val Asn Arg Val
            115                 120

<210> SEQ ID NO 16
<211> LENGTH: 124
<212> TYPE: PRT
<213> ORGANISM: Lotus japonicus

<400> SEQUENCE: 16

Arg Phe Arg Ala Val Thr Ser Ala Tyr Tyr Arg Gly Ala Val Gly Ala
1               5                   10                  15

Leu Ile Val Tyr Asp Ile Thr Arg Arg Thr Thr Phe Asp Ser Val Ser
              20                  25                  30

Arg Trp Leu Asp Glu Leu Lys Thr His Cys Asp Thr Thr Val Ala Met
         35                  40                  45

Met Leu Val Gly Asn Lys Cys Asp Leu Glu Asn Ile Arg Ala Val Ser
     50                  55                  60

Ile Glu Glu Gly Lys Ser Leu Ala Glu Ala Gln Gly Leu Phe Phe Met
65                  70                  75                  80

Glu Thr Ser Ala Leu Asp Ser Thr Asn Val Arg Thr Ala Phe Glu Met
                 85                  90                  95

Val Ile Arg Glu Ile Tyr Asn Asn Val Ser Arg Lys Val Leu Asn Ser
             100                 105                 110

Asp Thr Tyr Lys Ala Glu Leu Ser Val Asp Arg Val
            115                 120

<210> SEQ ID NO 17
<211> LENGTH: 124
<212> TYPE: PRT
<213> ORGANISM: Arabidopsis thaliana

<400> SEQUENCE: 17

Arg Phe Arg Ala Val Thr Ser Ala Tyr Tyr Arg Gly Ala Val Gly Ala
1               5                   10                  15

Leu Val Val Tyr Asp Ile Thr Arg Arg Thr Thr Phe Glu Ser Val Gly
              20                  25                  30

Arg Trp Leu Asp Glu Leu Lys Ile His Ser Asp Thr Thr Val Ala Arg
         35                  40                  45

Met Leu Val Gly Asn Lys Cys Asp Leu Glu Asn Ile Arg Ala Val Ser
     50                  55                  60

Val Glu Glu Gly Lys Ala Leu Ala Glu Glu Gly Leu Phe Phe Val
65                  70                  75                  80

Glu Thr Ser Ala Leu Asp Ser Thr Asn Val Lys Thr Ala Phe Glu Met
                 85                  90                  95

```
Val Ile Leu Asp Ile Tyr Asn Asn Val Ser Arg Lys Gln Leu Asn Ser
                100                 105                 110

Asp Thr Tyr Lys Asp Glu Leu Thr Val Asn Arg Val
        115                 120

<210> SEQ ID NO 18
<211> LENGTH: 124
<212> TYPE: PRT
<213> ORGANISM: Arabidopsis thaliana

<400> SEQUENCE: 18

Arg Phe Arg Ala Val Thr Ser Ala Tyr Tyr Arg Gly Ala Val Gly Ala
1               5                   10                  15

Leu Val Val Tyr Asp Ile Thr Arg Ser Ser Thr Phe Glu Asn Val Gly
                20                  25                  30

Arg Trp Leu Asp Glu Leu Asn Thr His Ser Asp Thr Thr Val Ala Lys
            35                  40                  45

Met Leu Ile Gly Asn Lys Cys Asp Leu Glu Ser Ile Arg Ala Val Ser
        50                  55                  60

Val Glu Glu Gly Lys Ser Leu Ala Glu Ser Gly Leu Phe Phe Met
65                  70                  75                  80

Glu Thr Ser Ala Leu Asp Ser Thr Asn Val Lys Thr Ala Phe Glu Met
                85                  90                  95

Val Ile Arg Glu Ile Tyr Ser Asn Ile Ser Arg Lys Gln Leu Asn Ser
                100                 105                 110

Asp Ser Tyr Lys Glu Glu Leu Thr Val Asn Arg Val
        115                 120

<210> SEQ ID NO 19
<211> LENGTH: 124
<212> TYPE: PRT
<213> ORGANISM: Nicotiana tabacum

<400> SEQUENCE: 19

Arg Phe Arg Ala Val Thr Ser Ala Tyr Tyr Arg Gly Ala Phe Gly Ala
1               5                   10                  15

Leu Val Val Tyr Asp Ile Thr Arg Arg Thr Thr Phe Asp Ser Ile Pro
                20                  25                  30

Arg Trp Leu Asp Glu Leu Lys Thr His Ser Asp Thr Thr Val Ala Arg
            35                  40                  45

Met Leu Val Gly Asn Lys Cys Asp Leu Asp Asn Ile Arg Ala Val Ser
        50                  55                  60

Val Glu Glu Gly Lys Ser Leu Ala Glu Ser Gly Met Phe Phe Met
65                  70                  75                  80

Glu Thr Ser Ala Leu Asp Ala Thr Asn Val Asn Lys Ala Phe Asp Met
                85                  90                  95

Val Ile Arg Glu Ile Tyr Asn Ser Val Ser Arg Lys Val Leu Asn Ser
                100                 105                 110

Asp Ser Tyr Lys Ala Glu Leu Ser Val Asn Arg Val
        115                 120

<210> SEQ ID NO 20
<211> LENGTH: 168
<212> TYPE: PRT
<213> ORGANISM: Nicotiana tabacum

<400> SEQUENCE: 20
```

```
Leu Ile Phe Ser Leu Glu Thr Phe Leu Leu Val Leu Phe Phe Thr
1               5                   10                  15

Leu Val Ser Ser Ala Ser Glu Ile Phe Phe Glu Ser Phe Asp
            20              25              30

Asp Gly Trp Arg Ser Arg Trp Val Lys Ser Asp Trp Lys Ile Ser Glu
            35              40              45

Gly Lys Ala Gly Ser Phe Lys His Thr Ala Gly Thr Trp Ala Gly Asp
    50              55              60

Pro Asp Asp Lys Gly Ile His Thr Thr Asn Asp Ala Lys His Phe Ala
65              70              75              80

Val Ser Ala Lys Ile Pro Glu Phe Ser Asn Lys Asn Arg Thr Leu Val
            85              90              95

Val Gln Tyr Ser Ile Lys Phe Glu Pro Asp Ile Glu Cys Gly Arg Gly
            100             105             110

Tyr Ile Lys Leu Leu Ser Gly Tyr Val His Pro Lys Lys Phe Gly Gly
            115             120             125

Asp Thr Pro Tyr Ser Phe Met Phe Gly Ala Asp Ile Cys Gly Ser Gln
            130             135             140

Thr Lys Lys Pro Ser Cys Leu Tyr Phe Pro Tyr Pro Gly Ala Glu Leu
145             150             155             160

Pro Pro Leu Pro Glu Arg Asn Leu
                165
```

<210> SEQ ID NO 21
<211> LENGTH: 165
<212> TYPE: PRT
<213> ORGANISM: Arabidopsis thaliana

<400> SEQUENCE: 21

```
Asn Lys Leu Ser Phe Phe Cys Phe Phe Phe Leu Val Ser Val Leu Thr
1               5                   10                  15

Leu Ala Pro Leu Ala Phe Ser Glu Ile Phe Leu Glu Glu His Phe Glu
            20              25              30

Gly Gly Trp Lys Ser Arg Trp Val Leu Ser Asp Trp Lys Arg Asn Glu
            35              40              45

Gly Lys Ala Gly Thr Phe Lys His Thr Ala Gly Lys Trp Pro Gly Asp
    50              55              60

Pro Asp Asn Lys Gly Ile Gln Thr Tyr Asn Asp Ala Lys His Tyr Ala
65              70              75              80

Ile Ser Ala Lys Ile Pro Glu Phe Ser Asn Lys Asn Arg Thr Leu Val
            85              90              95

Val Gln Tyr Ser Val Lys Ile Glu Gln Asp Ile Glu Cys Gly Gly Ala
            100             105             110

Tyr Ile Lys Leu Leu Ser Gly Tyr Val Asn Gln Lys Gln Phe Gly Gly
            115             120             125

Asp Thr Pro Tyr Ser Leu Met Phe Gly Pro Asp Ile Cys Gly Thr Gln
            130             135             140

Thr Lys Lys Leu His Val Ile Val Ser Tyr Gln Gly Gln Asn Tyr Pro
145             150             155             160

Ile Lys Lys Asp Leu
                165
```

<210> SEQ ID NO 22
<211> LENGTH: 82
<212> TYPE: PRT
<213> ORGANISM: Nicotiana tabacum

```
<400> SEQUENCE: 22

Gly Val Trp Met Glu Pro Asp Tyr Ala Lys Thr Asp Ser Arg Lys
1               5                   10                  15

Cys Leu Pro Ile Gly Glu Ala Glu Lys Glu Ala Phe Glu Glu Ala Glu
            20                  25                  30

Lys Val Arg Lys Ala Lys Glu Glu Glu Ala Gln Arg Ala Arg Glu
        35                  40                  45

Glu Gly Glu Arg Arg Lys Arg Glu Arg Gly Arg Asp Arg His Arg Asp
    50                  55                  60

Arg Tyr Lys Lys Arg Tyr His His Asp Tyr Met Asp Asp Tyr His Asp
65                  70                  75                  80

Glu Leu

<210> SEQ ID NO 23
<211> LENGTH: 85
<212> TYPE: PRT
<213> ORGANISM: Arabidopsis thaliana

<400> SEQUENCE: 23

Ile Leu Ile Cys Asp Asp Pro Ala Tyr Ala Arg Ser Ile Val Asp Asp
1               5                   10                  15

Tyr Phe Ala Gln His Arg Glu Ser Glu Lys Glu Leu Phe Ala Glu Ala
            20                  25                  30

Glu Lys Glu Arg Lys Ala Arg Glu Asp Glu Glu Ala Arg Ile Ala Arg
        35                  40                  45

Glu Glu Gly Glu Arg Arg Lys Glu Arg Asp His Arg Tyr Gly Asp
    50                  55                  60

Arg Arg Arg Arg Tyr Lys Arg Pro Asn Pro Arg Asp Tyr Met Asp Asp
65                  70                  75                  80

Tyr His Asp Glu Leu
                85

<210> SEQ ID NO 24
<211> LENGTH: 310
<212> TYPE: PRT
<213> ORGANISM: Arabidopsis thaliana

<400> SEQUENCE: 24

Met Asn Asp Leu Met Thr Lys Ser Phe Met Ser Tyr Val Asp Leu Lys
1               5                   10                  15

Lys Ala Ala Met Lys Asp Met Glu Ala Gly Pro Asp Phe Asp Leu Glu
            20                  25                  30

Met Ala Ser Thr Lys Ala Asp Lys Met Asp Glu Asn Leu Ser Ser Phe
        35                  40                  45

Leu Glu Glu Ala Glu Tyr Val Lys Ala Glu Met Gly Leu Ile Ser Glu
    50                  55                  60

Thr Leu Ala Arg Ile Glu Gln Tyr His Glu Glu Ser Lys Gly Val His
65                  70                  75                  80

Lys Ala Glu Ser Val Lys Ser Leu Arg Asn Lys Ile Ser Asn Glu Ile
                85                  90                  95

Val Ser Gly Leu Arg Lys Ala Lys Ser Ile Lys Ser Lys Leu Glu Glu
            100                 105                 110

Met Asp Lys Ala Asn Lys Glu Ile Lys Arg Leu Ser Gly Thr Pro Val
        115                 120                 125

Tyr Arg Ser Arg Thr Ala Val Thr Asn Gly Leu Arg Lys Lys Leu Lys
```

```
          130                 135                 140
Glu Val Met Met Glu Phe Gln Gly Leu Arg Gln Lys Met Met Ser Glu
145                 150                 155                 160

Tyr Lys Glu Thr Val Glu Arg Arg Tyr Phe Thr Val Thr Gly Glu His
                165                 170                 175

Ala Asn Asp Glu Met Ile Glu Lys Ile Ile Thr Asp Asn Ala Gly Gly
            180                 185                 190

Glu Glu Phe Leu Thr Arg Ala Ile Gln Glu His Gly Lys Gly Lys Val
        195                 200                 205

Leu Glu Thr Val Val Glu Ile Gln Asp Arg Tyr Asp Ala Ala Lys Glu
    210                 215                 220

Ile Glu Lys Ser Leu Leu Glu Leu His Gln Val Phe Leu Asp Met Ala
225                 230                 235                 240

Val Met Val Glu Ser Gln Gly Glu Gln Met Asp Glu Ile Glu His His
                245                 250                 255

Val Ile Asn Ala Ser His Tyr Val Ala Asp Gly Ala Asn Glu Leu Lys
            260                 265                 270

Thr Ala Lys Ser His Gln Arg Asn Ser Arg Lys Trp Met Cys Ile Gly
        275                 280                 285

Ile Ile Val Leu Leu Leu Ile Ile Leu Ile Val Val Ile Pro Ile Ile
    290                 295                 300

Thr Ser Phe Ser Ser Ser
305                 310

<210> SEQ ID NO 25
<211> LENGTH: 259
<212> TYPE: PRT
<213> ORGANISM: Homo sapiens

<400> SEQUENCE: 25

Met Asp Glu Phe Phe Glu Gln Val Glu Glu Ile Arg Gly Phe Ile Asp
1               5                   10                  15

Lys Ile Ala Glu Asn Val Glu Glu Val Lys Arg Lys His Ser Ala Ile
            20                  25                  30

Leu Ala Ser Pro Asn Pro Asp Glu Lys Thr Lys Val Glu Leu Glu Glu
        35                  40                  45

Leu Met Ser Asp Ile Lys Lys Thr Ala Asn Lys Val Arg Ser Lys Leu
    50                  55                  60

Lys Ser Ile Glu Gln Ser Ile Glu Gln Glu Glu Gly Leu Asn Arg Ser
65                  70                  75                  80

Ser Ala Asp Leu Arg Ile Arg Lys Thr Gln His Ser Thr Leu Ser Arg
                85                  90                  95

Lys Phe Val Glu Val Met Ser Glu Tyr Asn Ala Thr Gln Ser Val Tyr
            100                 105                 110

Arg Glu Arg Cys Lys Gly Arg Ile Gln Arg Gln Leu Glu Ile Thr Gly
        115                 120                 125

Arg Thr Thr Thr Ser Glu Glu Leu Glu Asp Met Leu Glu Ser Gly Asn
    130                 135                 140

Pro Ala Ile Phe Ala Ser Gly Ile Ile Met Asp Ser Ser Ile Ser Lys
145                 150                 155                 160

Gln Ala Leu Ser Glu Ile Glu Thr Arg His Ser Glu Ile Ile Lys Leu
                165                 170                 175

Glu Asn Ser Ile Arg Glu Leu His Asp Met Phe Met Asp Met Ala Met
            180                 185                 190
```

```
Leu Val Glu Ser Gln Gly Glu Met Ile Asp Arg Ile Glu Tyr Asn Val
            195                 200                 205

Glu His Ala Val Asp Tyr Val Glu Arg Ala Val Ser Asp Thr Lys Lys
        210                 215                 220

Ala Val Lys Tyr Gln Ser Lys Ala Arg Lys Lys Ile Met Ile Ile
225                 230                 235                 240

Ile Cys Cys Val Ile Leu Gly Ile Val Ile Ala Ser Thr Val Gly Gly
                245                 250                 255

Ile Phe Ala

<210> SEQ ID NO 26
<211> LENGTH: 288
<212> TYPE: PRT
<213> ORGANISM: Homo sapiens

<400> SEQUENCE: 26

Met Lys Asp Arg Thr Gln Val Leu Arg Thr Arg Arg Asn Ser Asp Asp
1               5                   10                  15

Lys Glu Glu Val Val His Val Asp Arg Asp His Phe Met Asp Glu Phe
            20                  25                  30

Phe Glu Gln Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Arg Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Ser Thr Ala Pro Arg Pro Ile Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Pro Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Ile Ile Ile Cys Cys Val
            260                 265                 270

Val Leu Gly Val Val Leu Ala Ser Ser Ile Gly Cys Thr Leu Gly Leu
        275                 280                 285

<210> SEQ ID NO 27
<211> LENGTH: 291
```

```
<212> TYPE: PRT
<213> ORGANISM: Drosophila melanogaster

<400> SEQUENCE: 27

Met Thr Lys Asp Arg Leu Ala Ala Leu His Ala Ala Gln Ser Asp Asp
1               5                   10                  15

Glu Glu Glu Thr Glu Val Ala Val Asn Val Asp Gly His Asp Ser Tyr
            20                  25                  30

Met Asp Asp Phe Phe Ala Gln Val Glu Glu Ile Arg Gly Met Ile Asp
            35                  40                  45

Lys Val Gln Asp Asn Val Glu Glu Val Lys Lys His Ser Ala Ile
50                  55                  60

Leu Ser Ala Pro Gln Thr Asp Glu Lys Thr Lys Gln Glu Leu Glu Asp
65                  70                  75                  80

Leu Met Ala Asp Ile Lys Lys Asn Ala Asn Arg Val Arg Gly Lys Leu
                85                  90                  95

Lys Gly Ile Glu Gln Asn Ile Glu Gln Glu Gln Gln Asn Lys Ser
            100                 105                 110

Ser Ala Asp Leu Arg Ile Arg Lys Thr Gln His Ser Thr Leu Ser Arg
            115                 120                 125

Lys Phe Val Glu Val Met Thr Glu Tyr Asn Arg Thr Gln Thr Asp Tyr
    130                 135                 140

Arg Glu Arg Cys Lys Gly Arg Ile Gln Arg Gln Leu Glu Ile Thr Gly
145                 150                 155                 160

Arg Pro Thr Asn Asp Asp Glu Leu Glu Lys Met Leu Glu Glu Gly Asn
                165                 170                 175

Ser Ser Val Phe Thr Gln Gly Ile Ile Met Glu Thr Gln Gln Ala Lys
            180                 185                 190

Gln Thr Leu Ala Asp Ile Glu Ala Arg His Gln Asp Ile Met Lys Leu
            195                 200                 205

Glu Thr Ser Ile Lys Glu Leu His Asp Met Phe Met Asp Met Ala Met
            210                 215                 220

Leu Val Glu Ser Gln Gly Glu Met Ile Asp Arg Ile Glu Tyr His Val
225                 230                 235                 240

Glu His Ala Met Asp Tyr Val Gln Thr Ala Thr Gln Asp Thr Lys Lys
                245                 250                 255

Ala Leu Lys Tyr Gln Ser Lys Ala Arg Arg Lys Lys Ile Met Ile Leu
            260                 265                 270

Ile Cys Leu Thr Val Leu Gly Ile Leu Ala Ala Ser Tyr Val Ser Ser
            275                 280                 285

Tyr Phe Met
    290

<210> SEQ ID NO 28
<211> LENGTH: 6
<212> TYPE: PRT
<213> ORGANISM: Nicotiana tabacum

<400> SEQUENCE: 28

Leu Gln Val Ala Arg Lys
1               5

<210> SEQ ID NO 29
<211> LENGTH: 6
<212> TYPE: PRT
<213> ORGANISM: Drosophila melanogaster
```

-continued

```
<400> SEQUENCE: 29

Thr Lys Lys Ala Leu Lys
1               5

<210> SEQ ID NO 30
<211> LENGTH: 6
<212> TYPE: PRT
<213> ORGANISM: Rattus sp.

<400> SEQUENCE: 30

Thr Lys Lys Ala Val Lys
1               5

<210> SEQ ID NO 31
<211> LENGTH: 6
<212> TYPE: PRT
<213> ORGANISM: yeast sp.

<400> SEQUENCE: 31

Thr Asp Lys Ala Val Lys
1               5

<210> SEQ ID NO 32
<211> LENGTH: 6
<212> TYPE: PRT
<213> ORGANISM: yeast sp.

<400> SEQUENCE: 32

Thr Asn Lys Ala Val Lys
1               5

<210> SEQ ID NO 33
<211> LENGTH: 13
<212> TYPE: PRT
<213> ORGANISM: Nicotiana tabacum

<400> SEQUENCE: 33

Asp Gln Ser Asp Ser His Ala Ile Glu Met Gly Asp Ile
1               5                   10

<210> SEQ ID NO 34
<211> LENGTH: 5
<212> TYPE: PRT
<213> ORGANISM: Nicotiana tabacum

<400> SEQUENCE: 34

Gly Cys Gly Pro Gly
1               5

<210> SEQ ID NO 35
<211> LENGTH: 25
<212> TYPE: PRT
<213> ORGANISM: Nicotiana tabacum

<400> SEQUENCE: 35

Leu Glu Arg Asn Leu Lys Glu Leu His Gln Val Phe Leu Asp Met Ala
1               5                   10                  15

Val Leu Val Glu Ser Gln Gly Ala Gln
            20                  25

<210> SEQ ID NO 36
<211> LENGTH: 25
<212> TYPE: PRT
<213> ORGANISM: Arabidopsis thaliana
```

```
<400> SEQUENCE: 36

Ile Glu Lys Ser Leu Leu Glu Leu His Gln Val Phe Leu Asp Met Ala
1               5                   10                  15

Val Met Val Glu Ser Gln Gly Glu Gln
            20                  25

<210> SEQ ID NO 37
<211> LENGTH: 25
<212> TYPE: PRT
<213> ORGANISM: Homo sapiens

<400> SEQUENCE: 37

Leu Glu Asn Ser Ile Arg Glu Leu His Asp Met Phe Met Asp Met Ala
1               5                   10                  15

Met Leu Val Glu Ser Gln Gly Glu Met
            20                  25

<210> SEQ ID NO 38
<211> LENGTH: 20
<212> TYPE: PRT
<213> ORGANISM: Nicotiana tabacum

<400> SEQUENCE: 38

Ile Ile Leu Leu Leu Ile Ile Ile Leu Val Val Val Leu Ser Ile Gln
1               5                   10                  15

Pro Trp Lys Lys
            20

<210> SEQ ID NO 39
<211> LENGTH: 22
<212> TYPE: PRT
<213> ORGANISM: Arabidopsis thaliana

<400> SEQUENCE: 39

Ile Ile Val Leu Leu Leu Ile Ile Leu Ile Val Val Ile Pro Ile Ile
1               5                   10                  15

Thr Ser Phe Ser Ser Ser
            20

<210> SEQ ID NO 40
<211> LENGTH: 21
<212> TYPE: PRT
<213> ORGANISM: Homo sapiens

<400> SEQUENCE: 40

Ile Ile Ile Cys Cys Val Ile Leu Gly Ile Val Ile Ala Ser Thr Val
1               5                   10                  15

Gly Gly Ile Phe Ala
            20

<210> SEQ ID NO 41
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 41
taatacgact cactataggg                                              20
```

```
<210> SEQ ID NO 42
<211> LENGTH: 17
<212> TYPE: DNA
<213> ORGANISM: Artificial sequence
<220> FEATURE:
<221> NAME/KEY: misc_feature
<222> LOCATION: (1)..(17)
<223> OTHER INFORMATION: primer

<400> SEQUENCE: 42
gtaaaacgac ggccagt                                                  17

<210> SEQ ID NO 43
<211> LENGTH: 19
<212> TYPE: DNA
<213> ORGANISM: Artificial sequence
<220> FEATURE:
<221> NAME/KEY: misc_feature
<222> LOCATION: (1)..(19)
<223> OTHER INFORMATION: primer

<400> SEQUENCE: 43
ggaaacagct atgaccatg                                                19

<210> SEQ ID NO 44
<211> LENGTH: 13
<212> TYPE: PRT
<213> ORGANISM: keyhole limpet haemocyanin

<400> SEQUENCE: 44

Cys Gly Pro Gly Ser Ser Ser Asp Arg Thr Arg Thr Ser
1               5                   10
```